United States Patent
Parihar et al.

(10) Patent No.: US 8,366,635 B2
(45) Date of Patent: Feb. 5, 2013

(54) BIOPSY PROBE AND TARGETING SET INTERFACE

(75) Inventors: Shailendra K. Parihar, Mason, OH (US); Jessica P. Leimbach, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 904 days.

(21) Appl. No.: 12/337,757

(22) Filed: Dec. 18, 2008

(65) Prior Publication Data

US 2010/0160823 A1 Jun. 24, 2010

(51) Int. Cl.
*A61B 5/00* (2006.01)
(52) U.S. Cl. ........................................ 600/564
(58) Field of Classification Search ........... 600/564–568
See application file for complete search history.

(56) References Cited

U.S. PATENT DOCUMENTS

| | | | |
|---|---|---|---|
| 5,226,426 A | 7/1993 | Yoon | |
| 5,285,795 A | 2/1994 | Ryan et al. | |
| 5,490,860 A | 2/1996 | Middle et al. | |
| 5,526,822 A | 6/1996 | Burbank et al. | |
| 5,580,347 A | 12/1996 | Reimels | |
| 5,782,764 A | 7/1998 | Werne | |
| 6,007,497 A | 12/1999 | Huitema | |
| 6,086,544 A | 7/2000 | Hibner et al. | |
| 6,283,925 B1 | 9/2001 | Terwilliger | |
| 6,461,350 B1 | 10/2002 | Underwood et al. | |
| 6,475,190 B2 | 11/2002 | Young | |
| 6,626,849 B2 | 9/2003 | Huitema et al. | |
| 6,638,235 B2 | 10/2003 | Miller et al. | |
| 6,984,213 B2 | 1/2006 | Horner et al. | |
| 7,025,732 B2 | 4/2006 | Thompson et al. | |
| 7,131,951 B2 | 11/2006 | Angel | |
| 7,211,069 B2 | 5/2007 | Lehmann | |
| 7,252,641 B2 | 8/2007 | Thompson et al. | |
| 7,311,673 B2 | 12/2007 | Mueller, Jr. et al. | |
| 7,442,171 B2 | 10/2008 | Stephens et al. | |
| 7,470,237 B2 * | 12/2008 | Beckman et al. | 600/564 |
| 7,481,775 B2 | 1/2009 | Weikel, Jr. et al. | |
| 7,507,210 B2 | 3/2009 | Hibner et al. | |
| 7,527,720 B2 | 5/2009 | Ishimaru et al. | |

(Continued)

FOREIGN PATENT DOCUMENTS

| | | |
|---|---|---|
| DE | 102 27 352 | 1/2004 |
| DE | 20 2008 004 651 | 7/2008 |

OTHER PUBLICATIONS

U.S. Appl. No. 12/337,674.

(Continued)

*Primary Examiner* — Max Hindenburg
(74) *Attorney, Agent, or Firm* — Frost Brown Todd LLC

(57) ABSTRACT

A biopsy device comprises a targeting set assembly, a probe assembly, and a holster assembly, which are detachable from one another. The targeting set assembly comprises a needle assembly, which comprises a connecting member. The probe assembly comprises components configured to selectively attach to the connecting member of the needle assembly. In some versions, the connecting member comprises a recess, and the probe assembly comprises a protrusion configured to selectively engage the recess. The protrusion may be provided on a rocking member or on a resilient arm. The rocking member or resilient arm may bias the protrusion to enter the recess. The connection of the probe assembly to needle assembly provides a device for use during a biopsy procedure. The connection of the probe assembly to needle assembly may further permit rotation of the needle assembly for indexing.

19 Claims, 57 Drawing Sheets

U.S. PATENT DOCUMENTS

| | | | |
|---|---|---|---|
| 7,645,240 | B2 | 1/2010 | Thompson et al. |
| 2003/0199753 | A1 | 10/2003 | Hibner et al. |
| 2003/0199785 | A1 | 10/2003 | Hibner et al. |
| 2004/0167428 | A1 | 8/2004 | Quick et al. |
| 2005/0119627 | A1 | 6/2005 | Crawford |
| 2005/0277829 | A1 | 12/2005 | Tsonton et al. |
| 2006/0195044 | A1* | 8/2006 | Cooke et al. ............ 600/564 |
| 2006/0276772 | A1 | 12/2006 | Moos et al. |
| 2007/0032742 | A1 | 2/2007 | Monson et al. |
| 2007/0167736 | A1 | 7/2007 | Dietz et al. |
| 2007/0239064 | A1* | 10/2007 | Cicenas et al. ............ 600/566 |
| 2008/0045965 | A1 | 2/2008 | Miller et al. |
| 2008/0195066 | A1 | 8/2008 | Speeg et al. |
| 2008/0214955 | A1 | 9/2008 | Speeg et al. |
| 2008/0281226 | A1 | 11/2008 | Peters |
| 2009/0105609 | A1 | 4/2009 | Thompson et al. |
| 2009/0247901 | A1* | 10/2009 | Zimmer ............ 600/567 |

OTHER PUBLICATIONS

U.S. Appl. No. 12/337,684.
U.S. Appl. No. 12/337,720.
U.S. Appl. No. 12/337,785.
International Preliminary Report on Patentability dated Jun. 21, 2011 for Application No. PCT/US2009/067176.
International Preliminary Report on Patentability dated Jun. 21, 2011 for Application No. PCT/US2009/067187.
International Preliminary Report on Patentability dated Jun. 21, 2011 for Application No. PCT/US2009/067195.
U.S. Appl. No. 12/337,814, filed Dec. 18, 2008, Parihar et al.
U.S. Appl. No. 12/337,872, filed Dec. 18, 2008, Parihar et al.
U.S. Appl. No. 12/337,874, filed Dec. 18, 2008, Parihar et al.
U.S. Appl. No. 12/337,911, filed Dec. 18, 2008, Parihar et al.
U.S. Appl. No. 12/337,942, filed Dec. 18, 2008, Parihar et al.
U.S. Appl. No. 60/869,736, filed Dec. 13, 2006, Ritchie et al.
U.S. Appl. No. 60/874,792, filed Dec. 13, 2006, Hibner et al.
International Preliminary Report on Patentability dated Jun. 21, 2011 for Application No. PCT/US2009/067173.
International Preliminary Report on Patentability dated Jun. 21, 2011 for Application No. PCT/US2009/067245.
International Search Report dated Mar. 4, 2010 for Application No. PCT/US2009/067173.
International Search Report dated May 31, 2010 for Application No. PCT/US2009/067176.
International Search Report dated Mar. 10, 2010 for Application No. PCT/US2009/067187.
International Search Report dated Mar. 3, 2010 for Application No. PCT/US2009/067195.
International Search Report dated Mar. 31, 2010 for Application No. PCT/US2009/067245.
U.S. Appl. No. 12/337,674, filed Dec. 18, 2008, Parihar et al.
U.S. Appl. No. 12/337,785, filed Dec. 18, 2008, Parihar.

* cited by examiner

BIOPSY PROBE AND TARGETING SET INTERFACE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. Patents, U.S. Patent Application Publications, and U.S. Provisional Patent Applications is incorporated by reference herein.

Some biopsy systems may provide a probe assembly having an attached needle. Such biopsy systems may also be used with a cannula and obturator, which are used to create the channel through the tissue to a desired biopsy site. In some such biopsy systems, the obturator may be removed once the cannula is positioned, and the needle of the probe assembly may be inserted through the cannula to reach the biopsy site. The tissue sample may then be pulled through aligning apertures in the cannula and needle into an axial lumen of the needle. A cutter may then travel through the axial lumen to sever the tissue sample. In some situations, it might be desirable to eliminate one or more of the components that enter the patient's tissue during a biopsy procedure. One situation may be to eliminate the outer cannula by using a biopsy system having a probe assembly, including a cutter, and a separate targeting set assembly, including a needle. Once the targeting set assembly is positioned—with needle adjacent to the targeted tissue—the probe assembly may be attached to the targeting set assembly for severing and removing the targeted tissue.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

DETAILED DESCRIPTION

The following description of certain examples should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy System

Figure 1:
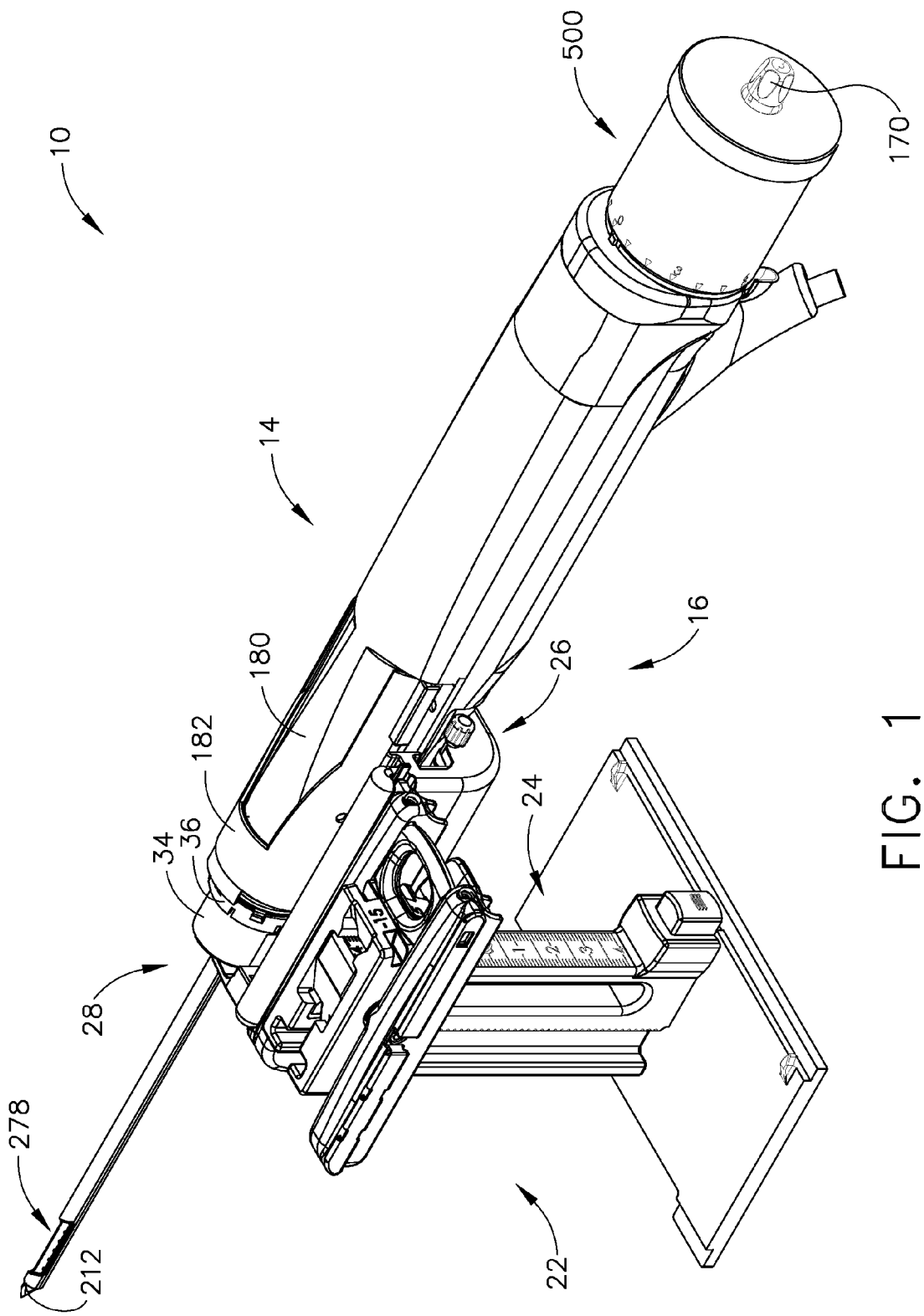
FIG. 1 depicts a perspective view of an exemplary MRI biopsy device showing a holster assembly, probe assembly, and targeting set assembly.
Figure 59:
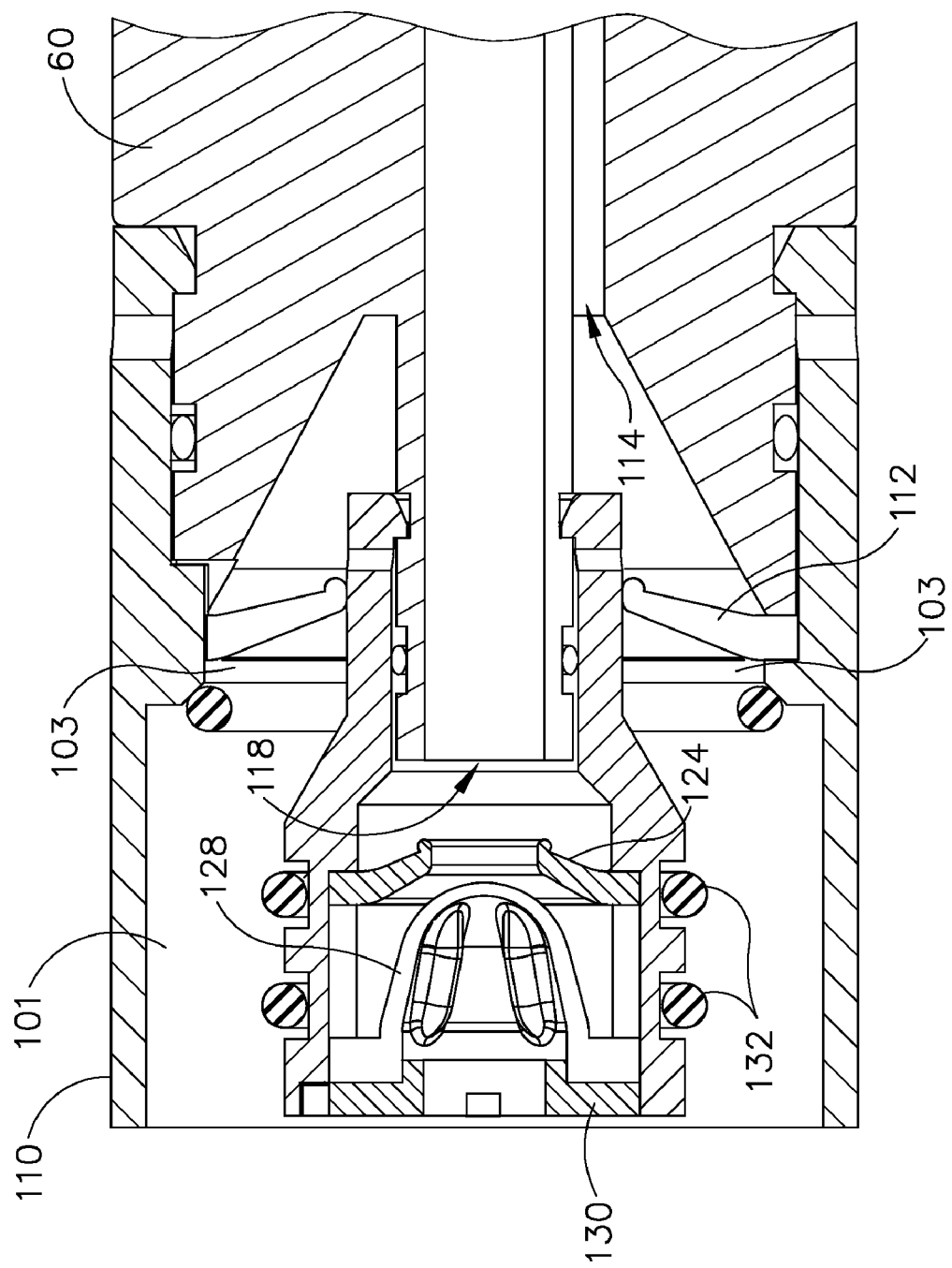
FIG. 59 depicts a cross-sectional view of the proximal end of the needle assembly shown in FIG. 28, attached to a probe assembly.

FIGS. 1-59 show various components that may be incorporated into a biopsy system. By way of example only, a biopsy system may include a biopsy device (10, 12) and a vacuum control module (not shown). In some uses, biopsy device (10, 12) may be operated in a handheld fashion (e.g., under ultrasound imaging guidance). In some other uses, biopsy device (10, 12) may be secured to a platform, table, or other fixture. For instance, a biopsy device (10, 12) may be used in combination with stereotactic or MRI imaging. In such uses, a biopsy device (10, 12) may be secured to a targeting set, which may be used to position biopsy device (10, 12) to specifically target a suspicious region of tissue (e.g., within a patient's breast or elsewhere). Examples of targeting set assemblies (22, 23) with biopsy devices (10, 12) are shown in FIGS. 1-2 and 12-14, and will be described in greater detail below.

As will also be described in greater detail below, biopsy devices (10, 12) shown in FIGS. 1, 7, and 12 comprise a probe assembly (14, 18, 19) and a holster assembly (16, 20, 21). In versions described herein, each biopsy device (10, 12) lacks an integral needle. Instead, a separate needle assembly (28, 29, 30, 134, 160, 161) is removably coupled with a targeting set assembly (22, 23). Probe assembly (14, 18, 19) is operable to removably couple with such a needle assembly (28, 29, 30, 134, 160, 161).

Needle assembly (28, 29, 30, 134, 160, 161) of the present example comprises a needle (42, 44, 64), which includes a tissue piercing tip (212), a transverse tissue receiving aperture (278), a lumen (82) for receiving a cutter (106, 107), a lateral lumen (84) running parallel with lumen (82), and openings (86) for providing fluid communication from lateral lumen (84) to lumen (82). As will also be described in greater detail below, probe assembly (14, 18, 19) includes cutter (106, 107), which is configured to rotate and translate within lumen (82) when probe assembly (14, 18, 19) is coupled with needle assembly (28, 29, 30, 134, 160, 161). For instance, when a distal portion of needle assembly (28, 29, 30, 134, 160, 161) is inserted into a patient's breast, tissue may be drawn into aperture (278) under influence of a vacuum. Cutter (106, 107) may then simultaneously rotate and translate within lumen (82) to sever a tissue sample from such tissue protruding into aperture (278).

An exemplary vacuum control module may provide power (e.g., electrical, pneumatic, etc.), control signals, saline, vacuum, pressurized air and/or venting from the vacuum control module to biopsy device (10, 12). For instance, a vacuum control module may provide a vacuum to lumen (82) via one path; while providing a vacuum or venting to lateral lumen (84) via another path (e.g., a path that includes a manifold (97, 99, 101) of probe assembly (14, 18, 19), etc.). Examples of components, features, and methods of operating a vacuum control module are described in U.S. Pub. No. 2008/0195066, entitled "Revolving Tissue Sample Holder For Biopsy Device," published Aug. 14, 2008, the disclosure of which is incorporated by reference herein. In some versions, a vacuum control module interface may be provided between biopsy device (10, 12) and the vacuum control module, such as the vacuum control module interface described in U.S. Non-Provisional patent application Ser. No. 12/337,814, entitled "CONTROL MODULE INTERFACE," filed on even date herewith, now published as U.S. Pat. Pub. No. 2010/0160817, the disclosure of which is incorporated by reference herein.

II. Exemplary Targeting Set Assemblies

An exemplary targeting set assembly may be comprised of several assemblies in combination. Such assemblies may include a stand assembly (24), cradle assembly (26, 32), and needle assembly (28, 29, 30, 134, 160, 161). These assemblies will be discussed in greater detail in the sections that follow. However, it should be understood that a targeting set assembly may comprise a variety of other components in addition to or in lieu of any of the components described below. Other suitable components, features, configurations, and methods of operating a targeting set assembly will be apparent to those of ordinary skill in the art in view of the teachings herein.

A. Exemplary Stand and Cradle Assemblies

Figure 12:
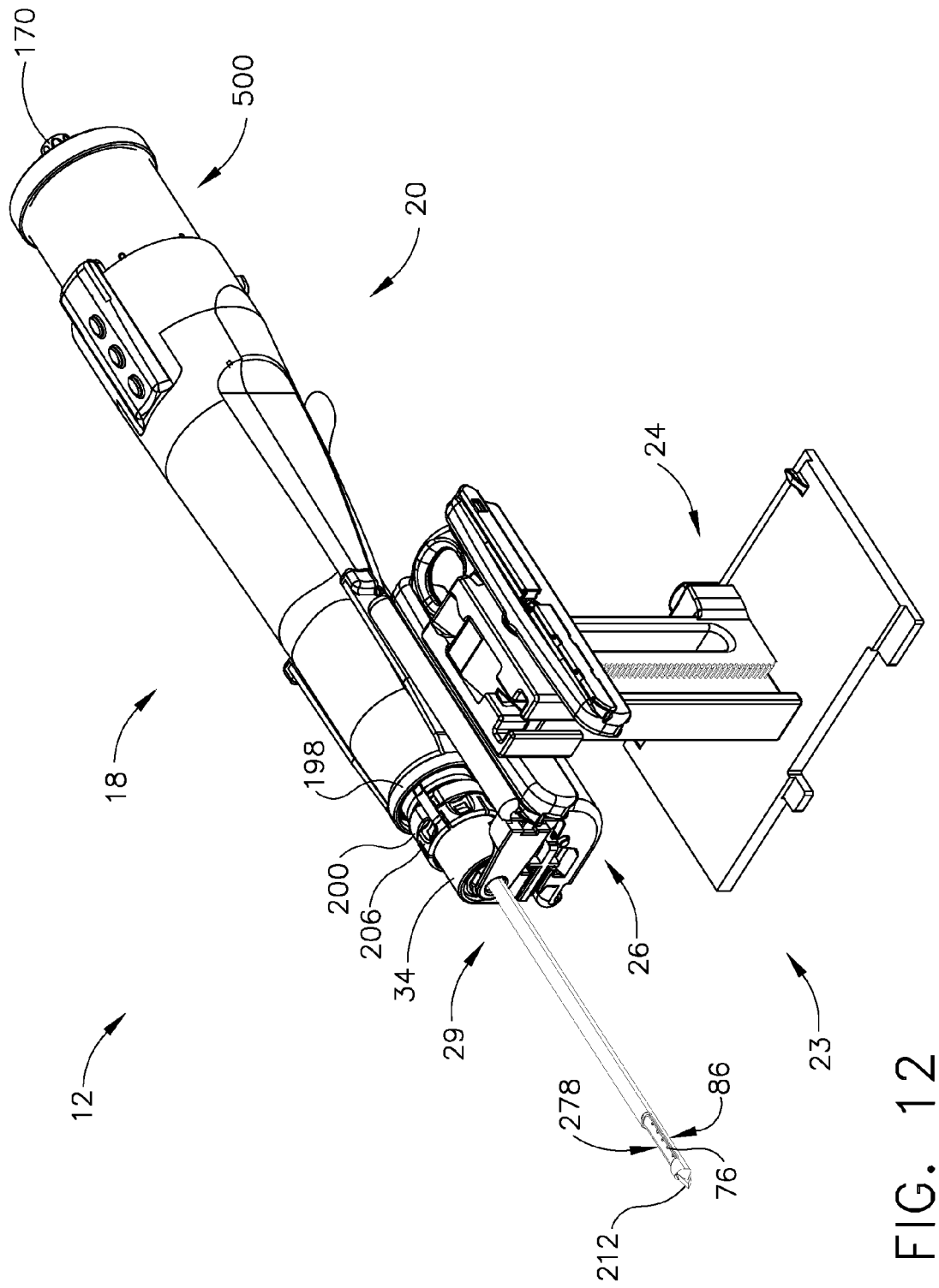
FIG. 12 depicts a perspective view of another exemplary MRI biopsy device, showing a holster assembly, probe assembly, and targeting set assembly.
Figure 28:
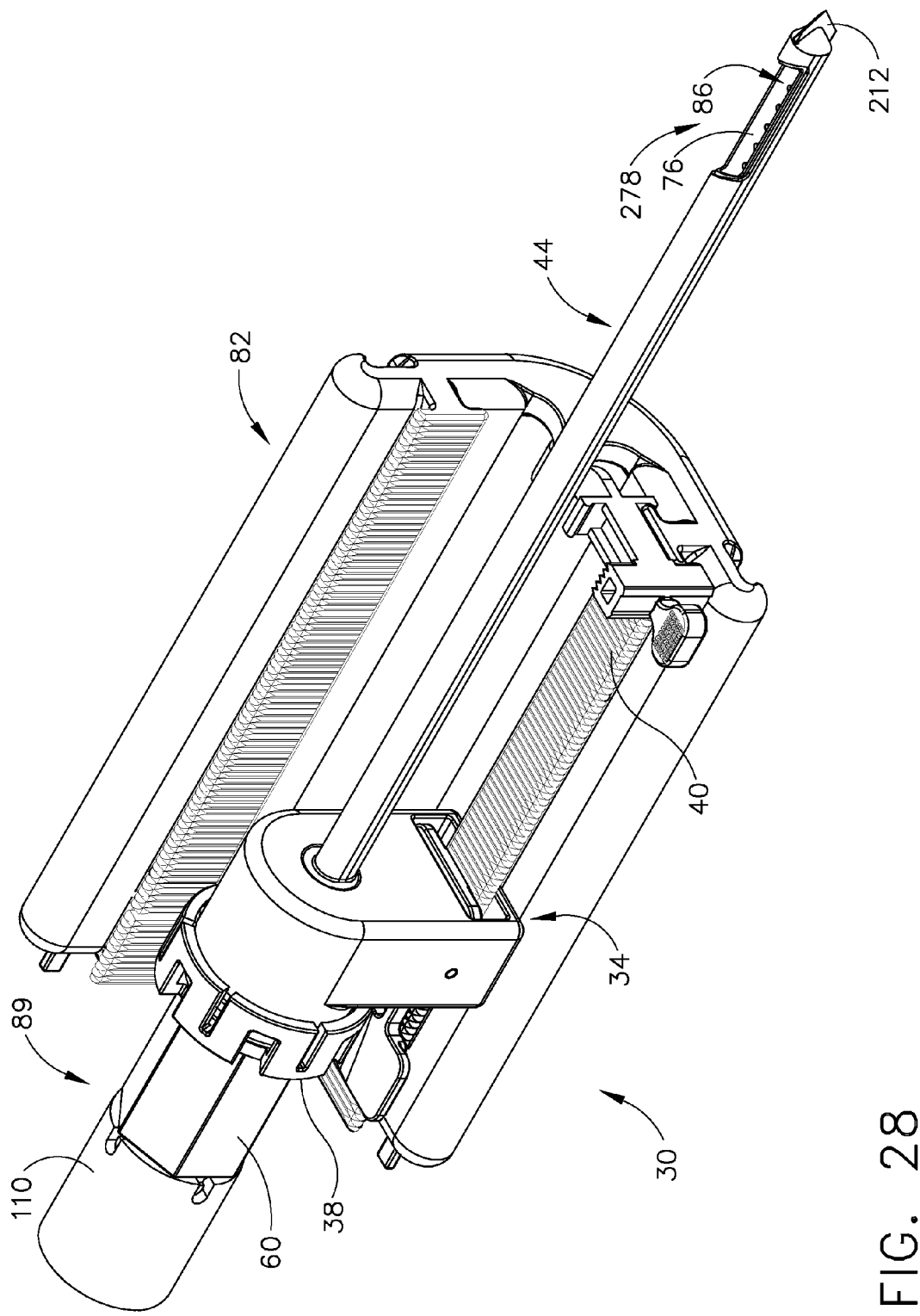
FIG. 28 depicts a perspective view of another exemplary detachable needle assembly of a MRI biopsy device, showing a cradle assembly, needle assembly, and sleeve mount.

As shown in FIGS. 1, 12, 28, the targeting set assemblies (22, 23) of the present example include a stand assembly (24), a cradle assembly (26, 32), and a needle assembly (28, 29, 30, 134, 160, 161). By way of example only, stand assembly (24) may comprise a conventional stand that is part of a breast biopsy MRI guidance system by Invivo Corp. of Orlando, Fla. Of course, any other suitable type of stand assembly (24) may be used. Stand assembly (24) of the present example engages with cradle assembly (26), which further engages with needle assembly (28, 29, 30, 134, 160, 161). Stand assembly (24) and cradle assembly (26) may be adjustable to allow for positioning of needle assembly (28, 29, 30, 134, 160, 161) at a desired location. For instance, stand assembly (24) may permit vertical adjustment of the cradle assembly (26), while cradle assembly (26) may permit horizontal adjustment or depth-of-insertion (a.k.a. z-depth) adjustment of needle assembly (28, 29, 30, 134, 160, 161). Those of ordinary skill in the art will further appreciate that rotational adjustment may be incorporated into stand assembly (24) and cradle assembly (26).

Suitable components of, features of, configurations of, and methods of operating stand assembly (24) and cradle assembly (26, 32), as well as ways in which biopsy devices (10, 12) may be coupled with cradle assembly (26, 32), are described in further detail in U.S. Non-Provisional patent application Ser. No. 12/337,986, entitled "MUTLI-ORIENTATION TARGETING SET FOR MRI BIOPSY DEVICE," filed on even date herewith, now published as U.S. Pat. Pub. No. 2010/0160825, the disclosure of which is incorporated by reference herein. Of course, it will be appreciated in view of the disclosure herein that biopsy devices (10, 12) may be used in a variety of other settings and combinations. For instance, as one merely illustrative alternative, any of biopsy devices (10, 12) and/or needle assemblies (28, 29, 30, 134, 160, 161) described herein may be coupled with a cube as described in U.S. Pub. No. 2007/0255170, entitled "BIOPSY CANNULA ADJUSTABLE DEPTH STOP," published Nov. 1, 2007, the disclosure of which is incorporated by reference herein. Exemplary needle assemblies (28, 29, 30), including those shown in FIGS. 1, 12, and 28, will be described in greater detail below.

B. Exemplary Needle Assemblies

As noted above, needle assembly (28, 29, 30, 134, 160, 161) of the examples described below each comprises a needle (42, 44, 64), which includes a tissue piercing tip (212), a transverse tissue receiving aperture (278), a lumen (82) for receiving a cutter (106, 107), a lateral lumen (84) running parallel with lumen (82), and openings (86) for providing fluid communication from lateral lumen (84) to lumen (82). Lumen (82) is configured to receive a cutter (106, 107) from a probe assembly (14, 18, 19) includes cutter (106, 107). For instance, when a distal portion of needle (42, 44, 64) is inserted into a patient's breast, tissue may be drawn into aperture (278) under influence of a vacuum. Cutter (106, 107) may then simultaneously rotate and translate within lumen (82) to sever a tissue sample from such tissue protruding into aperture (278).

In some existing biopsy systems that are used in an MRI setting, a targeting cannula and obturator are used, which are separate from a biopsy device. The cannula has a transverse aperture, similar to aperture (278). For instance, in some uses of such systems, the cannula and obturator are inserted into a patient's breast, and the transverse aperture of the cannula is positioned near a suspicious lesion. Such positioning of the transverse aperture of the cannula may be assisted by MRI imaging and targeting routines. The obturator may then be removed from the cannula, and the integral needle of a biopsy device may be inserted into the obturator. To the extent that the integral needle of the biopsy device also has a transverse aperture, that transverse aperture may be substantially aligned with the transverse aperture of the targeting cannula. A cutter in the biopsy device may then be translated and rotated relative to both apertures to sever tissue protruding therethrough. Examples of such biopsy systems are disclosed in U.S. Pub. No. 2005/0277829, entitled "MRI BIOPSY APPARATUS INCORPORATING A SLEEVE AND A MULTI-FUNCTION OBTURATOR," published Dec. 15, 2005, the disclosure of which is incorporated by reference herein; and U.S. Pub. No. 2007/0167736, entitled "MRI BIOPSY APPARATUS INCORPORATING AN IMAGEABLE PENETRATING PORTION," published Jul. 19, 2007, the disclosure of which is incorporated by reference herein.

It should be understood that, in some settings, examples of needle assembly (28, 29, 30, 134, 160, 161) described herein may eliminate the need for having both a targeting cannula that is separate from a biopsy device and a needle that is integral with the biopsy device for insertion into the targeting cannula as described in the above-referenced published U.S. patent applications. In other words, in some settings, examples of needle assembly (28, 29, 30, 134, 160, 161) described herein may provide combined functionalities of both the targeting cannulas and the integral needles described in the above-referenced published U.S. patent applications. For instance, a detachable needle assembly is described in U.S. Pub. No. 2003/0199785, entitled "LOCALIZATION MECHANISM FOR AN MRI COMPATIBLE BIOPSY DEVICE," published Oct. 23, 2003, the disclosure of which is incorporated by reference herein. Some examples of needle assembly (28, 29, 30, 134, 160, 161) described herein may also be used as a targeting cannula, separate from probe assembly (14, 18, 19), at initial stages of operation. Needle assembly (28, 29, 30, 134, 160, 161) may thus be used with an obturator (not shown) as described in the above-referenced published U.S. patent applications, to position aperture (278) near suspicious tissue. The obturator may then be removed, and a probe assembly (14, 18, 19) may be coupled with needle assembly (28, 29, 30, 134, 160, 161) while needle (42, 44, 64) is still in the patient's breast (or other tissue area). Probe assembly (14, 18, 19) and needle assembly (28, 29, 30, 134, 160, 161) may then be used to acquire a tissue sample as described herein.

While several needle assemblies (28, 29, 30) will be discussed in greater detail below, it should be understood that the components, features, configurations, and methods of operation of needle assemblies (28, 29, 30) are not limited to the contexts provided below. In particular, components, features, configurations, and methods of operation described in the context of one of the exemplary needle assemblies (28, 29, 30) may be incorporated into any of the other needle assemblies (28, 29, 30). Furthermore, additional and alternative suitable components, features, configurations, and methods of operation for needle assemblies (28, 29, 30) will be apparent to those of ordinary skill in the art in view of the teachings herein.

1. Exemplary Needle Assembly Mounting

Figure 22:
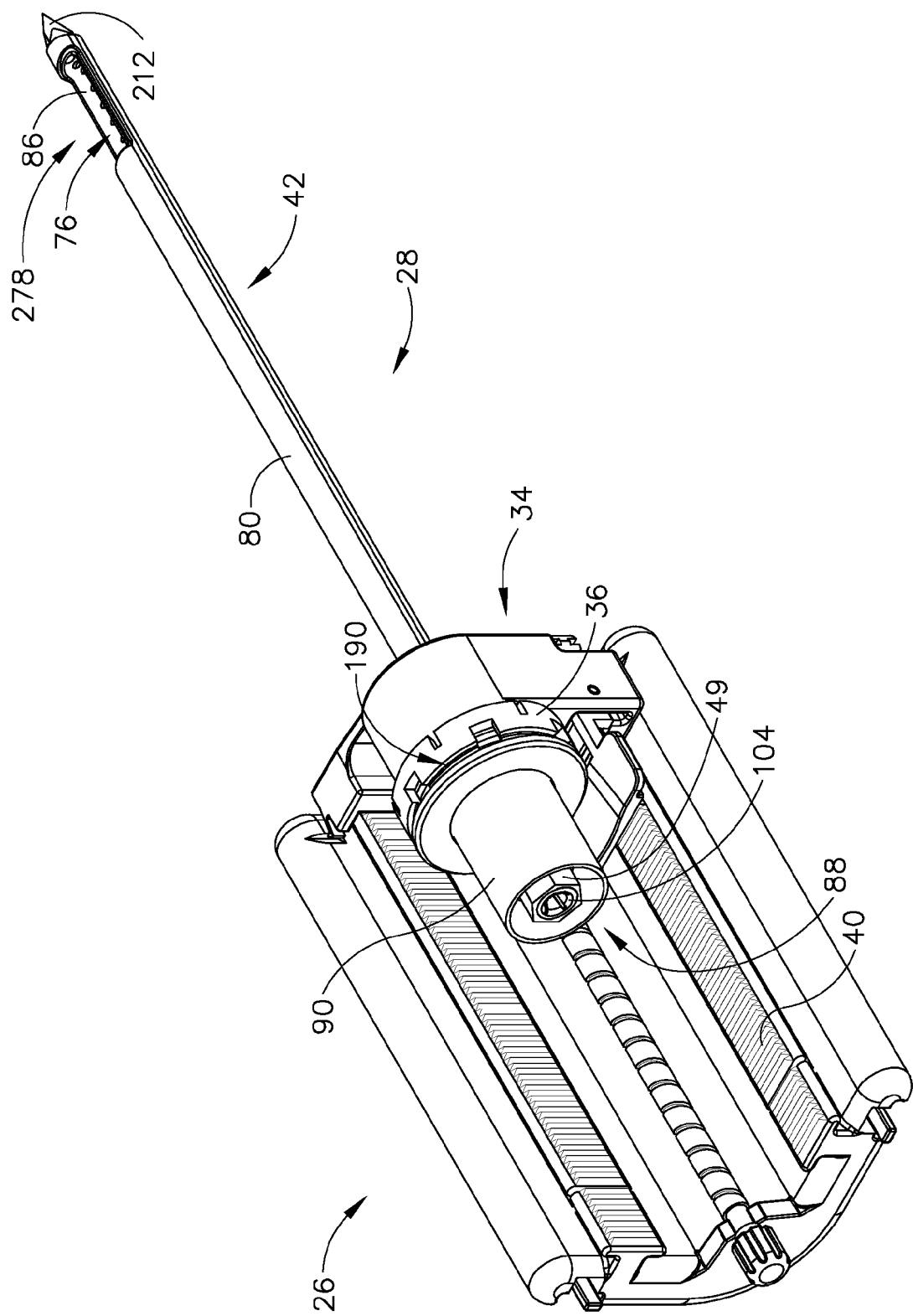
FIG. 22 depicts a perspective view of an exemplary detachable needle assembly of a MRI biopsy device, showing a cradle assembly, needle assembly, and sleeve mount.
Figure 27:
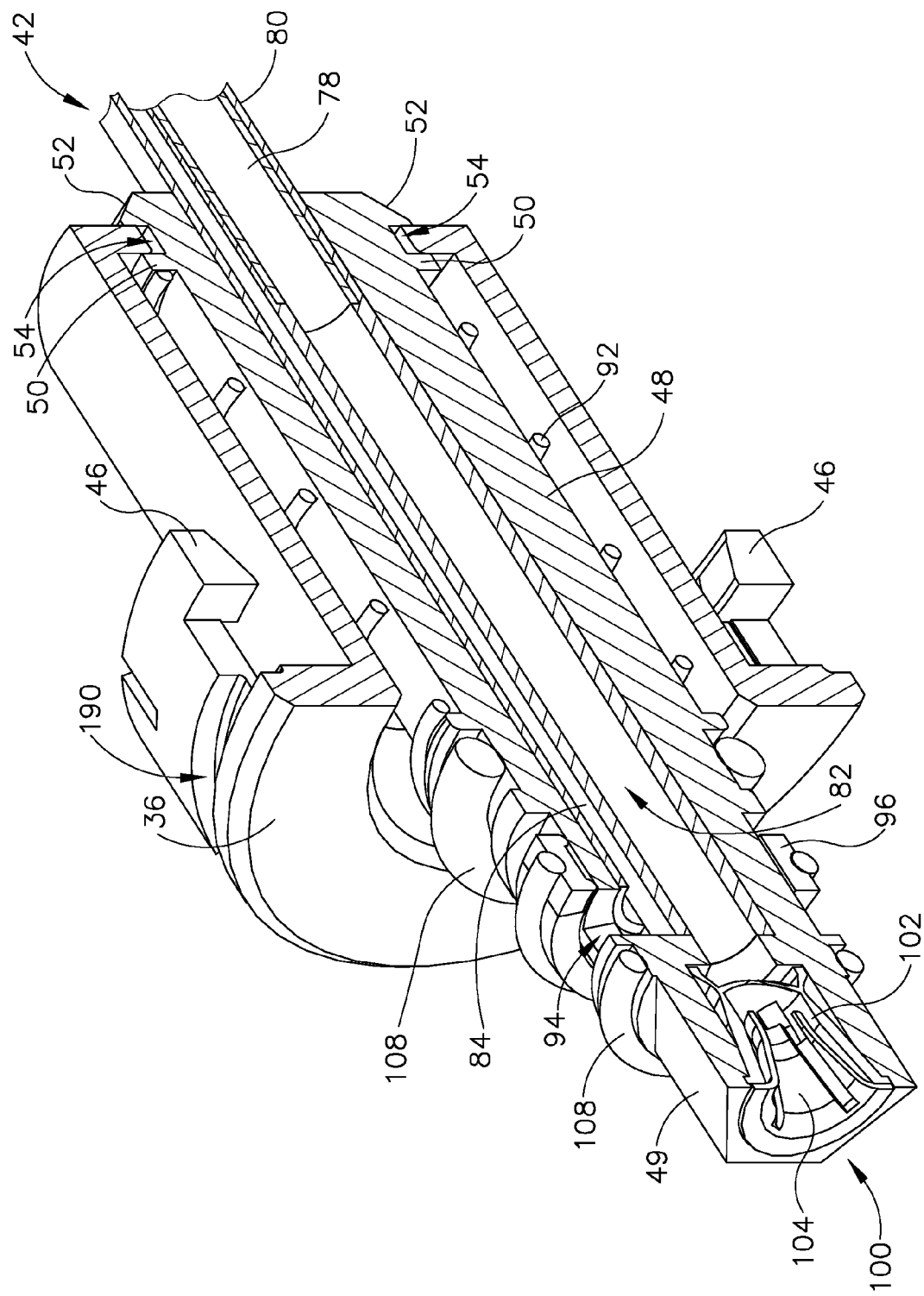
FIG. 27 depicts a cross-sectional view of the proximal end of the needle assembly of FIG. 22, with the telescopic sleeve removed.

When considering needle assembly (28, 29, 30, 134, 160, 161), one aspect to address may include modes for mounting needle assembly (28, 29, 30, 134, 160, 161) to cradle assembly (26, 32). FIGS. 22 and 28 show exemplary needle assemblies (28, 30) coupled to exemplary cradle assemblies (26, 32). Cradle assemblies (26, 32) include a sleeve mount (34) as an exemplary mode of connecting needle assembly (28, 30) to cradle assembly (26, 32). For instance, in FIGS. 22 and 28, sleeve mount (34) provides one or more grooves or recesses at its proximal end for connecting to a thumbwheel (36, 38) of needle assembly (28, 30). Thumbwheel (36, 38) comprises protrusions (46) along an interior surface, as shown in FIG. 27. Protrusions (46) engage the groove(s) or recess(es) of sleeve mount (34) to create a removably secure connection, such as through a "snap fit."

Sleeve mount (34) may further be configured to slide along a track (40) located on cradle assembly (26, 32) as shown in FIGS. 22 and 28. One or more locking mechanisms (not shown), incorporated into cradle assembly (26, 32) and/or needle assembly (28, 30), may permit an operator to selectively lock the position of sleeve mount (34) at a desired longitudinal position along track (40). Such movement along track (40) and selective locking relative to track (40) may permit an operator to set needle assembly (28, 30) at a desired depth of insertion for needle assembly (28, 30) into a patient.

Additional ways in which a needle assembly (28, 29, 30, 134, 160, 161) may mount to a cradle assembly (26, 32), as well as other methods of operating the same, are disclosed in U.S. Non-Provisional patent application Ser. No. 12/337,986, entitled "MUTLI-ORIENTATION TARGETING SET FOR MRI BIOPSY DEVICE," filed on even date herewith, now published as U.S. Pat. Pub. No. 2010/0160825, the disclosure of which is incorporated by reference herein. Of course, a needle assembly (28, 29, 30, 134, 160, 161) may mount to cradle assembly (26, 32) in any other suitable fashion, and needle assembly (28, 29, 30, 134, 160, 161) may have any other suitable relationship with cradle assembly (26, 32). Other suitable relationships, mounting techniques, structures, and configurations will be apparent to those of ordinary skill in the art in view of the teachings herein.

Figure 24:
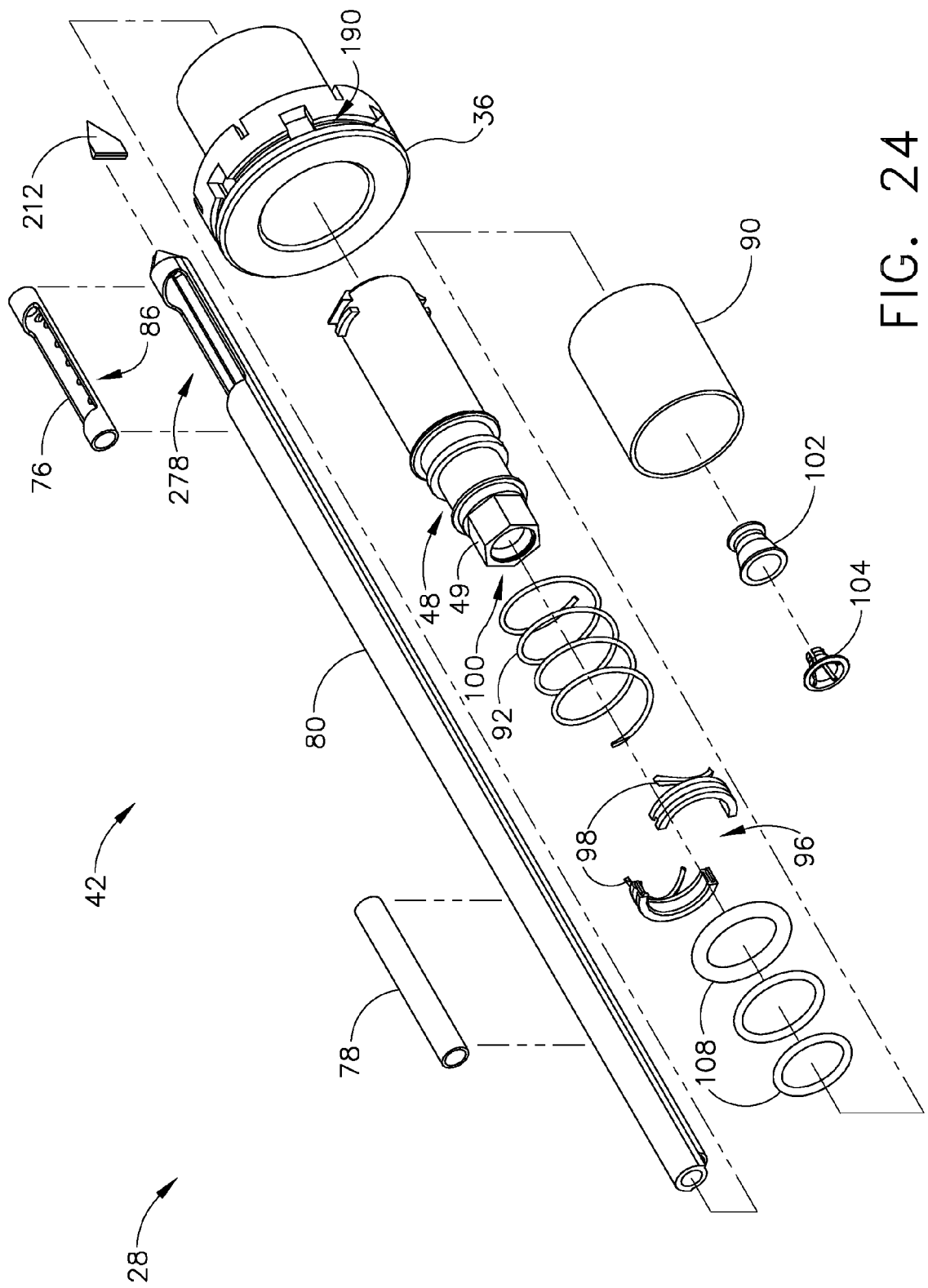
FIG. 24 depicts an exploded view of the needle assembly of FIG. 22.
Figure 25:
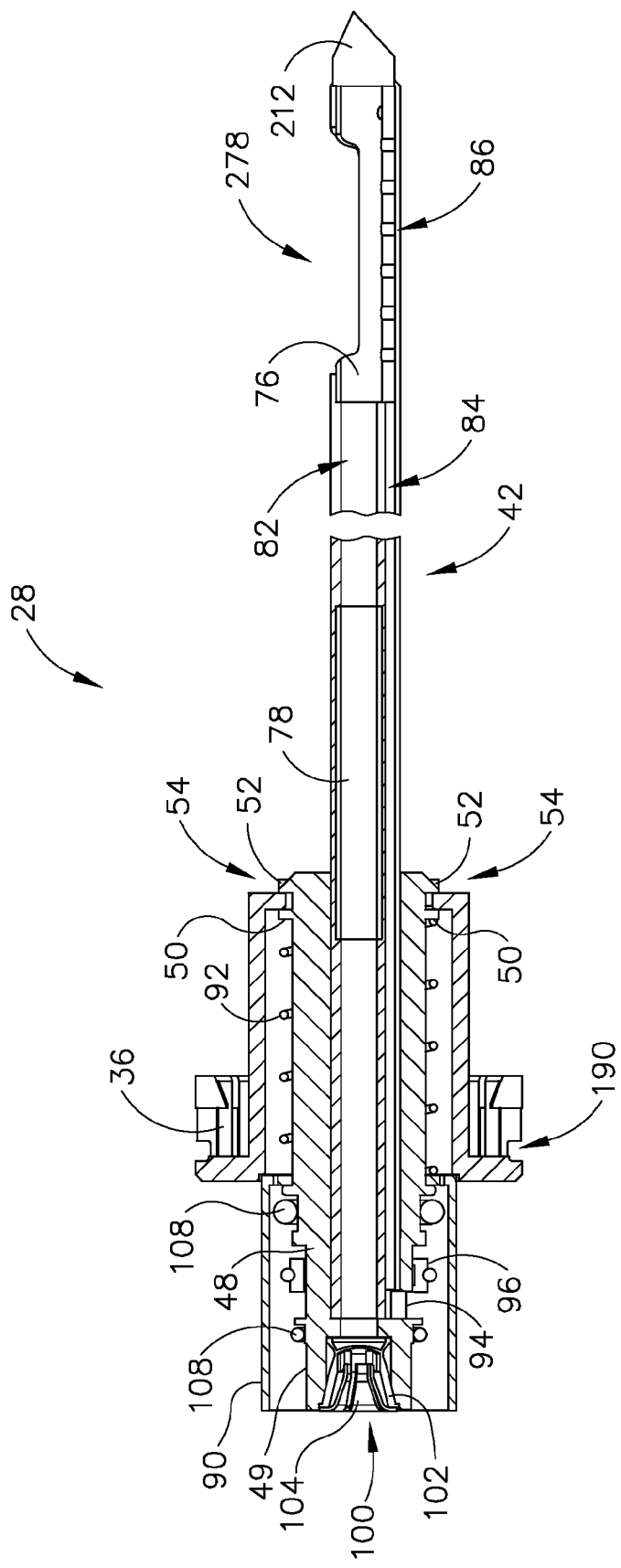
FIG. 25 depicts a cross-sectional view of the needle assembly of FIG. 22.
Figure 26:
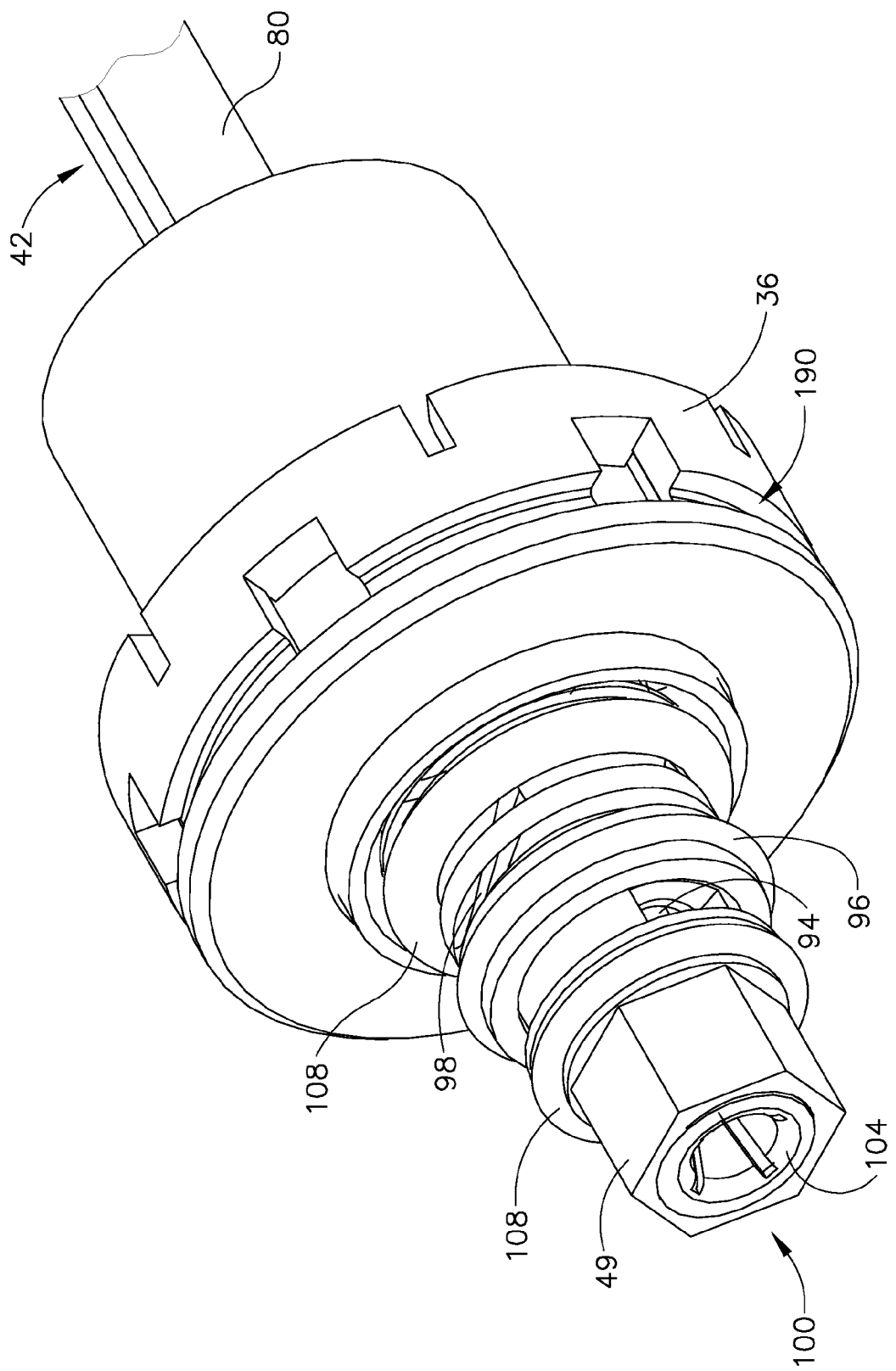
FIG. 26 depicts a partial perspective view of the proximal end of the needle assembly of FIG. 22, with the telescopic sleeve and telescopic sleeve spring removed.

Another aspect to address when considering needle assembly (28, 29, 30, 134, 160, 161) may include modes for mounting needle (42, 44) to needle assembly (28, 29, 30, 134, 160, 161). By way of example only, needle (42, 44) may engage with thumbwheel (36, 38) in a variety of ways to make a suitable connection. For instance, as shown in FIGS. 24, 25, and 27, needle (42) may comprise a proximal mounting portion (48), which includes projection members (50) and stopping members (52) near the distal end. Proximal mounting portion (48) may be overmolded about needle (42), such that proximal mounting portion (48) is unitarily secured to needle (42). The orientation of projection members (50) and stopping members (52) create partial grooves (54) on both sides of mounting portion (48) in this example. In a completed needle assembly (28), an interior lip and/or inward protrusions (not shown) on the distal end of thumbwheel (36) engage with partial grooves (54) of the mounting portion (48), providing "snap fit." Projection members (50) and stopping members (52) thereby restrict further movement of the thumbwheel (36) with respect to the needle (42). Thumbwheel (36) and needle (42) thus translate and rotate unitarily in this example.

Figure 30:
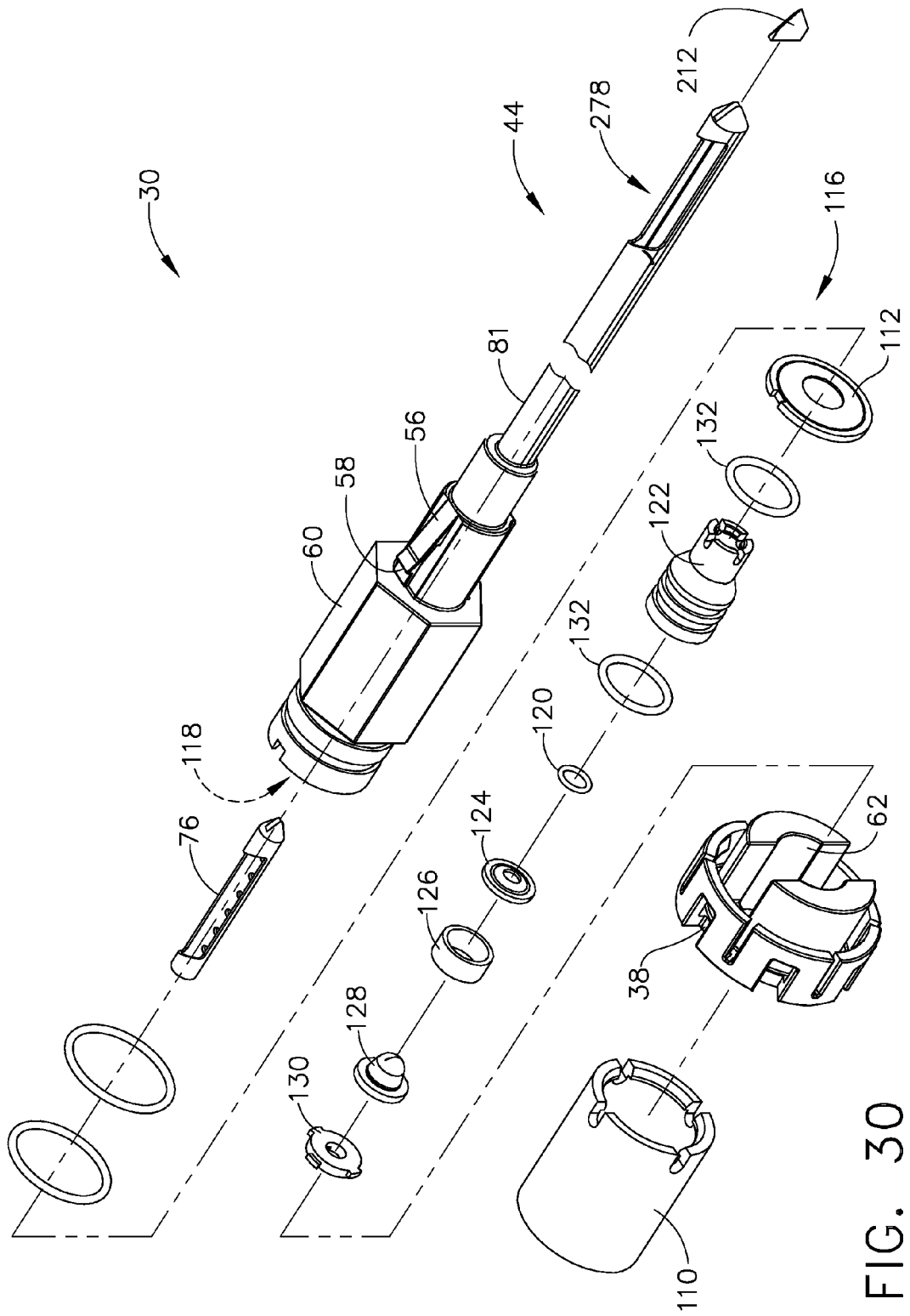
FIG. 30 depicts an exploded view of the proximal end of the needle assembly of FIG. 28.
Figure 31:
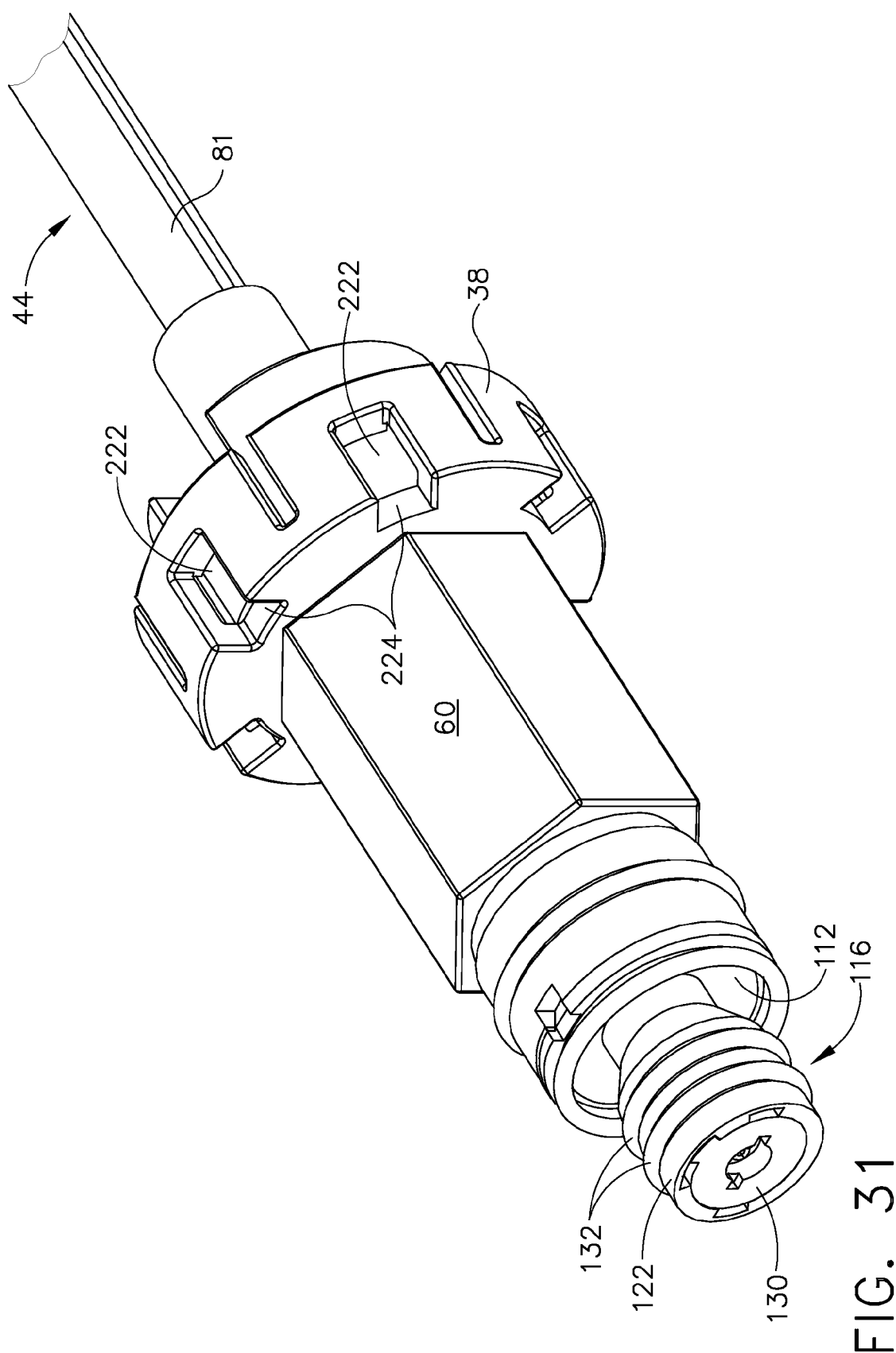
FIG. 31 depicts a partial perspective view of the proximal end of the needle assembly of FIG. 28.
Figure 32:
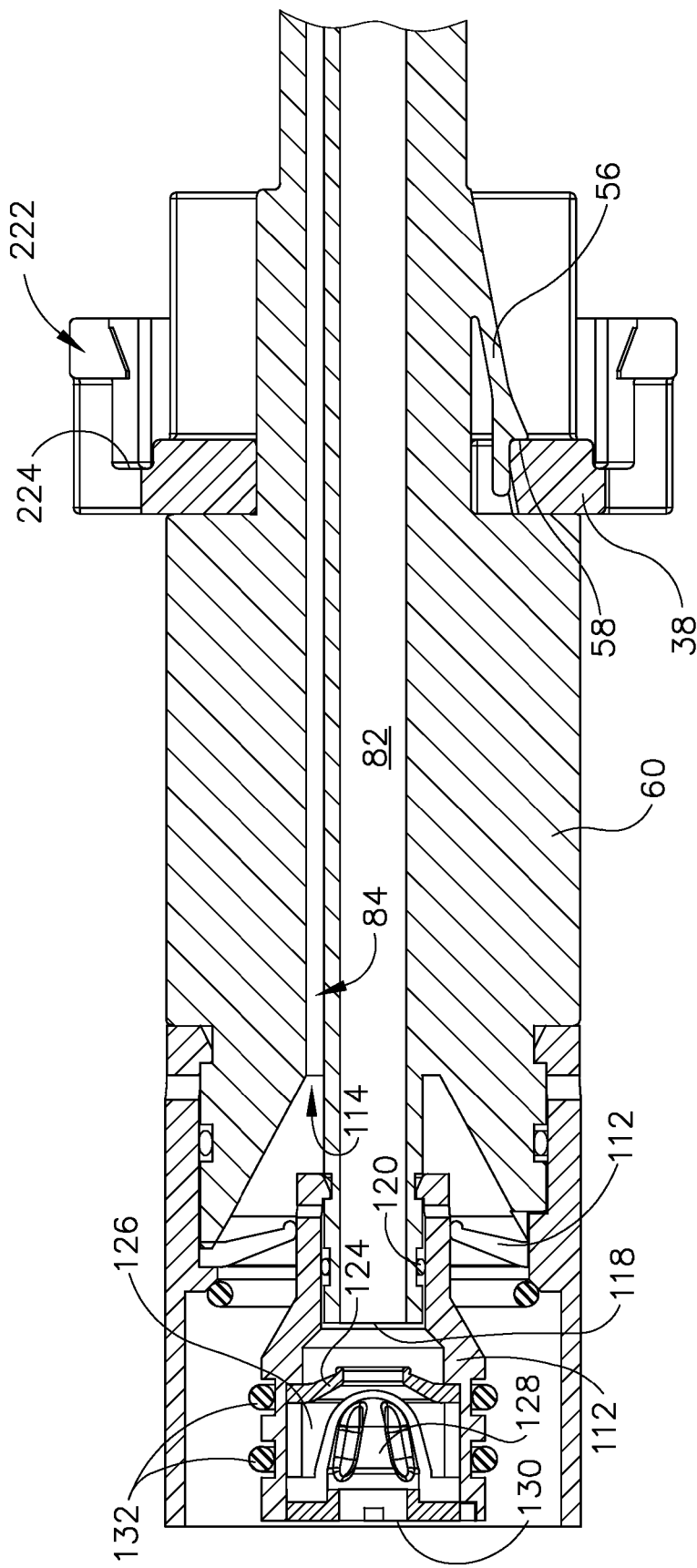
FIG. 32 depicts a cross-sectional view of the proximal end of the needle assembly of FIG. 28.

In another exemplary needle (44) to thumbwheel (38) connection, as shown in FIGS. 30 and 32, needle (44) includes a locking tab (56) having a stopper (58), and a mounting portion (60). Thumbwheel (38) includes an opening (62) to receive locking tab (56). Locking tab (56) is capable of deflecting to allow opening (62) of thumbwheel (38) to engage locking tab (56). Mounting portion (60) is sized such that thumbwheel (38) cannot translate over mounting portion (60) in this example. In a completed needle assembly (30), once thumbwheel (38) and needle (44) are engaged, stopper (58) of locking tab (56) and mounting portion (60) restrict further movement of thumbwheel (38) with respect to needle (44). Thumbwheel (38) and needle (44) thus translate and rotate unitarily in this example.

Figure 48:
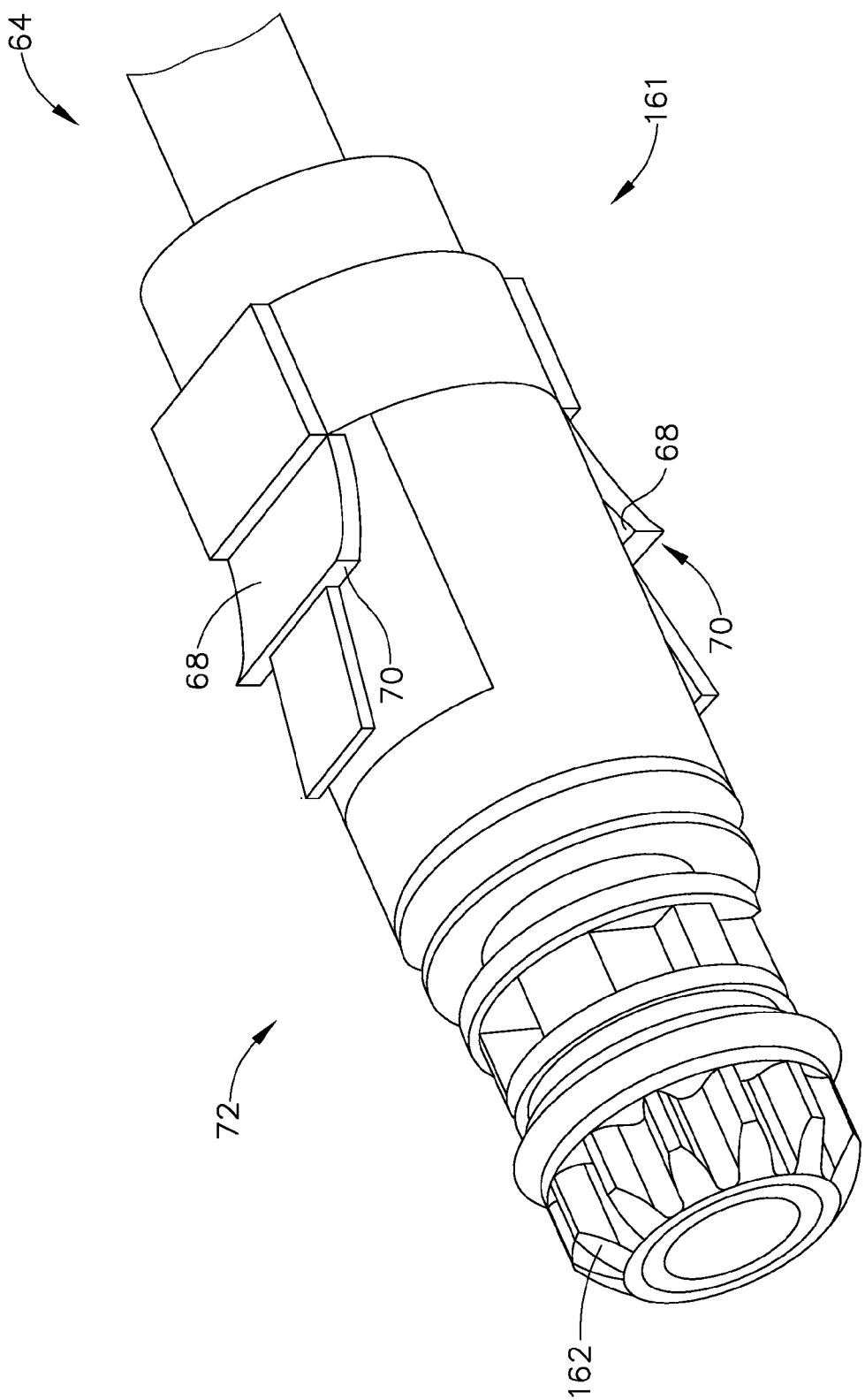
FIG. 48 depicts a perspective view of a proximal end of another exemplary needle assembly, having a snap connection for engaging a thumbwheel.
Figure 49:
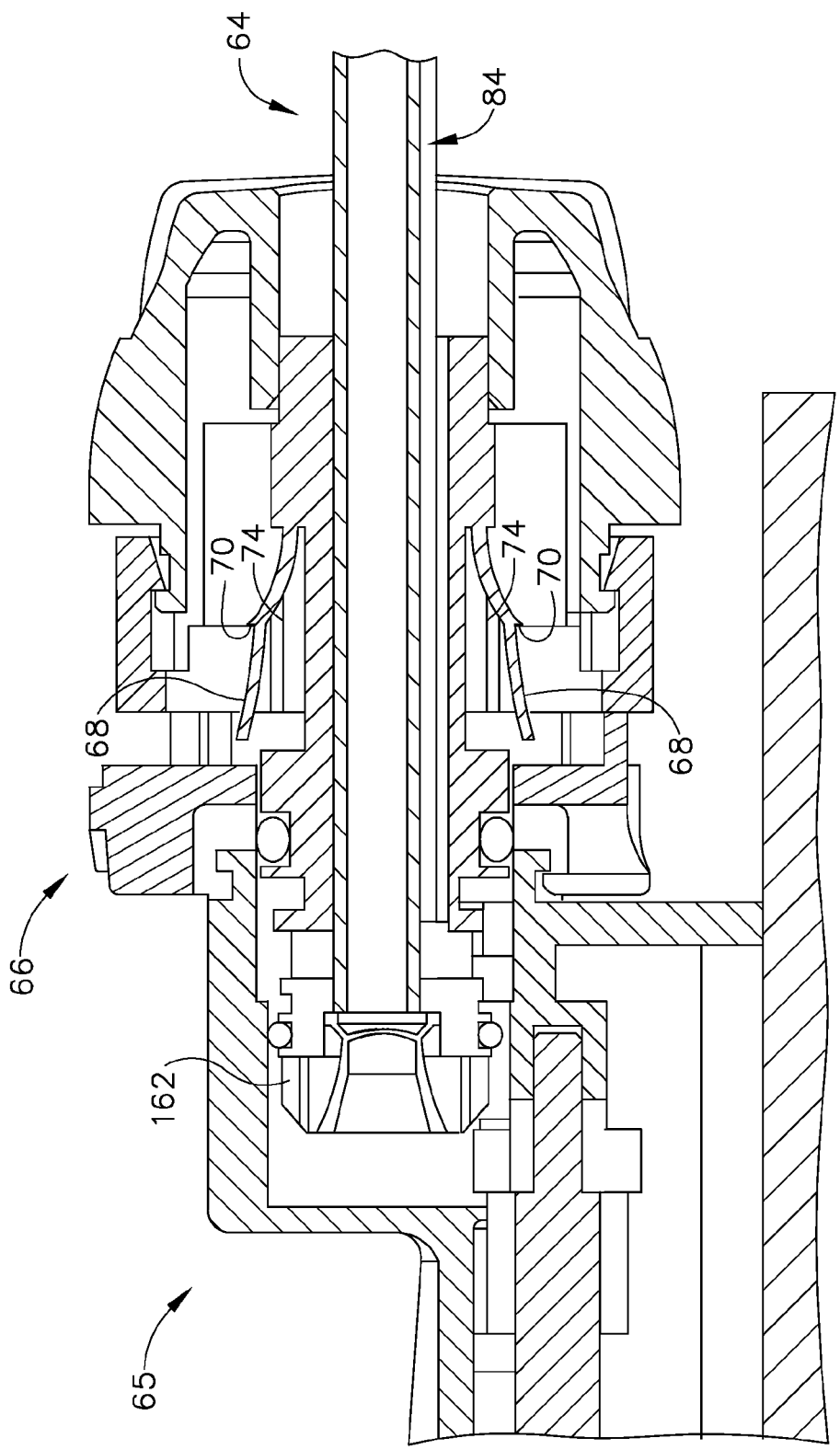
FIG. 49 depicts a cross-sectional view of the needle assembly of FIG. 48 coupled with a probe assembly, and showing engagement of the snap connection to a thumbwheel.

In another exemplary needle (64) to thumbwheel (66) connection, as shown in FIGS. 48 and 49, dual locking tabs (68) are shown. In this arrangement, the proximal end of needle (64) includes a mounting portion (72) having dual locking tabs (68). A separate thumbwheel (66) is mounted on a probe assembly (65). Thumbwheel (66) includes dual openings (74) for engaging dual locking tabs (68) of mounting portion (72). Dual locking tabs (68) are capable of deflecting to allow dual openings (74) of the thumbwheel (66) to engage dual locking tabs (68). Once mounting portion (72) and thumbwheel (66) are engaged, stoppers (70) on dual locking tabs (68) restrict distal movement of the thumbwheel (66). Further proximal movement of the thumbwheel (66) is restricted by probe assembly (65). Thumbwheel (66) and needle (64) thus translate and rotate unitarily in this example.

Of course, a needle (42, 44, 64) may be incorporated into a needle assembly (28, 29, 30, 134, 160, 161) in any other suitable fashion, and needle (42, 44, 64) may have any other suitable relationship with needle assembly (28, 29, 30, 134, 160, 161). Other suitable relationships, mounting techniques, structures, and configurations will be apparent to those of ordinary skill in the art in view of the teachings herein.

2. Exemplary Needle Deflection Reduction

Figure 23:
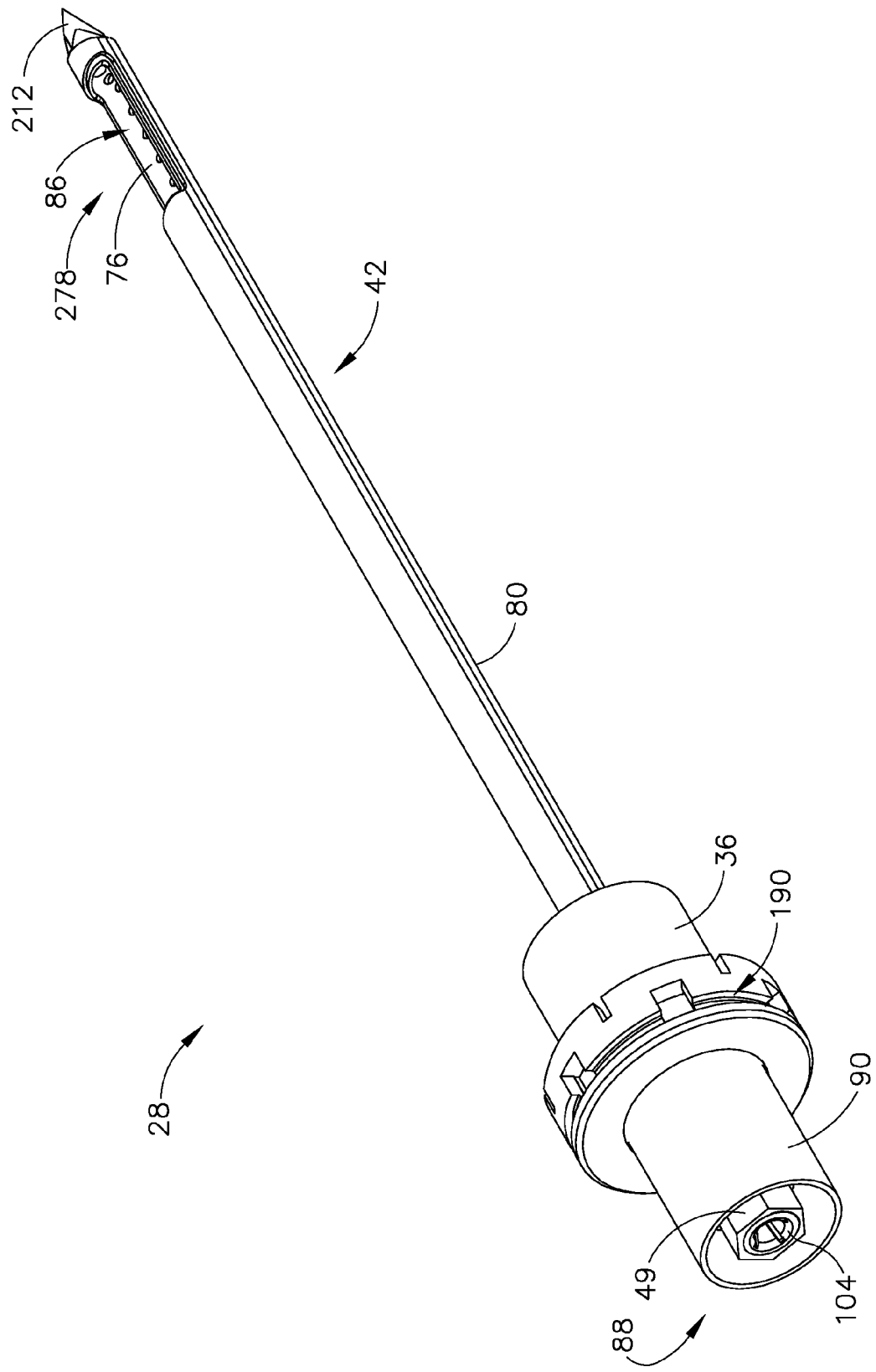
FIG. 23 depicts a perspective view of the needle assembly of FIG. 22.

Another aspect to address when considering a detachable needle assembly (28, 29, 30, 134, 160, 161) may be minimizing needle deflection as needle (42, 44, 64) is inserted into a patient, while maintaining imaging ability (e.g., under MRI, etc.). As shown in FIGS. 23 and 24, needle (42) of needle assembly (28) may include a first ceramic insert (76), a second ceramic insert (78), and an over-molded portion (80). Over-molded portion (80) may be a MRI compatible material, such as a suitable thermoplastic. Vectra® liquid crystal polymer is a commercially available example of a suitable over-molding material, available from Ticona, a company of Celanese Corporation. Other suitable materials and combinations of materials will be apparent to those of ordinary skill in the art in view of the teachings herein. First ceramic insert (76) is located at the distal end of needle assembly (28) while second ceramic insert (78) is located at the proximal end of needle assembly (28). As shown in FIG. 25, over-molded portion (80) provides a needle assembly (28) having a dual lumen configuration with an axial lumen (82) and a lateral lumen (84). First ceramic insert (76) includes holes (86) that permit communication between lateral lumen (84) and axial lumen (82). Alternatively, thermoplastic and ceramic components may be combined in a variety of other ways to provide a needle (42).

Figure 29:
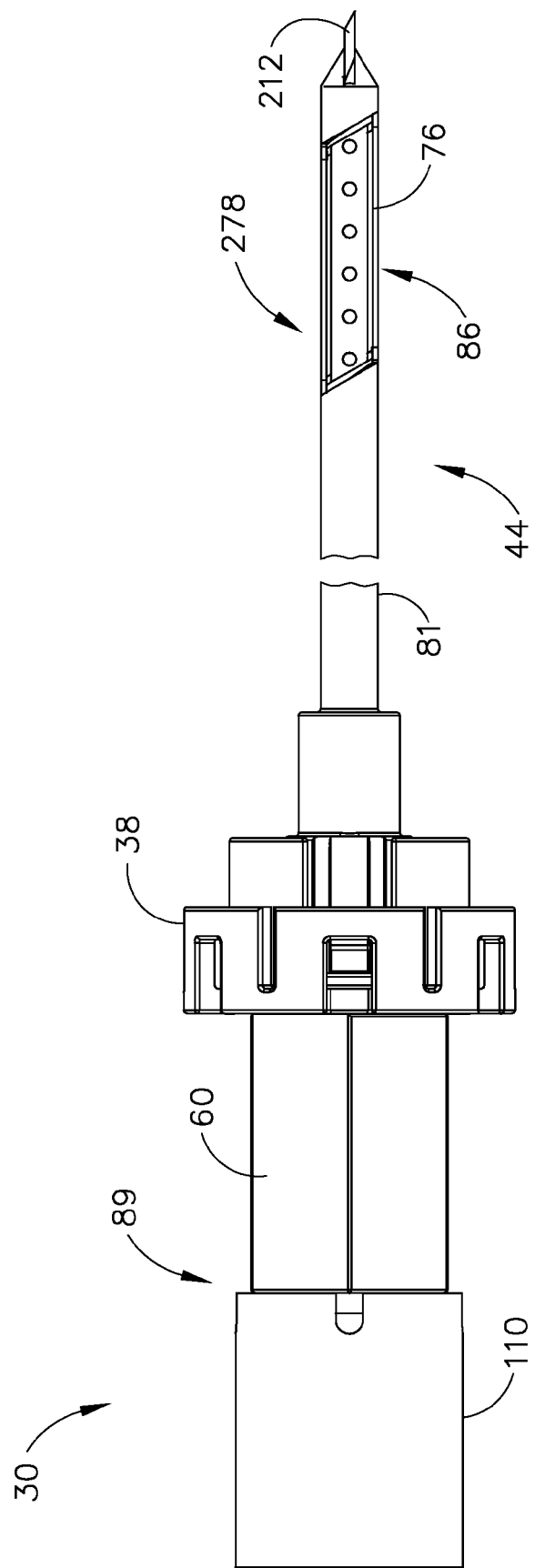
FIG. 29 depicts a top view of the needle assembly of FIG. 28.

FIGS. 29, 30, and 32 show another exemplary needle (44) design for use in a needle assembly (30). Needle (44) includes a first ceramic insert (76) having holes (86) for communication between an axial lumen (82) and a lateral lumen (84). Needle (44) further includes an over-molded portion (81) including a mounting portion (60) at the proximal end. The substantial over-molded portion (81) in needle (44) may aid in reducing needle deflection in some settings.

It should be understood that the above examples of needles (42, 44) are merely illustrative. Needles (42, 44) may have any other suitable features, components, or configurations to reduce deflection while maintaining imaging ability. Alternatively, needles (42, 44) may lack features, components, or configurations to reduce deflection. Similarly, needles (42, 44) may be non-imageable if desired. By way of example only, needles (42, 44, 46) may be configured in accordance with the teachings of U.S. Pub. No. 2008/0195066, entitled "Revolving Tissue Sample Holder For Biopsy Device," published Aug. 14, 2008, the disclosure of which is incorporated by reference herein. Other suitable features, components, configurations, or properties for needles (42, 44, 46) will be apparent to those of ordinary skill in the art in view of the teachings herein.

3. Exemplary Fluid Sealing and Vacuum Arrangement

With a detachable needle assembly (28, 29, 30, 134, 160, 161), another aspect to address may concern fluid sealing and vacuum arrangement. FIGS. 23-27, 12, 13, and 58 show an exemplary fluid sealing and vacuum arrangement for a needle assembly (28, 29). Needle assembly (28, 29) of this example includes thumbwheel (36, 206), needle (42), and needle hub (88). Needle hub (88) further includes a mounting portion (48), a telescopic sleeve (90), and a telescopic sleeve spring (92). When a probe assembly (14, 18, 19) is attached to needle hub (88), telescopic sleeve (90) moves longitudinally against telescopic sleeve spring (92). This movement of telescopic sleeve (90) exposes the fluid sealing and vacuum arrangement mechanisms of needle hub (88) as discussed in more detail below. When probe assembly (14, 18, 19) is removed from needle assembly (28, 29), sleeve (90) may spring back to a proximal position, under the bias of spring (92).

Figure 4:
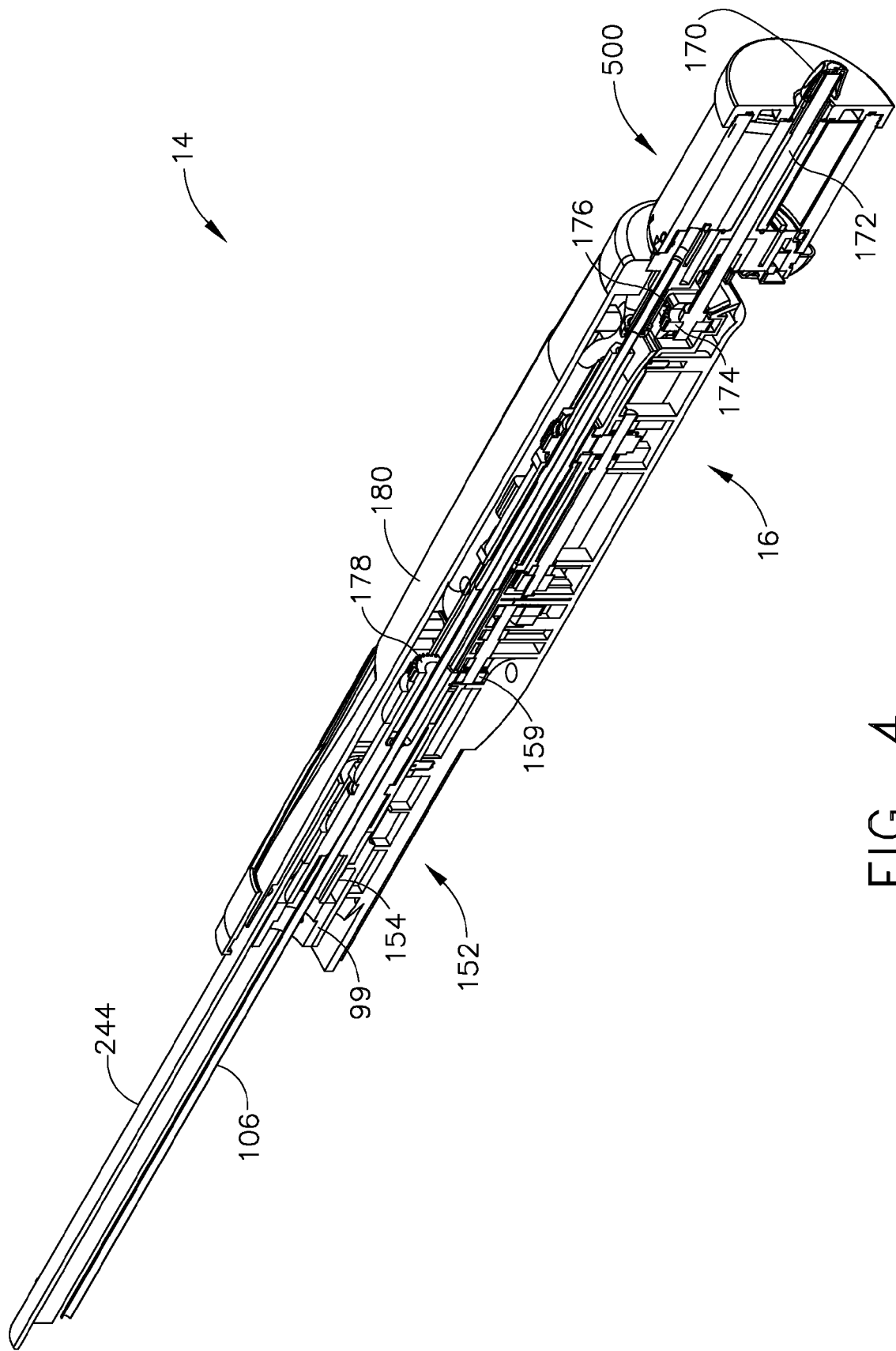
FIG. 4 depicts a perspective, cross-sectional view of the probe assembly and holster assembly of the MRI biopsy device of FIG. 1.
Figure 5:
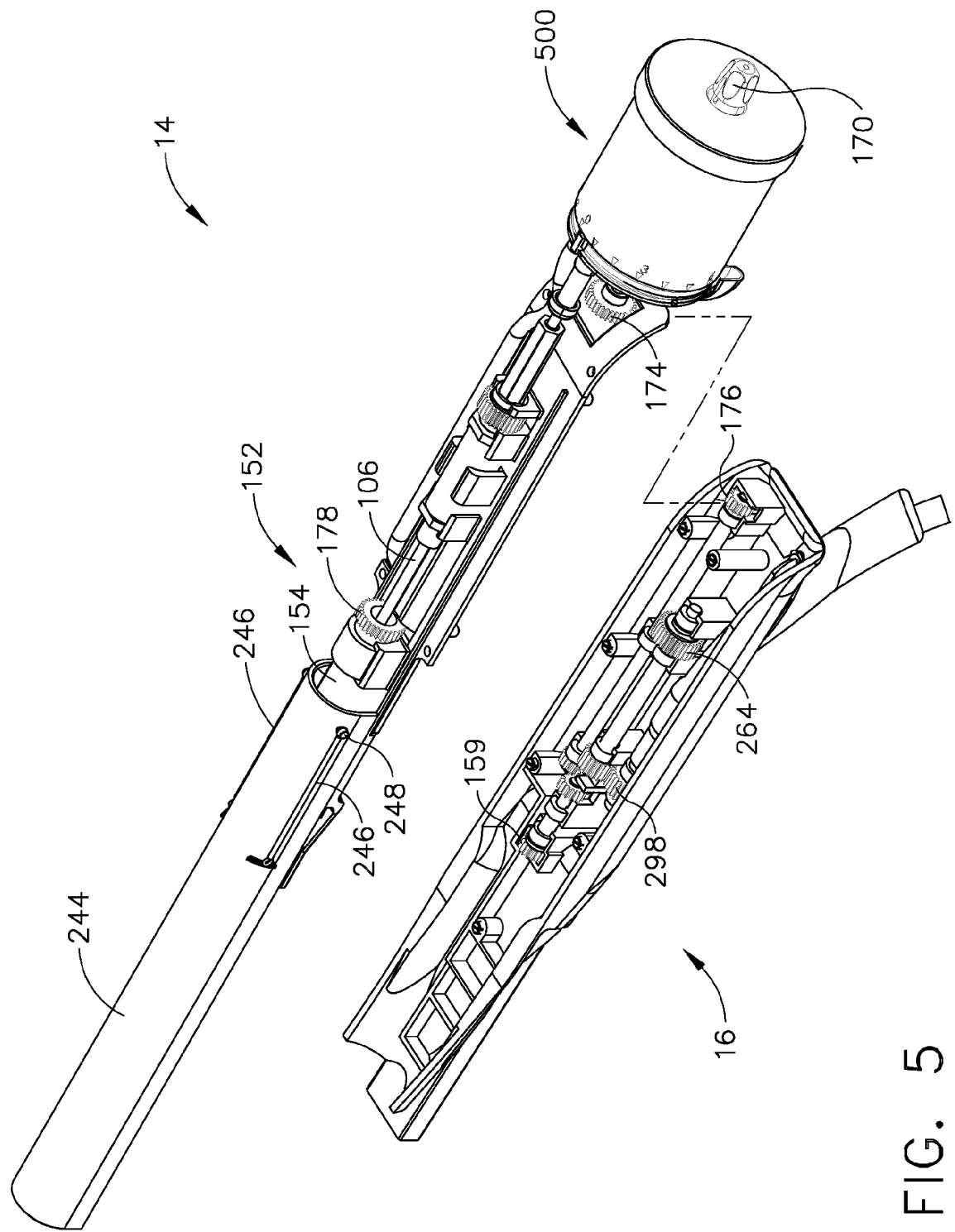
FIG. 5 depicts a perspective view of the probe assembly and holster assembly of the MRI biopsy device of FIG. 1, showing the probe assembly separate from the holster assembly, and having the holster plate removed to expose internal components of the holster assembly, and the probe casing and locking cover removed to expose internal components of the probe assembly.
Figure 6:
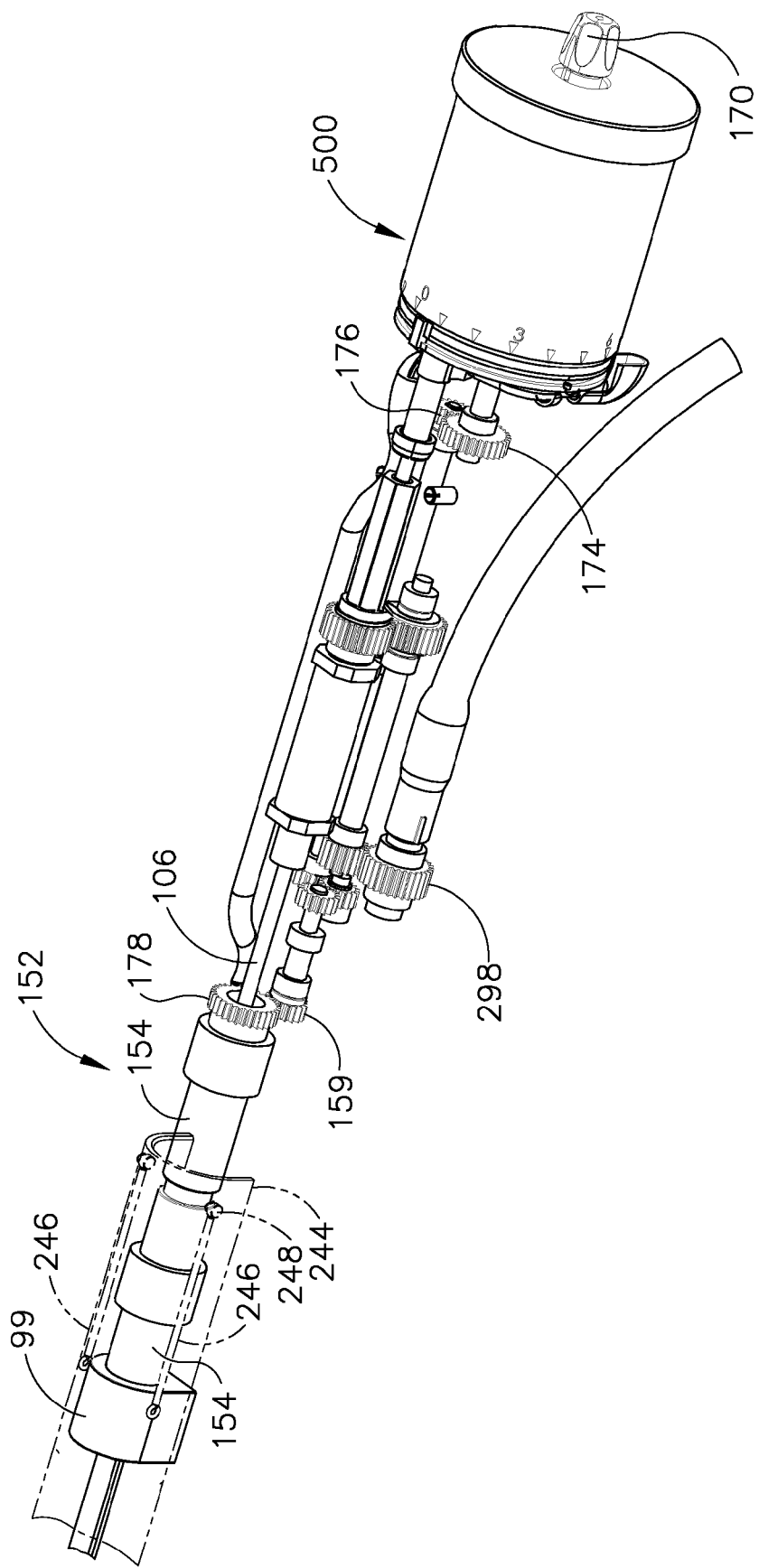
FIG. 6 depicts a perspective view of the internal components of the probe assembly and holster assembly of the MRI biopsy device of FIG. 1.
Figure 58:
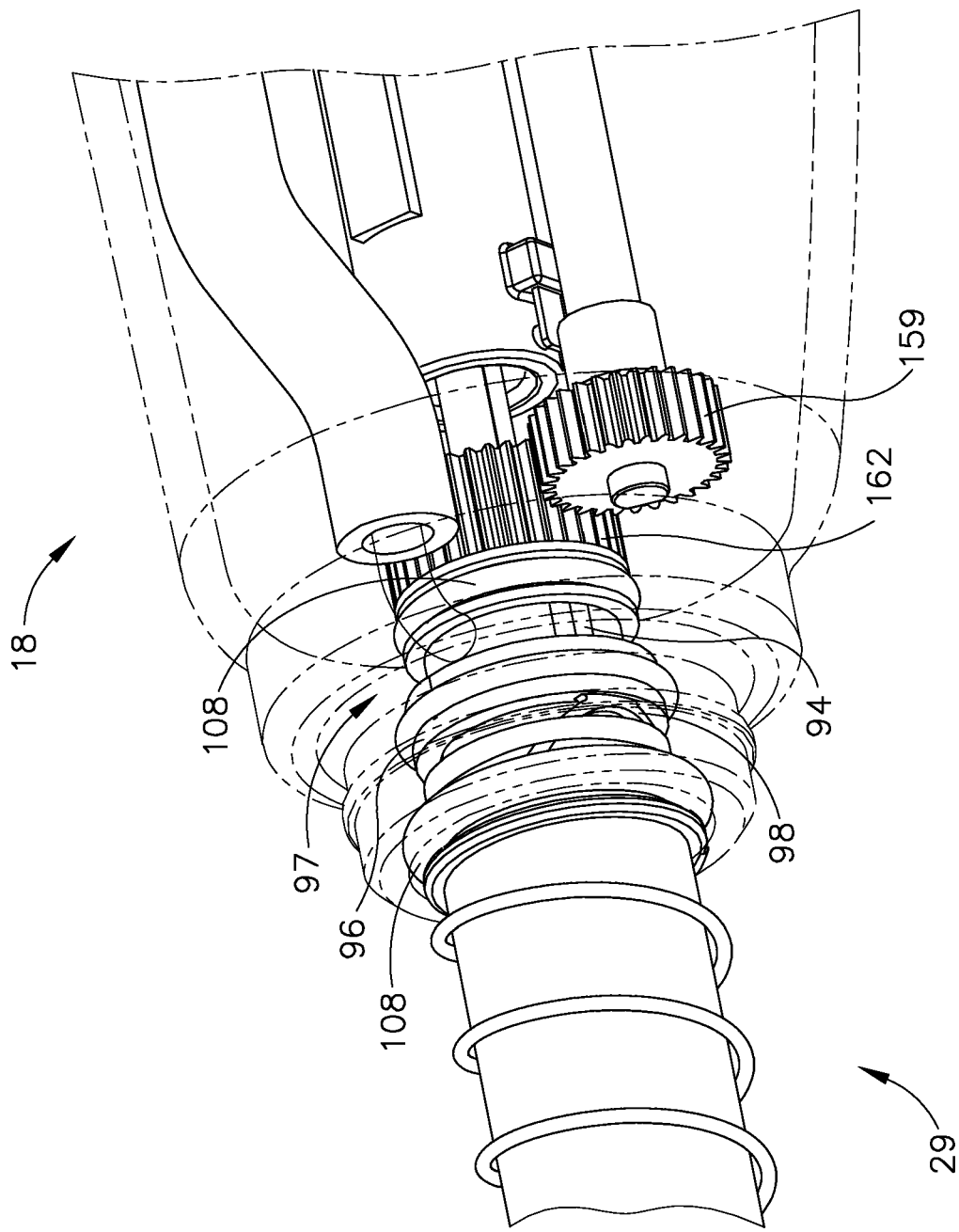
FIG. 58 depicts a partial perspective view, in partial transparency, of the probe assembly of FIG. 12, showing fluid sealing and vacuum delivery mechanisms.

As shown in FIGS. 23-27, and 58, the fluid sealing and vacuum arrangement mechanisms are components of mounting portion (48) in this example. Mounting portion (48) includes a lateral port (94) for communicating with lateral lumen (84) of needle (42). A slide cover (96) is provided to avoid fluid leakage from lateral port (94). Slide cover (96) has a pair of thin protruding members (98) that act as springs to bias lateral port (94) in a closed position when probe assembly (14, 18, 19) is detached from needle assembly (28, 29). As shown in FIGS. 4, 6, and 58, when probe assembly (14, 18, 19) is attached to needle assembly (28, 29), a vacuum manifold (97, 99, 101) of probe assembly (14, 18, 19) pushes against slide cover (96), which moves distally along mounting portion (48) to expose lateral port (94). Lateral port (94) is shown exposed in FIG. 27. Vacuum manifold (97, 99, 101) is thus in fluid communication with lateral lumen (84) of needle (42) via lateral port (94) when probe assembly (14, 18, 19) is coupled with needle assembly (28, 29). As shown in FIGS. 24-27 and 58, vacuum manifold o-rings (108) prevent vacuum loss by providing a seal between vacuum manifold (97, 99, 101) and mounting portion (48). It should be understood that lateral lumen (84) may be used in accordance with any of the teachings in U.S. Pub. No. 2008/0195066, entitled "Revolving Tissue Sample Holder For Biopsy Device," published Aug. 14, 2008, the disclosure of which is incorporated by reference herein, or in any other suitable fashion.

Mounting portion (48) of the present example also includes an axial port (100) for communicating with the axial lumen (82) of needle (42). A cup seal (102) is provided over axial port (100) to prevent fluid leakage. A cutter entry cone (104) may also be provided over cup seal (102). When probe assembly (14, 18, 19) is attached to needle assembly (28, 30) as will be described in greater detail below, a cutter (106, 107) of probe assembly (14, 18, 19) may enter axial port (100) through the cutter entry cone (104) and the cup seal (102) makes an opening for cutter (106, 107) via a slit (not shown) in cup seal (102). Alternatively, cup seal (102) may be initially formed with or as a puncturable membrane (e.g., without a slit or other opening in it), such that cutter (106, 107) breaks the membrane when advanced into needle assembly (28, 30) for the first time upon coupling of probe assembly (14, 18, 19) with needle assembly (28, 30).

FIGS. 29-32 and 59 show an exemplary fluid sealing and vacuum arrangement mechanism incorporated into another needle assembly (30). Needle assembly (30) of this example includes a thumbwheel (38), needle (44), and needle hub (89). Needle hub (89) includes a mounting portion (60), fixed sleeve (110), and other features for controlling connections to axial lumen (82) and lateral lumen (84) of needle (44). For instance, a lateral fluid seal (112) is used for avoiding fluid leakage from lateral lumen opening (114), while an axial fluid seal assembly (116) is used for avoiding fluid leakage through axial lumen opening (118). Axial fluid seal assembly (116) comprises an o-ring (120) positioned around axial lumen opening (118) of needle (44), and a hollow cap member (122) that is positioned over axial lumen opening (118) and contacts o-ring (120) to create a seal with the needle (44). A sealing member (124) is fitted inside hollow cap member (122), followed by a spacer (126), a cup seal (128), and a cover member (130).

When a probe assembly (14, 18, 19) is attached to needle hub (89), fixed sleeve (110) sits over a vacuum manifold (97, 99, 101) of probe assembly (14, 18, 19). For instance, and as shown in FIG. 59, vacuum manifold (101) may include protruding members (103) that open lateral fluid seal (112) for establishing fluid communication from vacuum manifold (101) to lateral lumen (84) through lateral lumen opening (114). Also, when probe assembly (14, 18, 19) is attached to needle hub (89), cutter (106, 107) passes through a slit (not shown) in cup seal (128) and into axial lumen (82). Again, though, as noted above, cutter (106, 107) may instead form its own opening through cup seal (128), such that cup seal need not necessarily have a slit or other opening before cutter (106, 107) is advanced through cup seal (128). As shown in FIGS. 30-32 and 59, manifold o-rings (132) are provided to prevent fluid leakage with the vacuum manifold (101) to needle assembly (30) connection.

Figure 38:
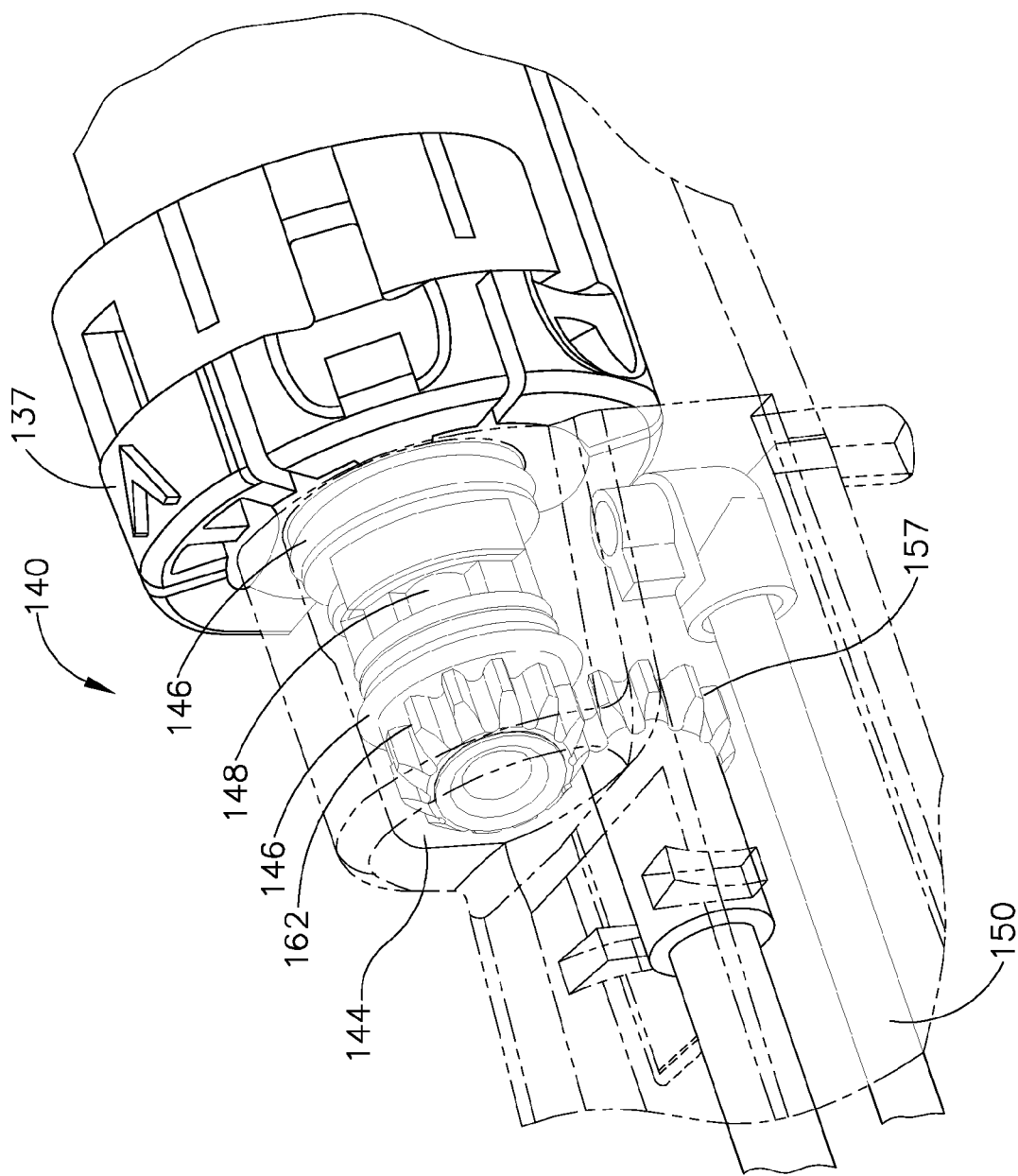
FIG. 38 depicts a perspective view, in partial transparency, of the needle assembly of FIG. 35, coupled with a probe assembly, and showing gear engagement of the two assemblies.
Figure 39:
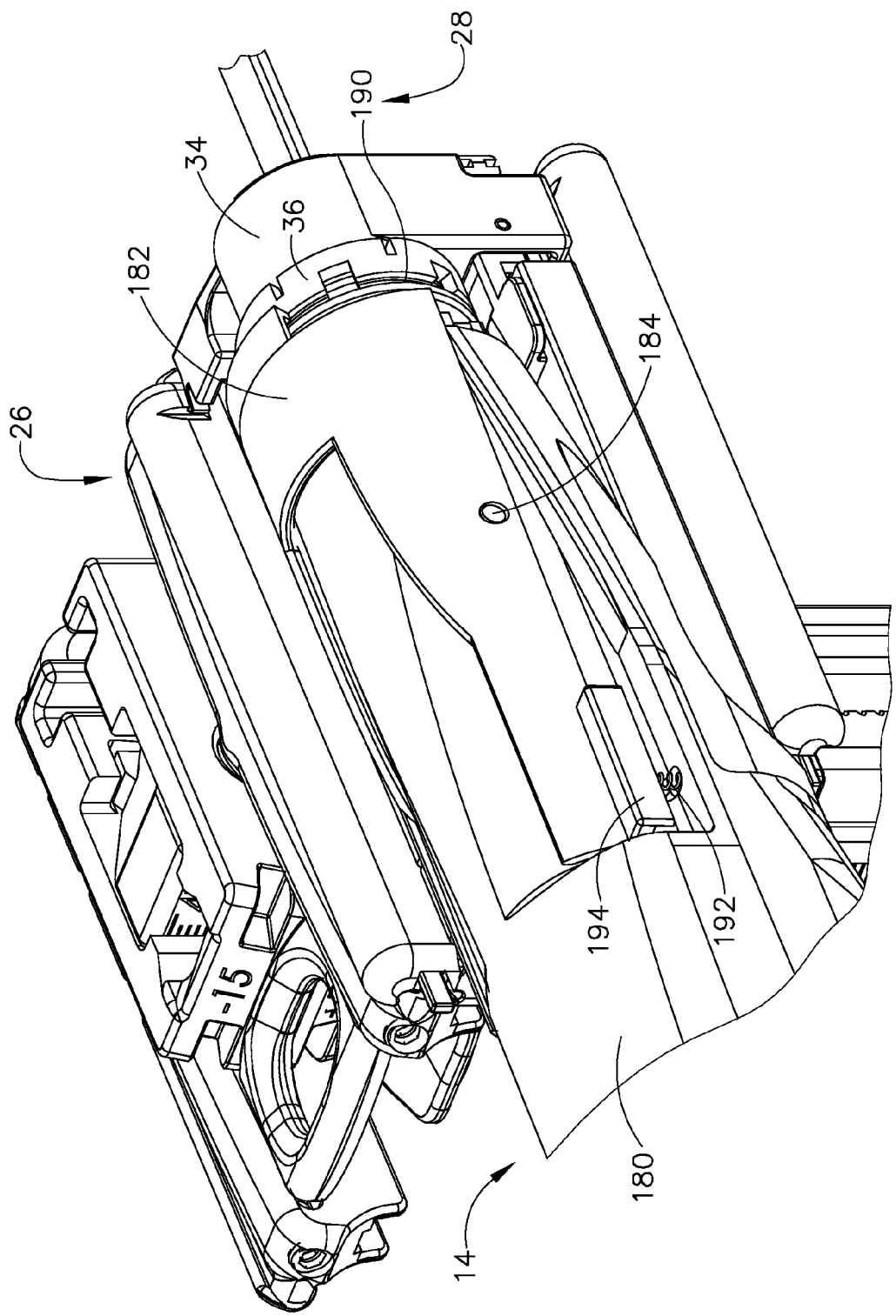
FIG. 39 depicts a partial perspective view of the MRI biopsy device of FIG. 1, showing the probe locking cover for attachment of the probe assembly to the needle assembly.
Figure 40:
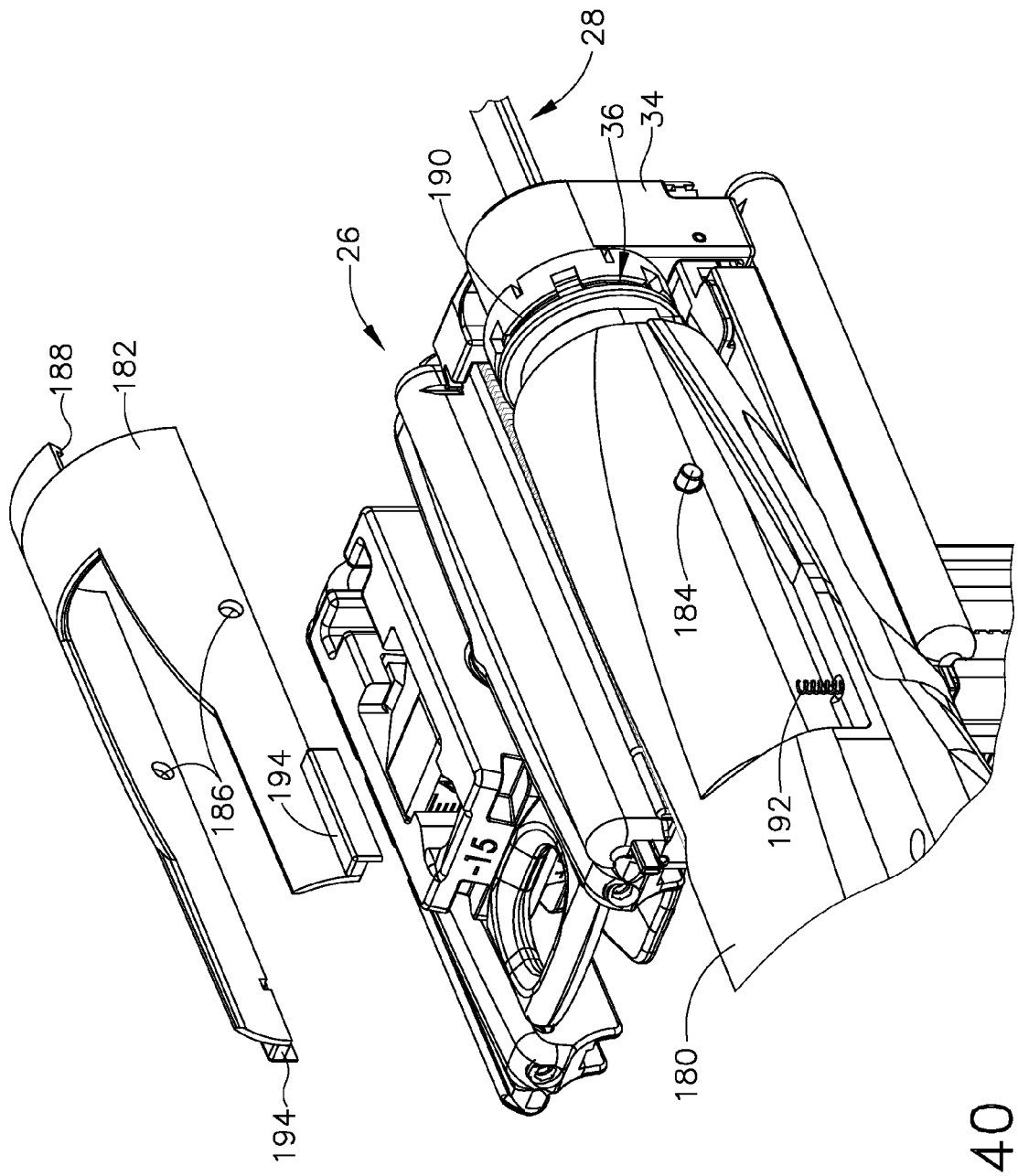
FIG. 40 depicts a partially exploded perspective view of the MRI biopsy device of FIG. 39, showing the probe locking cover, pivot pin, and springs.
Figure 41:
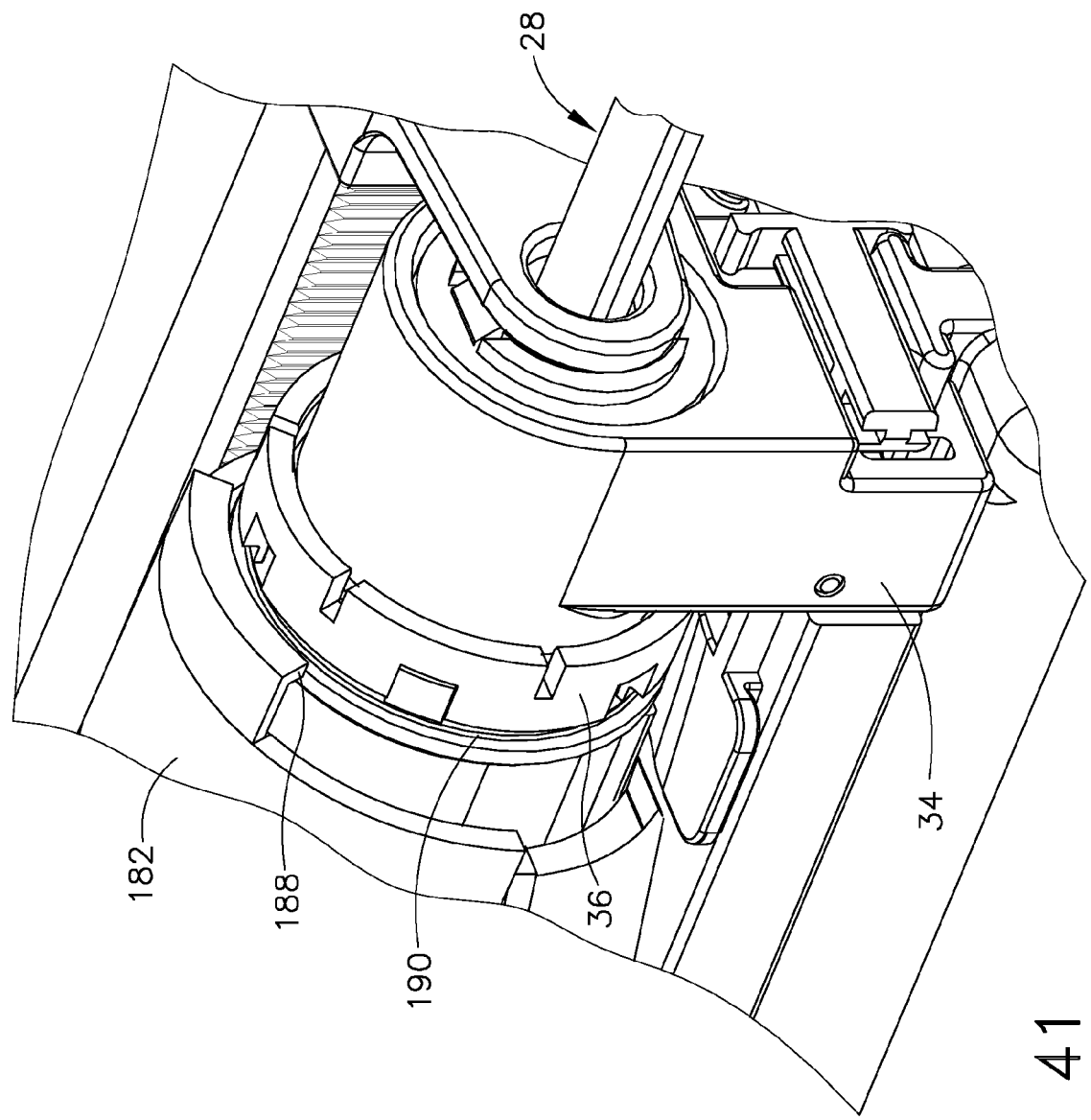
FIG. 41 depicts a partial perspective view of the MRI biopsy device of FIG. 39, showing engagement between the annular groove on the thumbwheel and an engaging member on the probe locking cover.

FIGS. 35-38 show another exemplary fluid sealing and vacuum arrangement mechanism incorporated into a needle assembly (134). Needle assembly (134) of this example includes a needle hub (136) and modified thumbwheel (138). To connect a probe assembly (140) to needle assembly (134), modified thumbwheel (138) has openings (142) that receive distally extending connecting members (not shown) of probe assembly (140), such as to provide a "snap fit" between probe assembly (140) and needle assembly (134). For instance, probe assembly (140) may include a thumbwheel grip (137) (FIG. 38) that has such distally extending connecting members that provide a snap fit with openings (142) of thumbwheel (138). As shown in FIG. 38, a vacuum manifold (144) of probe assembly (140) fits over a proximal portion of needle hub (136) to fluidly communicate with lateral lumen (84). In particular, needle hub (136) includes a slot (148) for communicating vacuum to lateral lumen (84) from a vacuum line (150) of probe assembly (140) that is coupled with vacuum manifold (144). Needle hub (136) includes o-rings (146) for preventing vacuum loss when a probe assembly (140) is attached to needle assembly (134). As is also shown in FIG. 38, coupling probe assembly (140) with needle assembly provides engagement of needle indexing drive gear (157) with needle indexing gear (162), as will be described in greater detail below.

4. Exemplary Needle Indexing

Another aspect to address with a detachable needle assembly (28, 29, 30, 134, 160, 161) design may include indexing of needle (42, 44, 64). For instance, needle indexing may include rotation of needle (42, 44, 64) to orient aperture (278) at various angular positions about the longitudinal axis defined by needle (42, 44, 54). Such multiple orientations may be desirable, by way of example only, to obtain a plurality of tissue samples from a biopsy site, without requiring needle (42, 44, 64) to be removed from the patient during the acquisition of such a plurality of tissue samples. An illustrative example of such rotation and acquisition of multiple tissue samples is disclosed in U.S. Pat. No. 5,526,822, the disclosure of which is incorporated by reference herein. Other ways in which multiple tissue samples may be obtained at various locations will be apparent to those of ordinary skill in the art in view of the teachings herein.

FIGS. 3-6, 8, 10, 26, and 46 show exemplary indexing mechanism components that incorporate a hexagonal interface for indexing needles such as needles (42, 44) shown in FIGS. 22-31. This approach provides removable coupling between a needle indexing drive assembly and needle (42, 44) itself, to facilitate a detachable needle assembly design. As shown in FIGS. 3-6, 8, 10 and 46, a needle indexing drive assembly (152) is located on probe assembly (14, 19). Needle indexing drive assembly (152) of this example includes a drive shaft (154) having a hollow hexagonal cross-section. Drive shaft (154) is rotatable relative to manifold (99).

Needle assembly (28) of FIGS. 22-27, which may be used with a probe assembly (14, 19) having a drive shaft (154) as described above and as shown in FIGS. 3-6 and 9-11, includes a hexagonal-shaped indexing portion (49). When probe assembly (14, 19) is coupled with needle assembly (28), indexing portion (49) of the needle assembly (28) fits within the hollow hexagonal space of drive shaft (154). Drive shaft (154) is configured for rotational movement, as described in greater detail below, such that when drive shaft (154) rotates, needle assembly (28) rotates concomitantly therewith.

Figure 13:
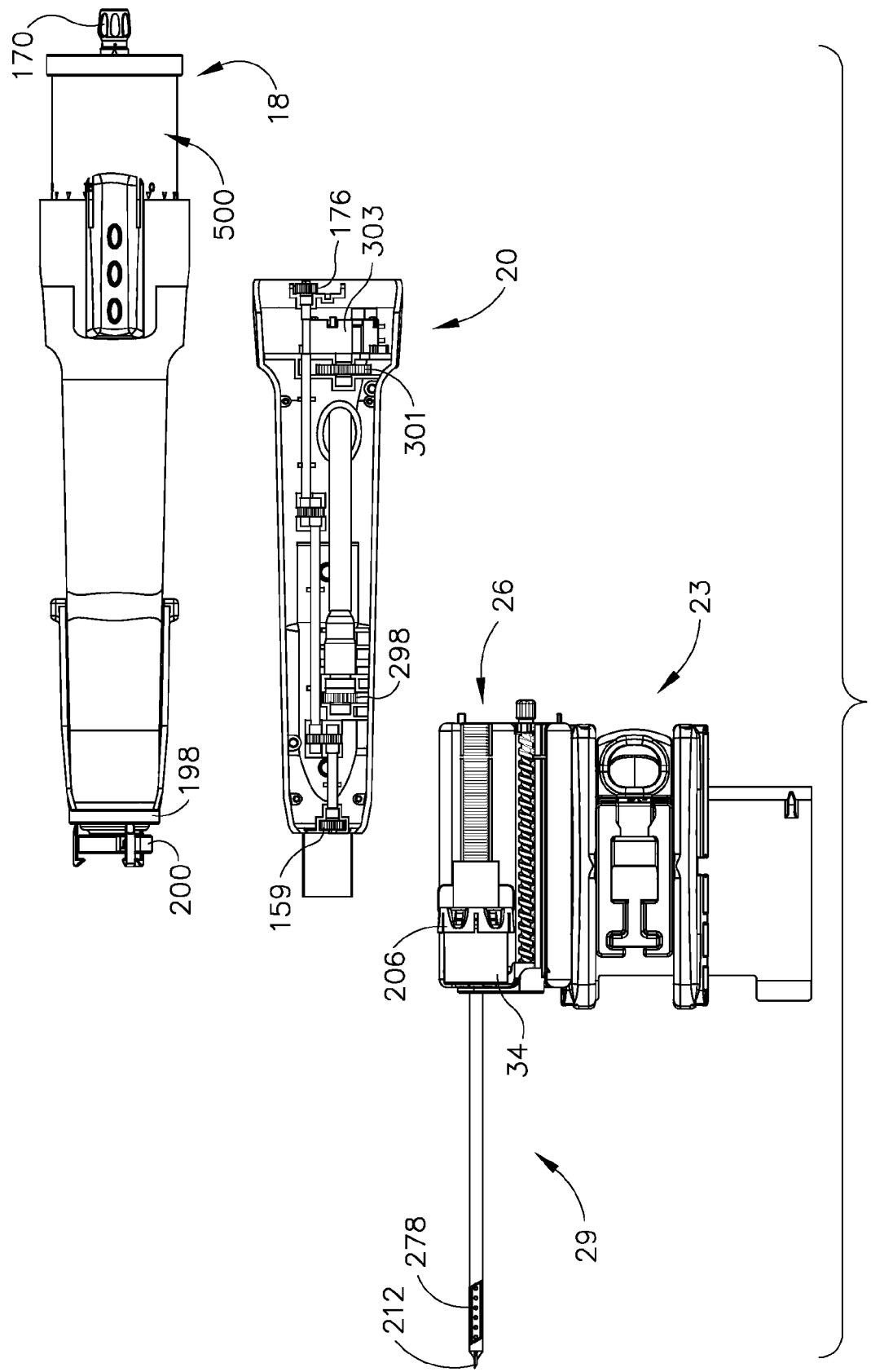
FIG. 13 depicts a partially exploded top view of the MRI biopsy device of FIG. 12, showing the holster assembly with holster plate removed, probe assembly, and targeting set assembly separate from one another.
Figure 14:
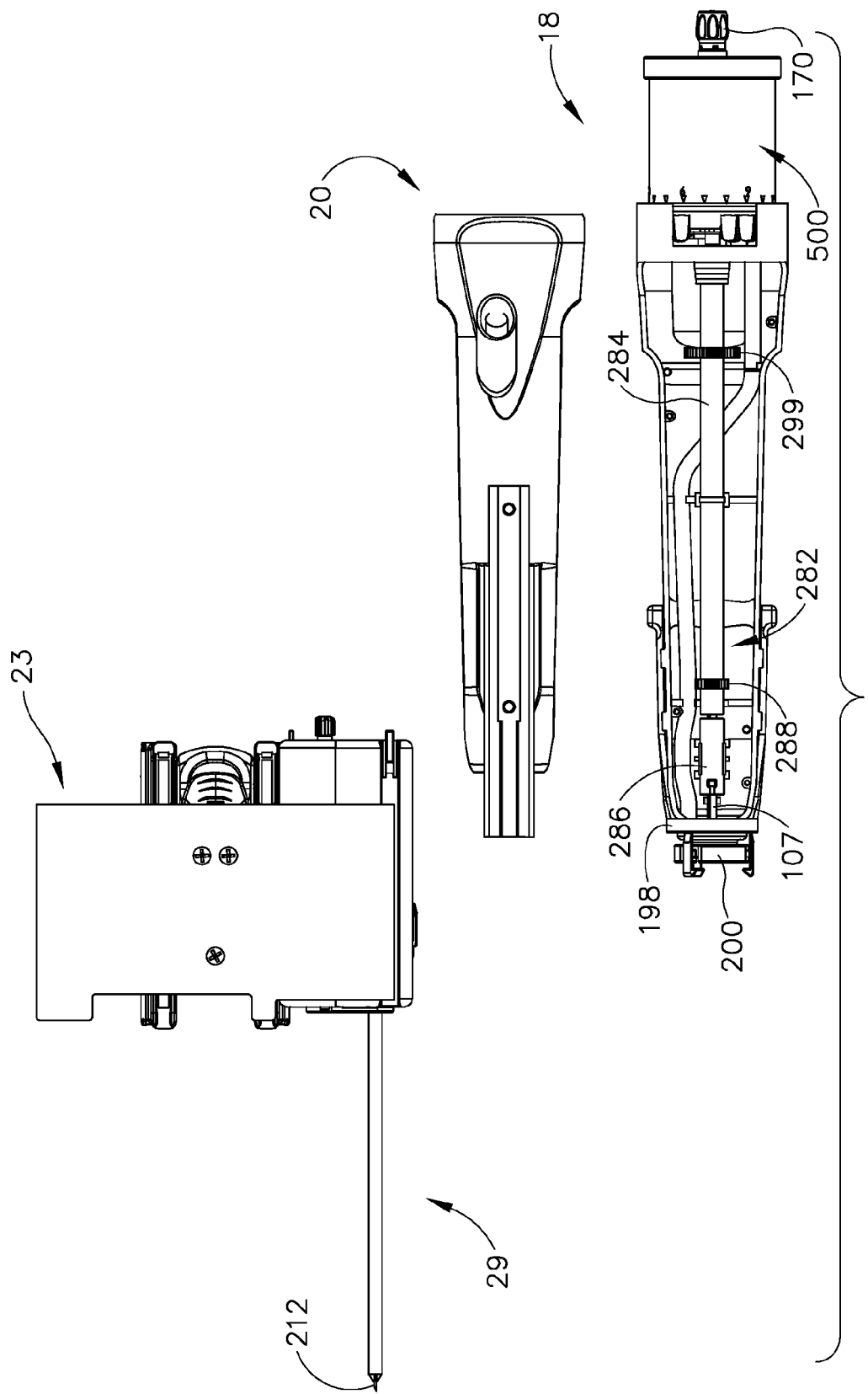
FIG. 14 depicts a partially exploded bottom view of the MRI biopsy device of FIG. 12, showing the holster assembly, probe assembly with probe plate removed, and targeting set assembly separate from one another.
Figure 33:
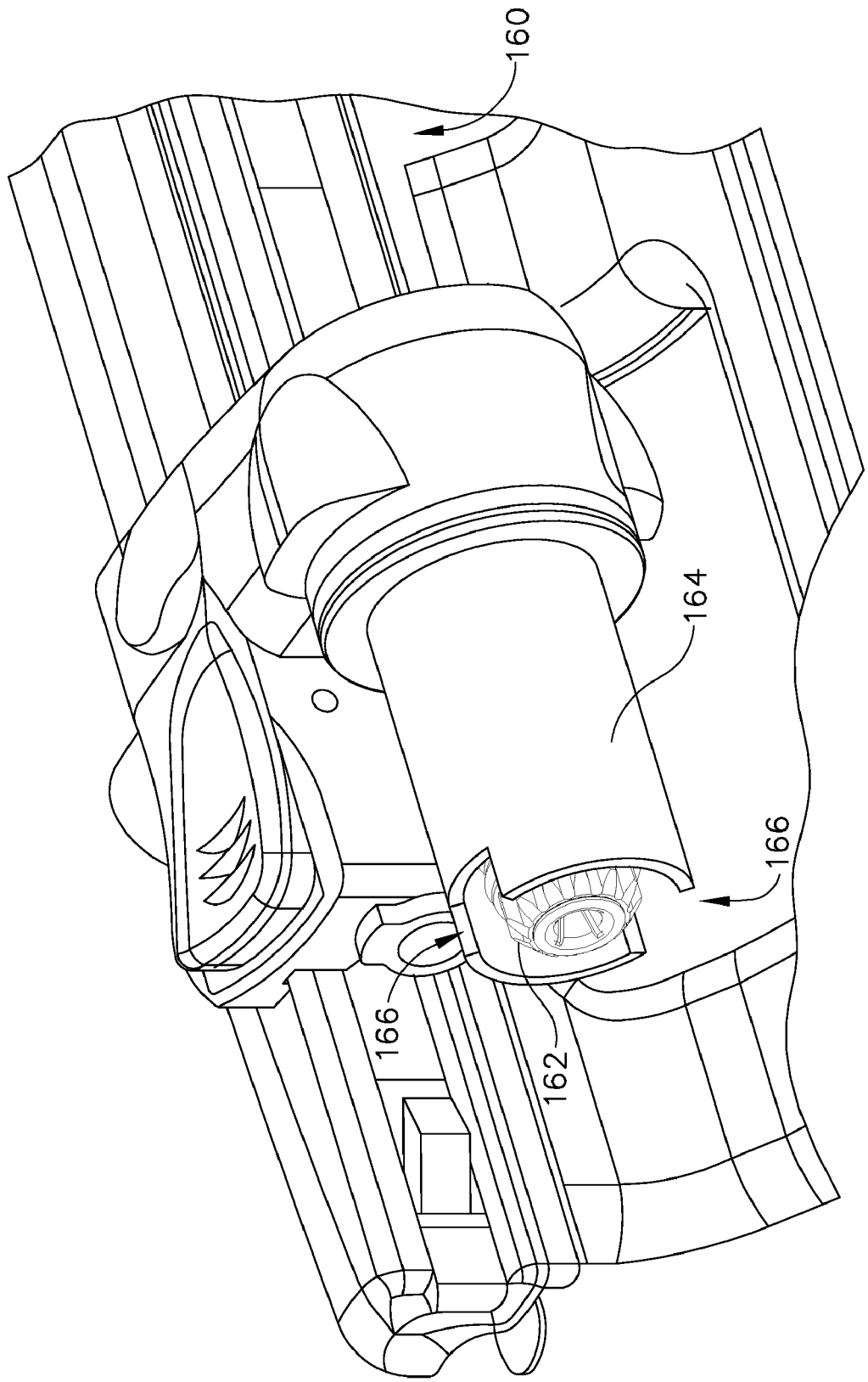
FIG. 33 depicts a perspective view of the proximal end of another exemplary needle assembly, having a sleeve cover with access openings for gear engagement.
Figure 34:
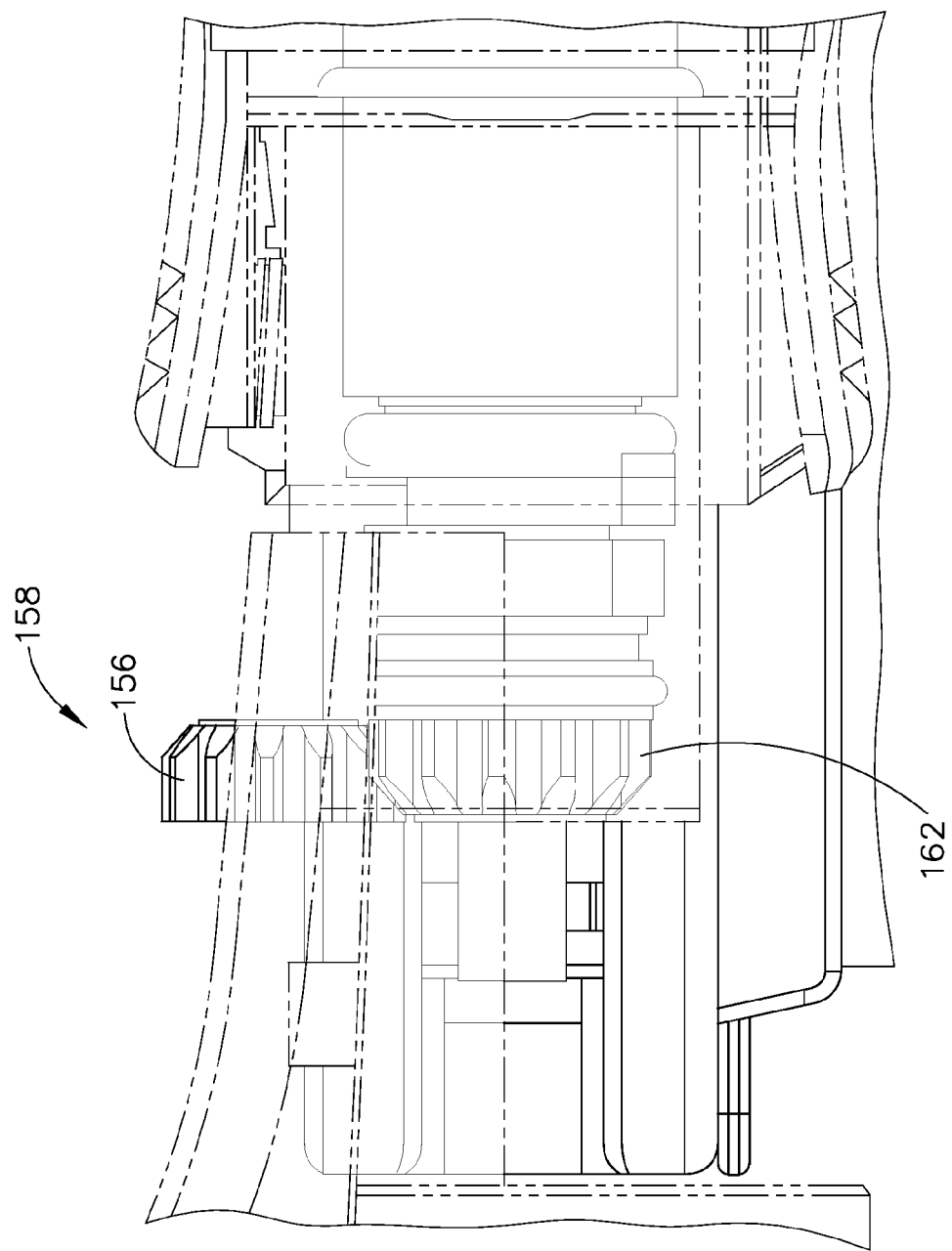
FIG. 34 depicts a side view of the proximal end of the needle assembly of FIG. 33, coupled with a probe assembly and showing gear engagement of the two assemblies.
Figure 35:
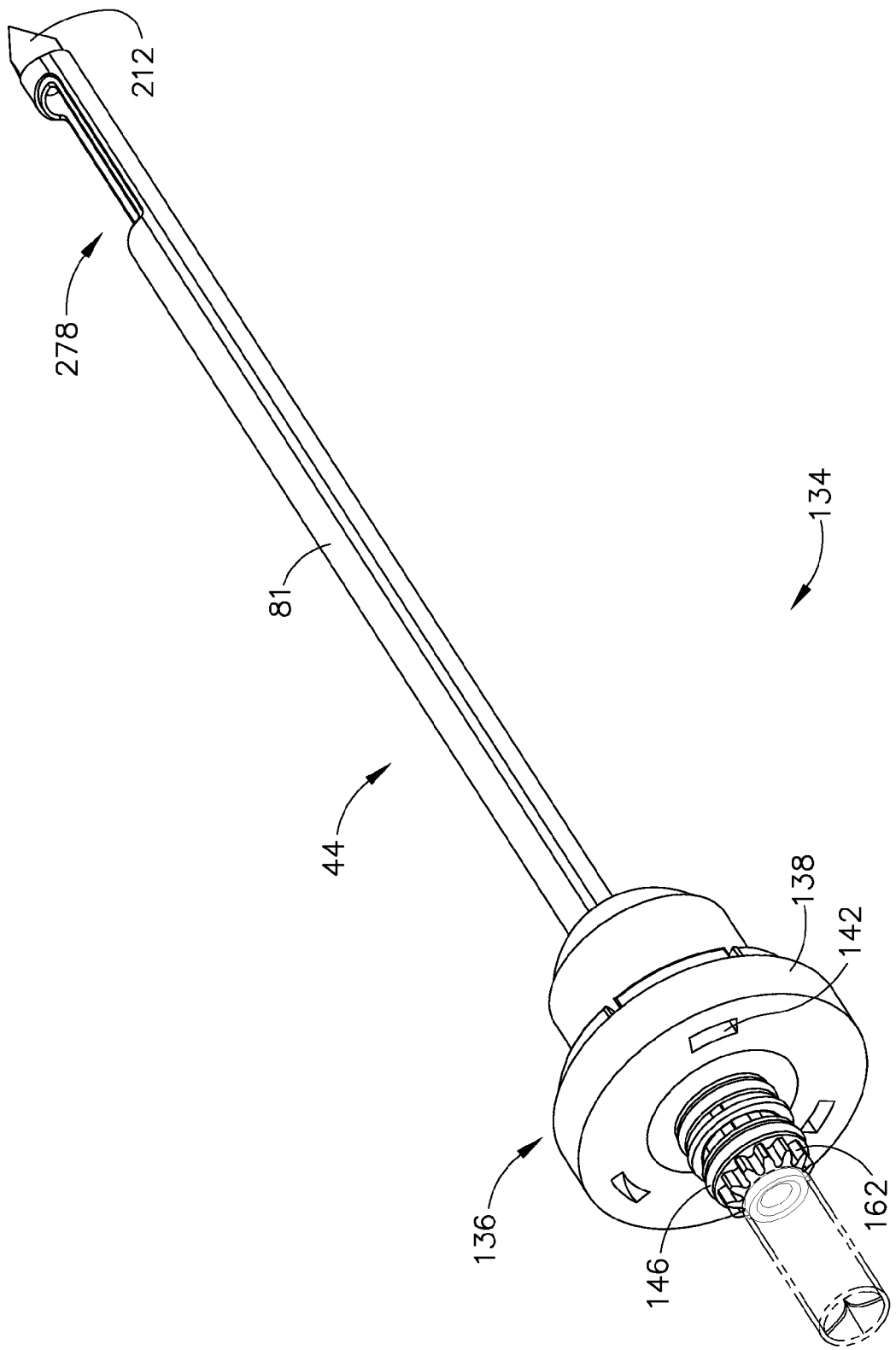
FIG. 35 depicts a perspective view of the proximal end of another exemplary needle assembly, having a modified thumbwheel.
Figure 36:
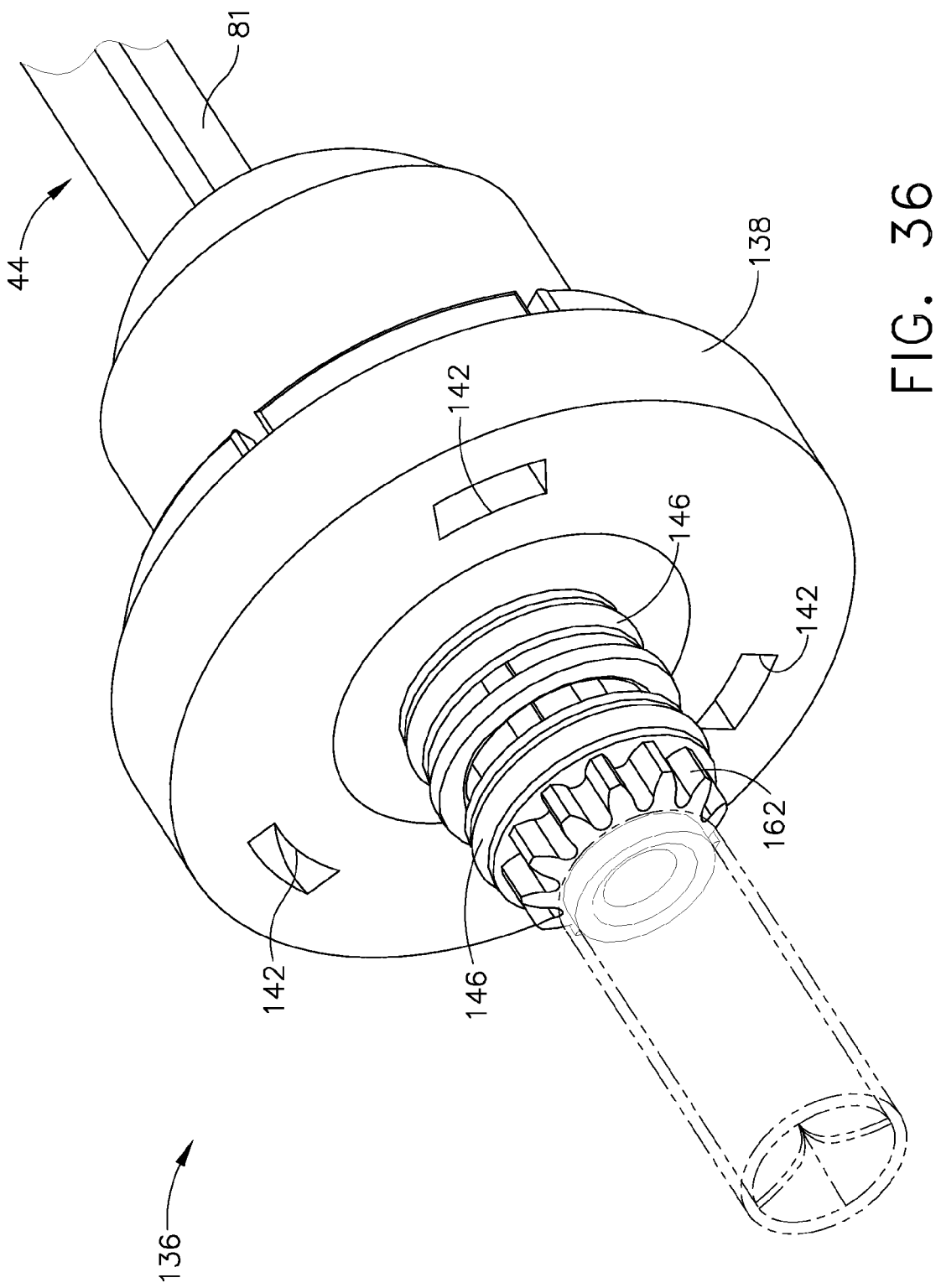
FIG. 36 depicts a partial perspective view of the thumbwheel of FIG. 35, showing a flexible membrane at the proximal-most end and a gear for indexing the needle.
Figure 37:
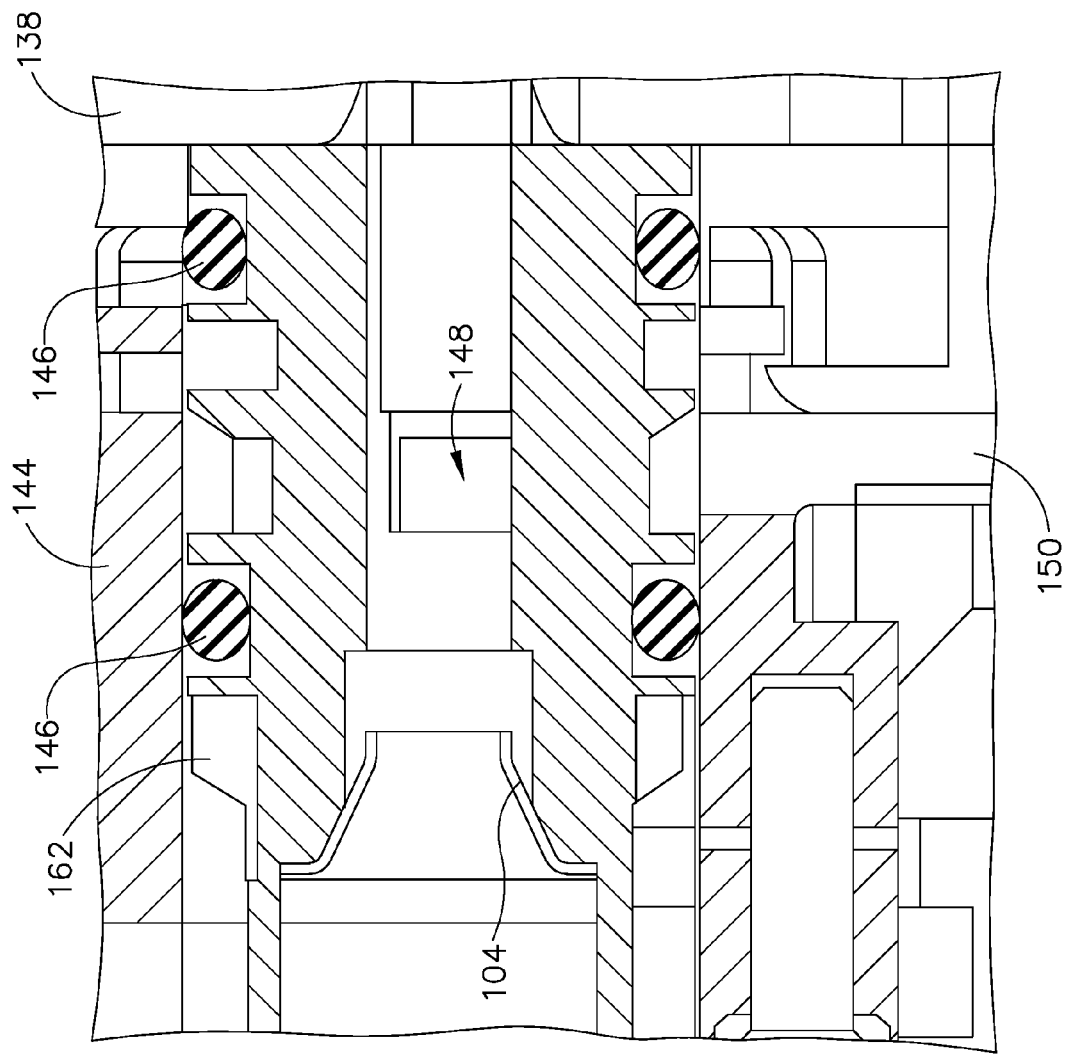
FIG. 37 depicts a cross-sectional view of the thumbwheel of FIG. 35.

FIGS. 33-36, 38, 48-49, and 58 show other exemplary needle indexing mechanisms that incorporate a gear interface for indexing. This approach provides removable coupling between a needle indexing drive gear (156, 157) and a needle indexing gear (162), to facilitate a detachable needle assembly design. As shown in FIGS. 34 and 38, needle indexing drive gear (156, 157) may be located on probe assembly (158, 140), and may be driven manually, pneumatically, by motor, or in any suitable fashion. In some other versions, needle indexing drive gear (159) may be located on holster assembly (20) as shown in FIG. 13 and 58. As shown in FIGS. 33-36, 38, 48-49, and 58, needle assembly (28, 29, 30, 134, 160, 161) includes a needle indexing gear (162). When probe assembly (158, 140, 65), and/or probe assembly (18) with holster assembly (20), is connected to needle assembly (134, 160, 161, 29), needle indexing gear (162) aligns with needle indexing drive gear (156, 157, 159). Needle indexing drive gear (156, 157, 159) is configured for rotational movement, as described in greater detail below, such that when the needle indexing drive gear (156, 157, 159) rotates, needle assembly (29, 134, 160, 161) rotates concomitantly therewith.

FIGS. 33-34 further show an exemplary needle assembly (160) having a modified sleeve (164) to allow a needle indexing gear (162) to engage a needle indexing drive gear (156) of probe assembly (158) while protecting the fluid sealing and vacuum arrangement mechanisms described above. As shown in FIG. 33, modified sleeve (164) has access openings (166) on the top and bottom to allow a needle indexing drive gear (156) to communicate with needle indexing gear (162). In particular, and as shown in FIG. 34, needle indexing drive gear (156) of probe assembly (158) may communicate directly with needle indexing gear (162).

Figure 47:
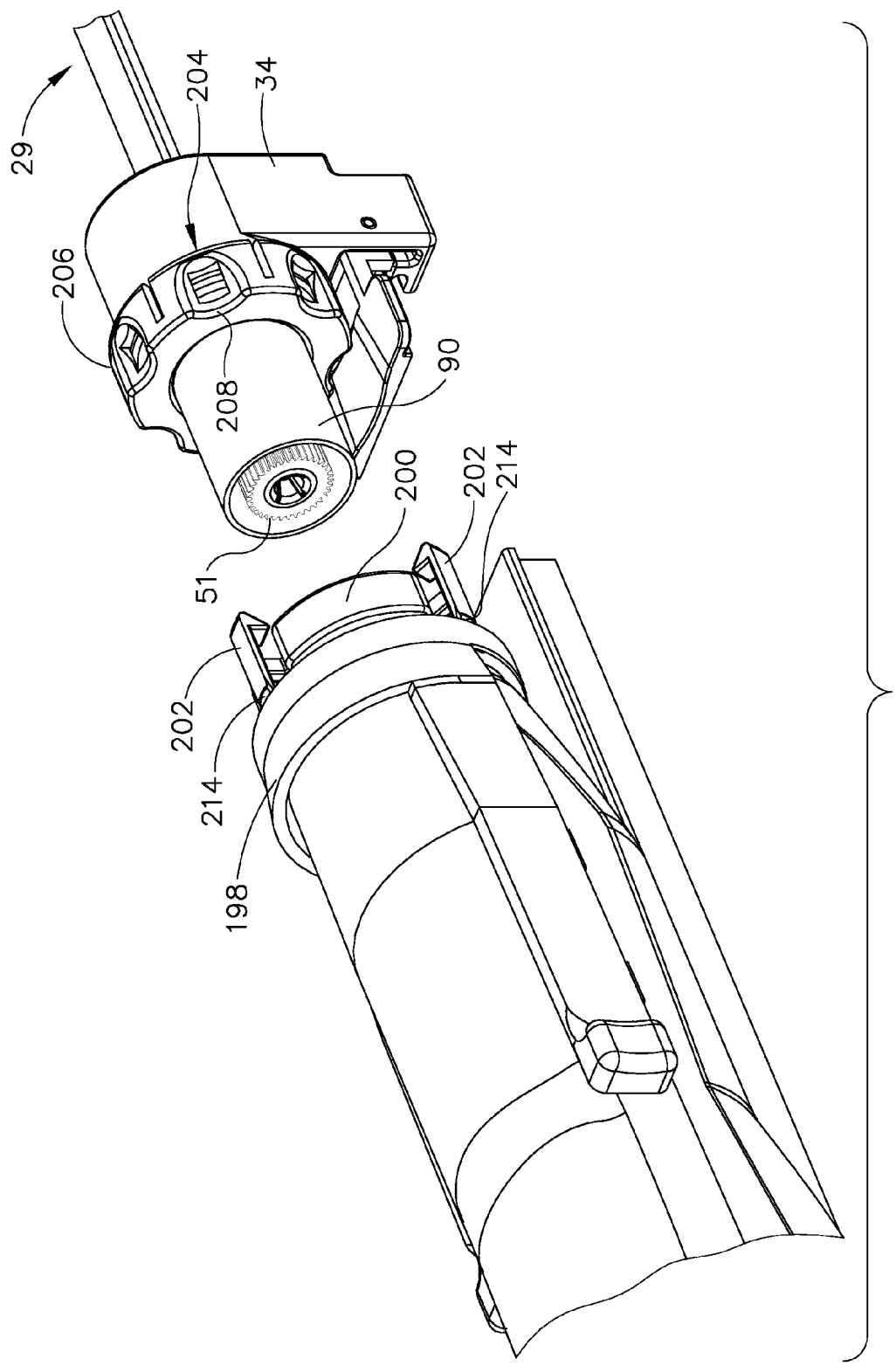
FIG. 47 depicts a partial exploded perspective view of the device of FIG. 44, showing the probe assembly detached from the needle assembly.

In other versions, a needle indexing gear (51) such as the one shown in FIG. 47 engages with a complementary splined socket (not shown) of a needle indexing drive shaft within a probe that couples with needle portion (29). Gear engagement may thus be internal-external, side-by-side, or of any other suitable type.

Figure 7:
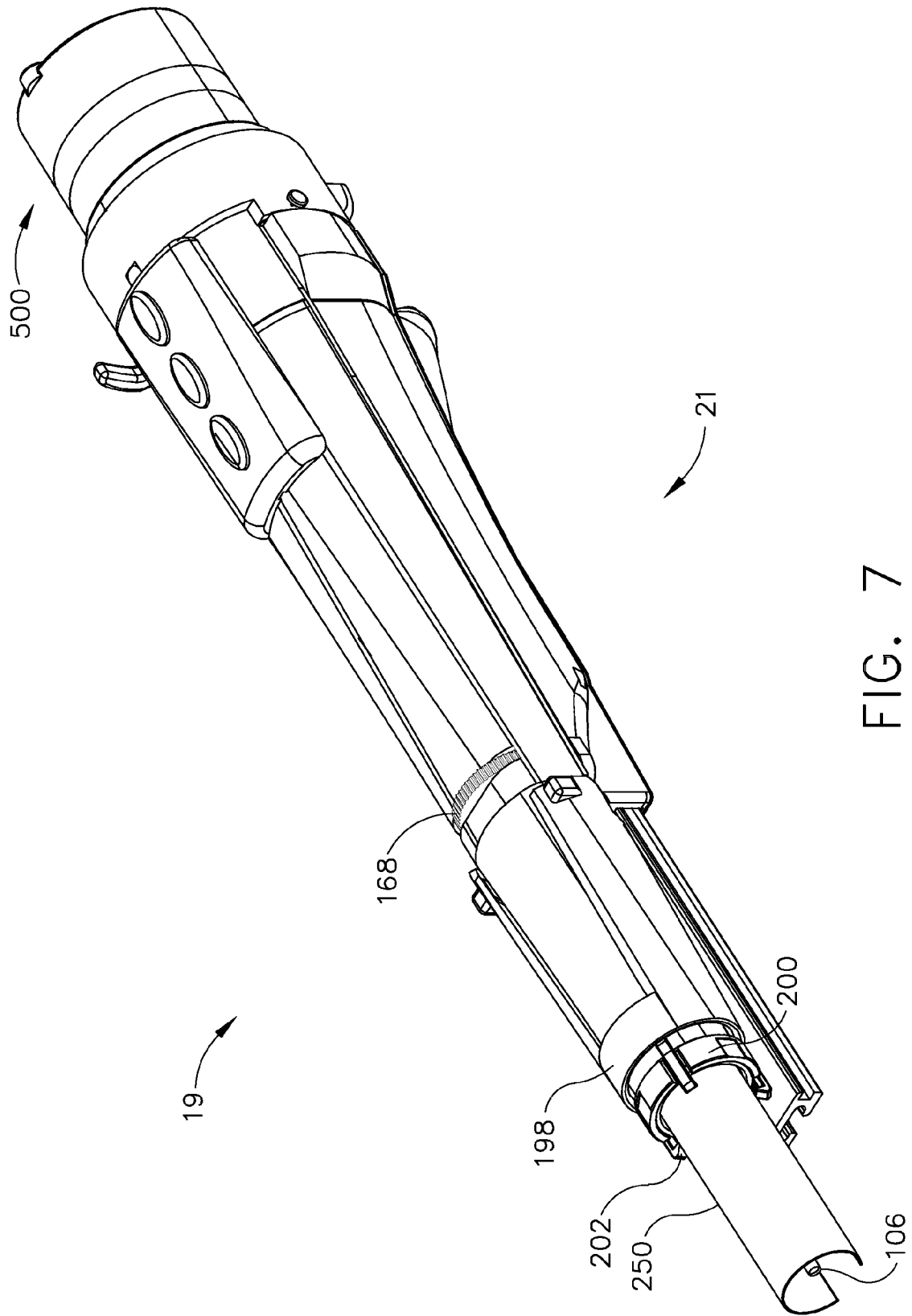
FIG. 7 depicts a perspective view of another exemplary MRI biopsy device showing a holster assembly, probe assembly, and keypad.

Now turning to the modes for actuating the needle indexing drive mechanisms, FIG. 7 shows an exemplary configuration where needle indexing drive gear (168) is partially exposed (e.g., as a manually operable thumbwheel) through the exterior housing of probe assembly (19). In this configuration, an operator may manually rotate needle indexing drive gear (168) to index an attached needle assembly. In one example, the partially exposed needle indexing drive gear (168) is positioned along a central portion of probe assembly (19), as shown in FIG. 7. By way of example only, needle indexing drive gear (168) may be configured and operated in accordance with the teachings of U.S. Non-Provisional patent application Ser. No. 12/337,942, entitled "TISSUE BIOPSY DEVICE WITH CENTRAL THUMBWHEEL," filed on even date herewith, now published as U.S. Pat. Pub. No. 2010/0160819, the disclosure of which is incorporated by reference herein. For instance, needle indexing drive gear (168) may be analogized to the central thumbwheel described in that patent application. Of course, a partially exposed needle indexing drive gear (168) may be provided in any other suitable fashion and in any other suitable location(s).

Figure 15:
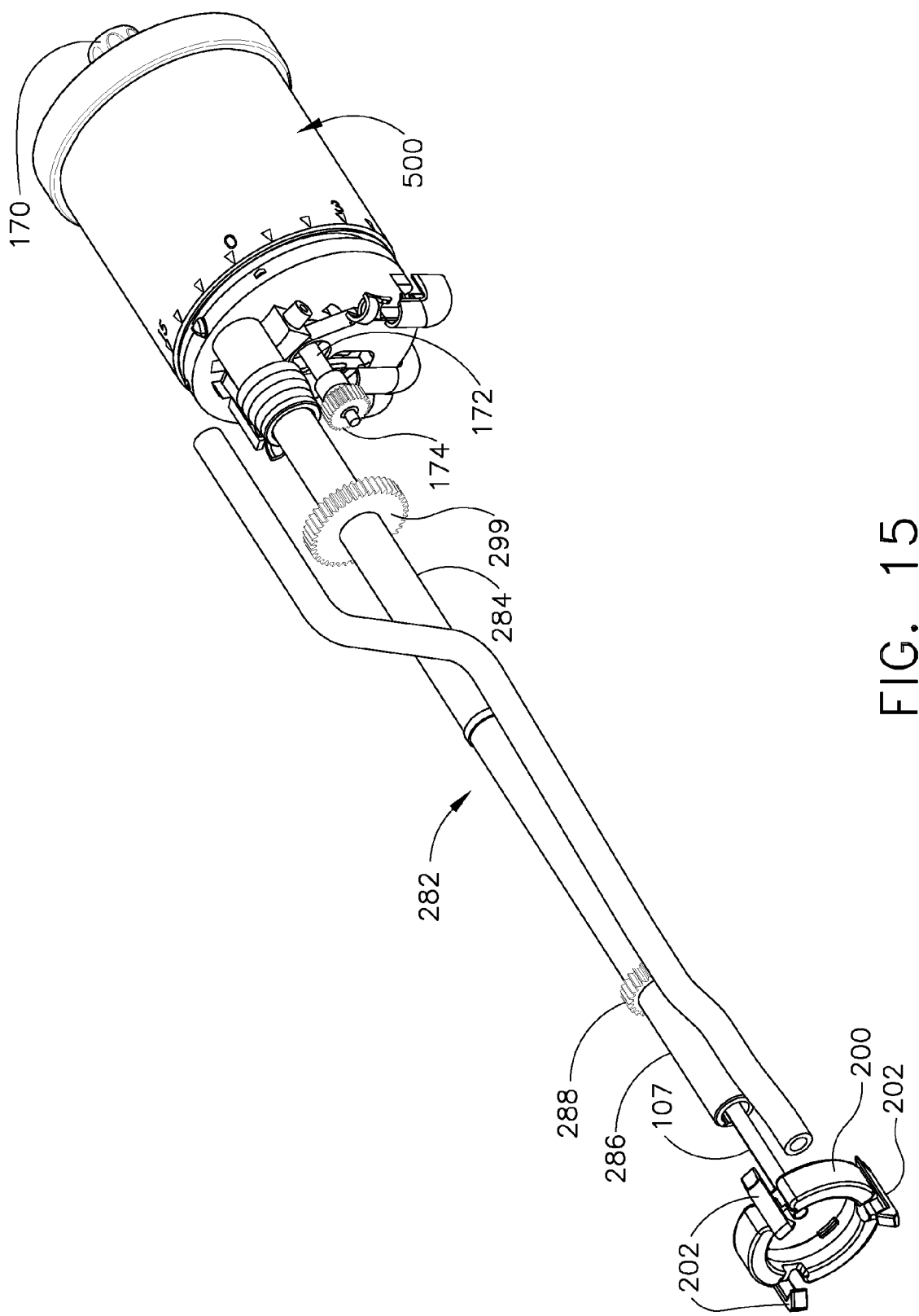
FIG. 15 depicts a perspective view of the probe assembly of FIG. 12, with the casing, annular ring, and keypad removed to show the vacuum tube and the cutter rotation and translation mechanism.
Figure 16:
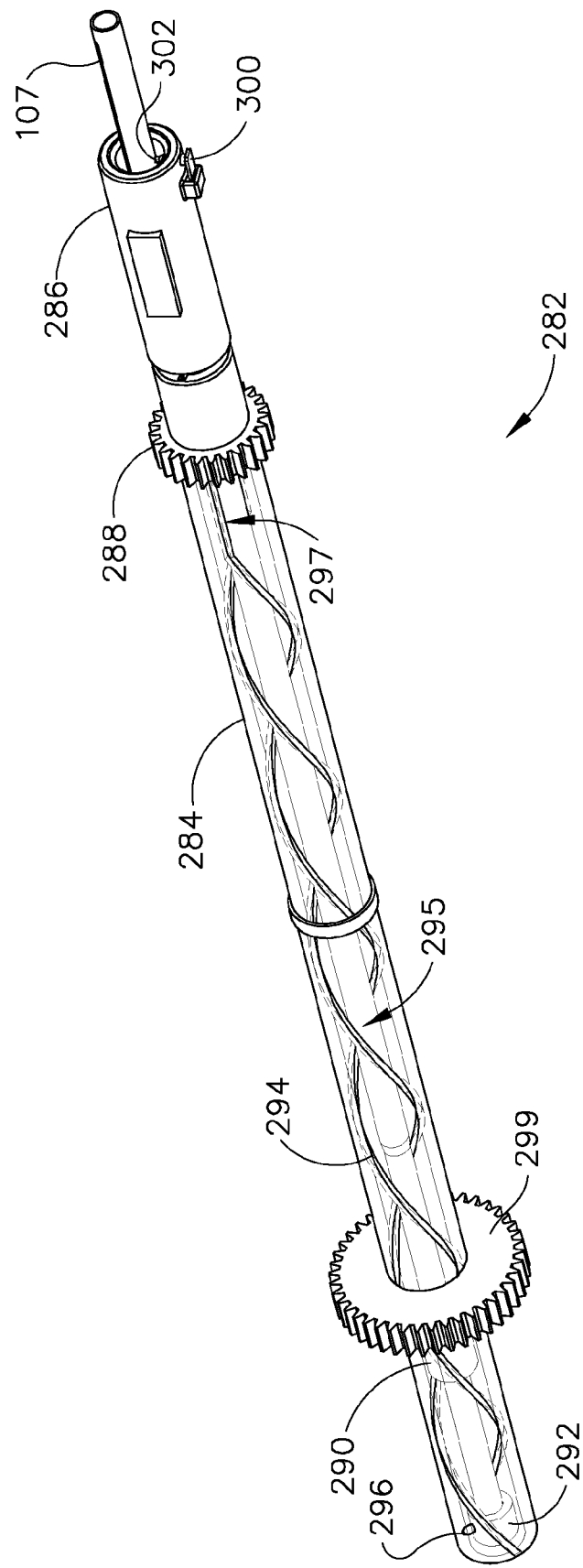
FIG. 16 depicts a partial perspective view of the cutter rotation and translation mechanism of the probe assembly of FIG. 12.
Figure 17:
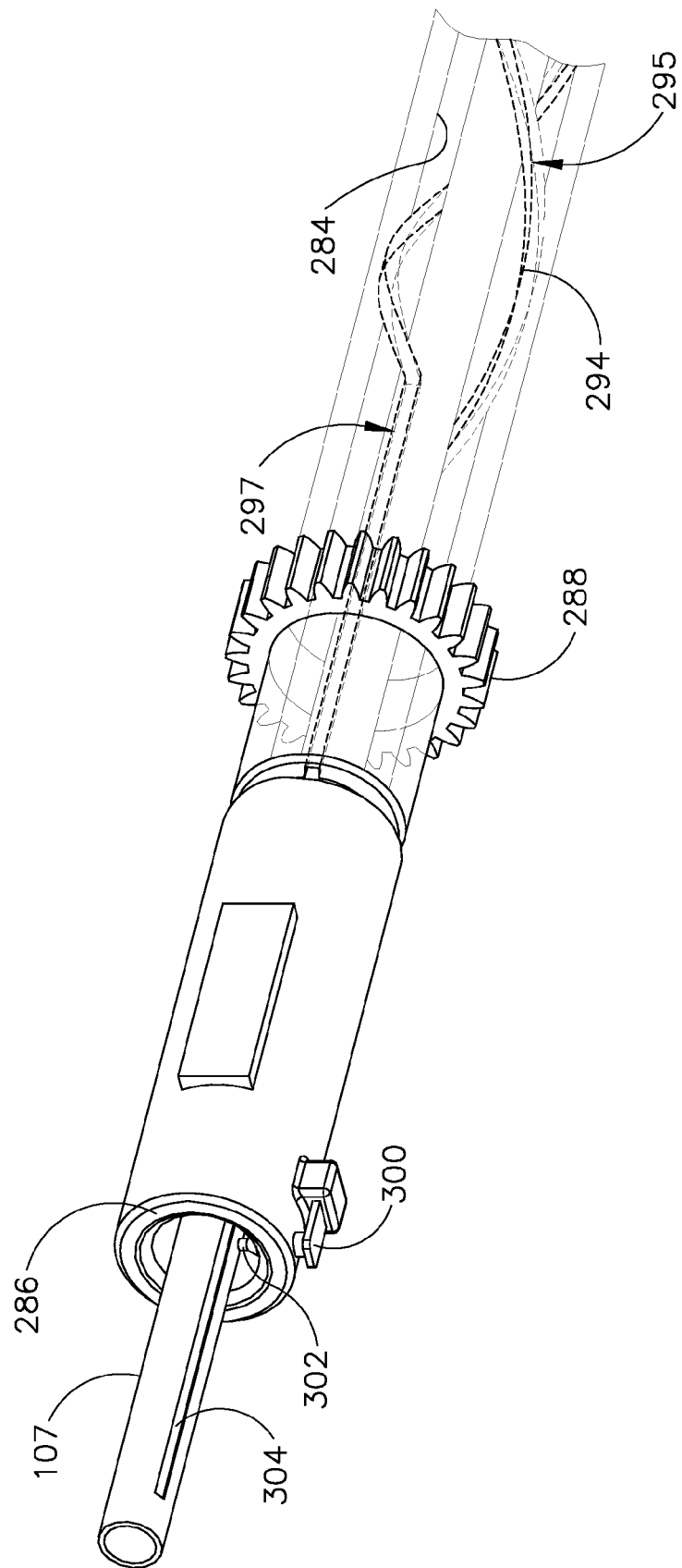
FIG. 17 depicts another partial perspective view of the cutter rotation and translation mechanism of the probe assembly of FIG. 12.
Figure 18:
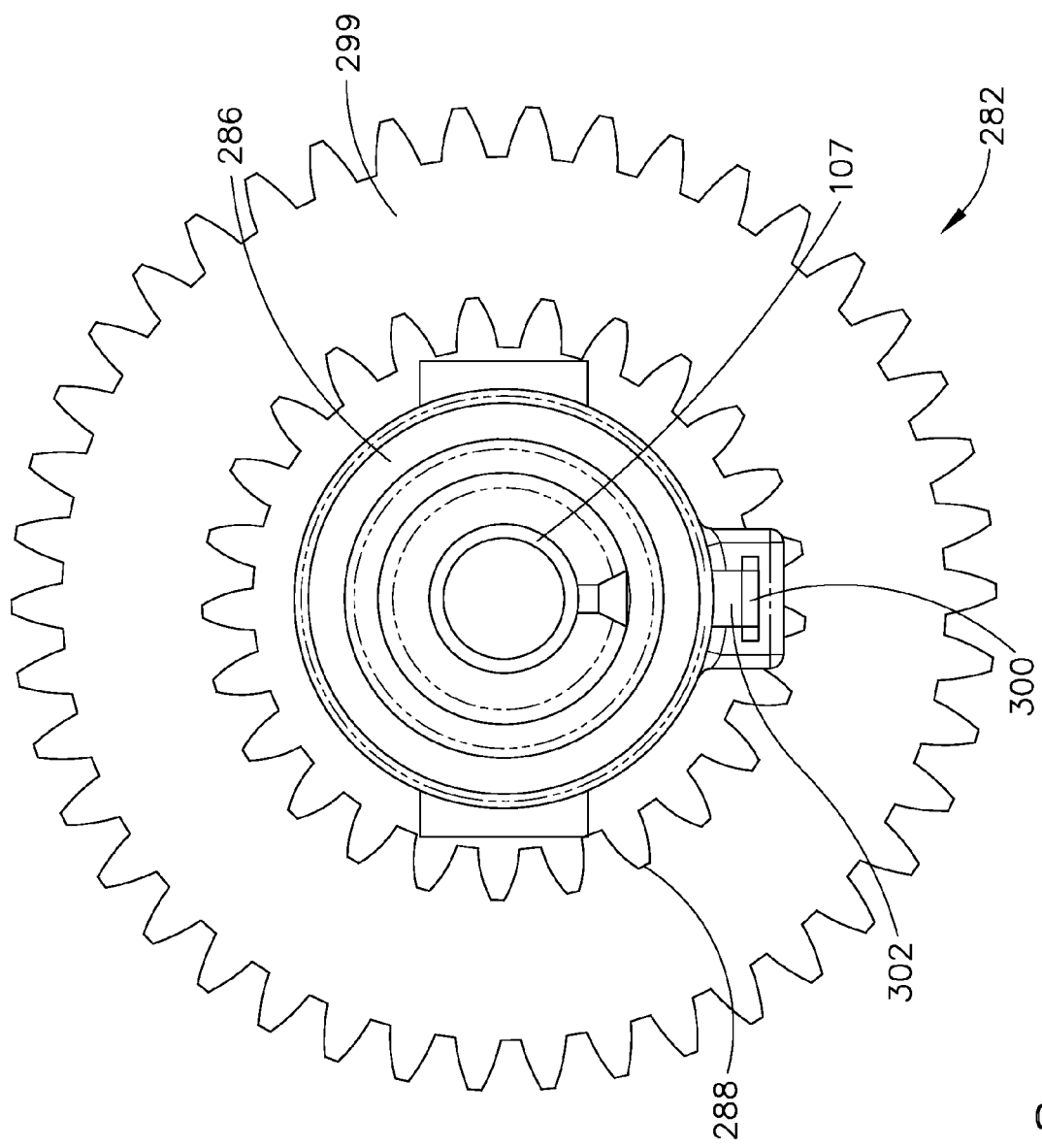
FIG. 18 depicts a section view of the cutter rotation and translation mechanism of the probe assembly of FIG. 12.
Figure 19:
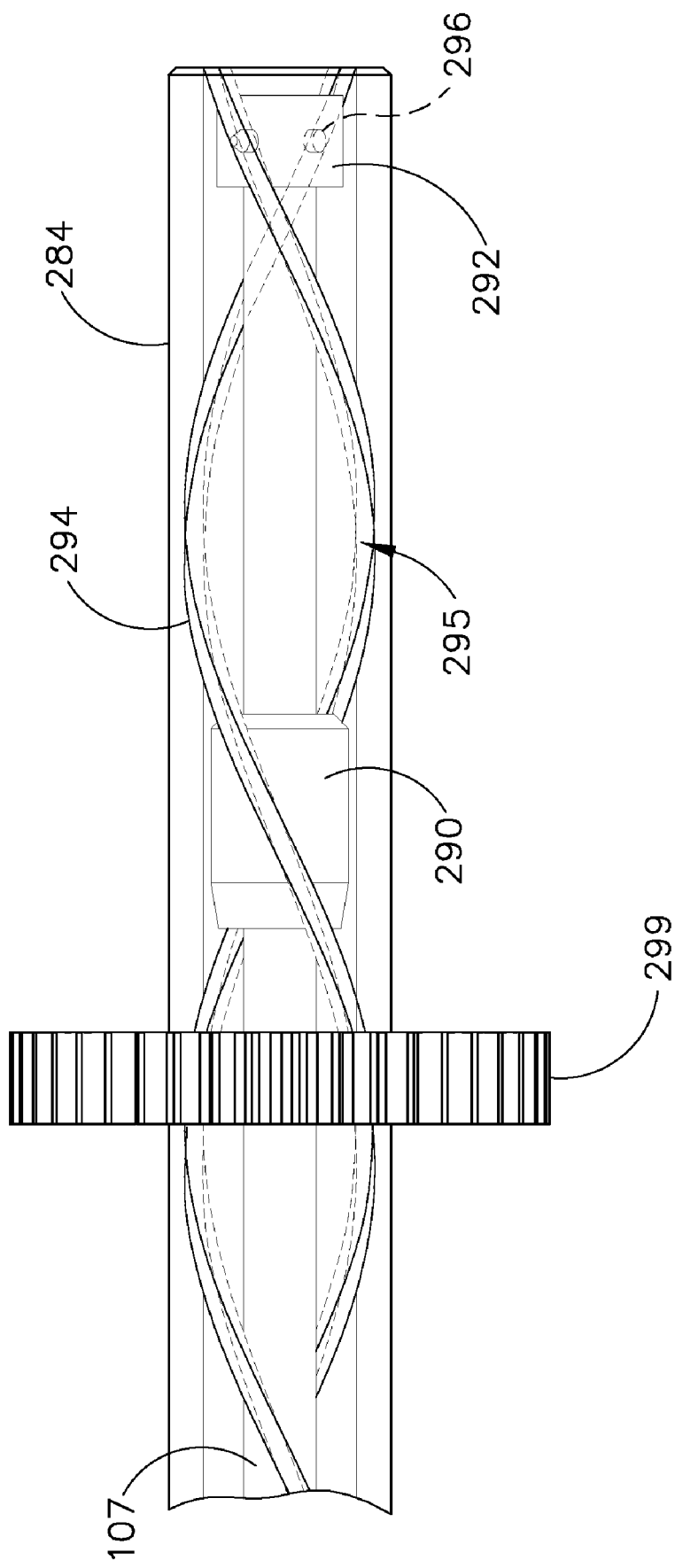
FIG. 19 depicts a partial side view of the rear portion of the cutter rotation and translation mechanism of the probe assembly of FIG. 12, showing the lead screw nut, encoder drive gear, and cutter driver with projecting pin.
Figure 20:
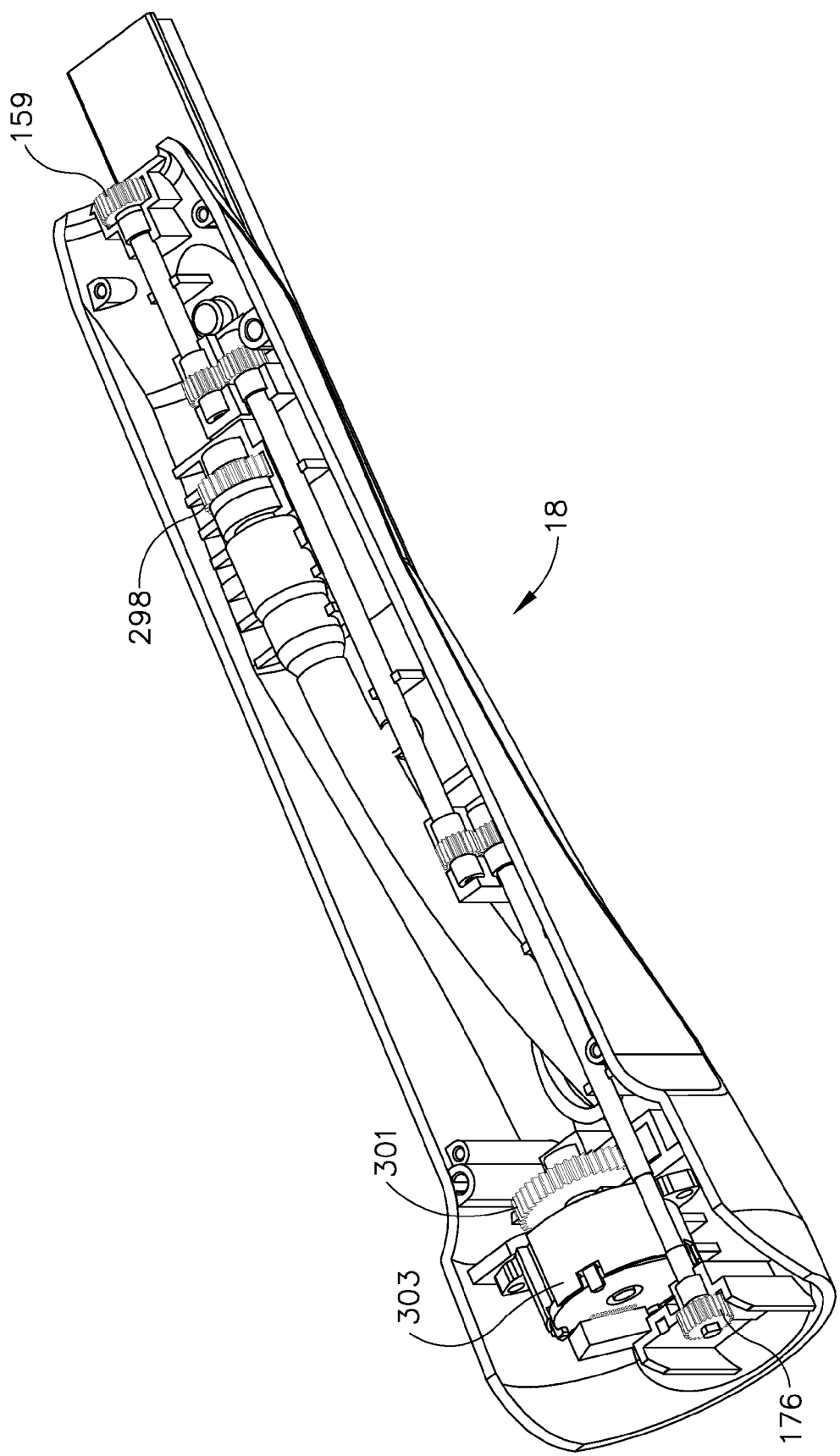
FIG. 20 depicts a perspective view of the holster assembly of FIG. 12, with the holster plate removed.
Figure 21:
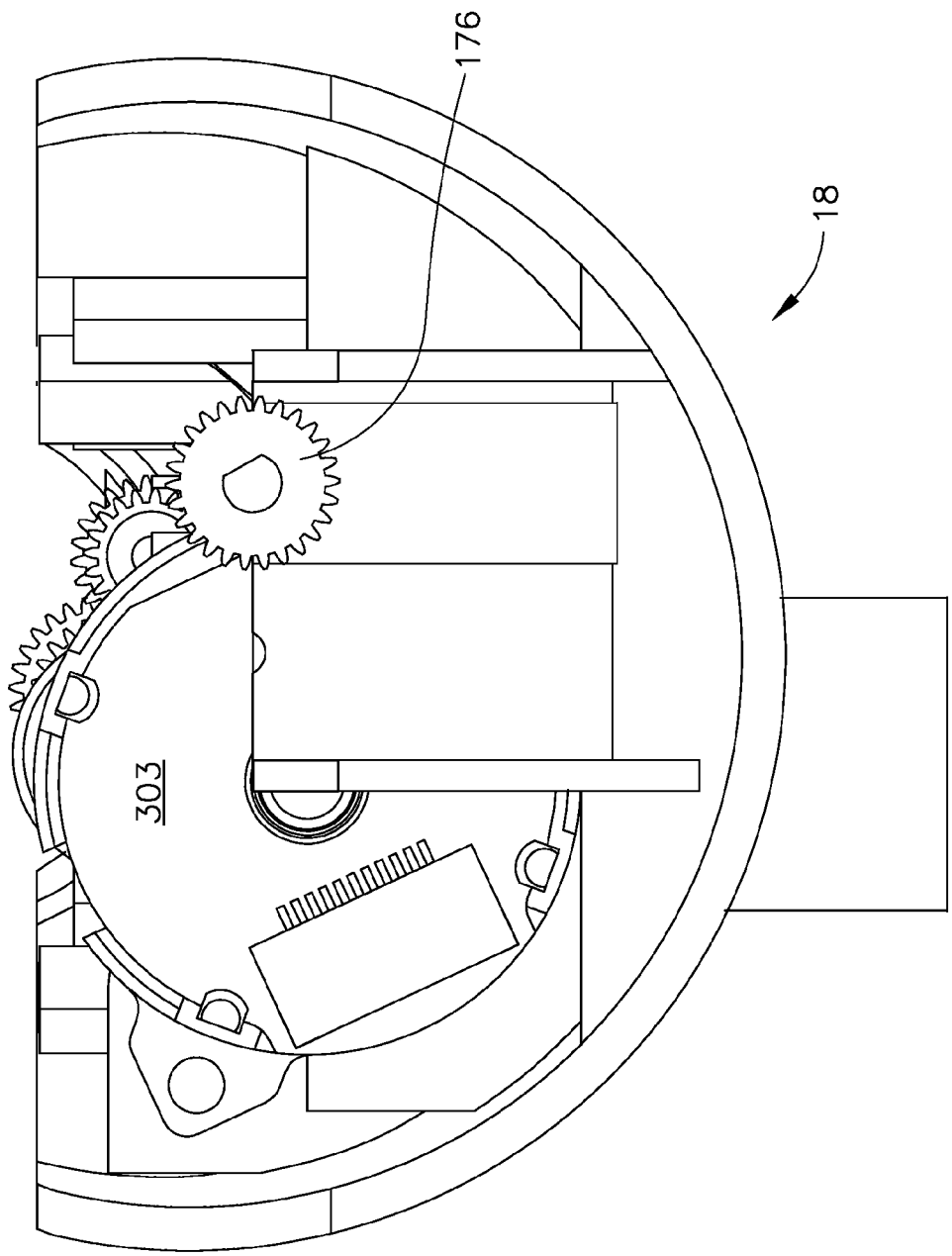
FIG. 21 depicts a rear view of the holster assembly of FIG. 12, with the holster plate removed.

Biopsy device (12) of FIGS. 12-21 provides another exemplary mode for actuating a needle indexing drive mechanism. In this example, probe assembly (18) is configured with an indexing knob (170) located on the proximal end of probe assembly (18). Indexing knob (170) is connected to a shaft (172) that has a gear (174) at its distal end, as shown in FIG. 15. Gear (174) communicates with another gear (176) (FIGS. 13 and 20-21) that is located in holster assembly (16, 20). Gear (176) in holster assembly (16, 20) connects to an arrangement of intermediate gears and shafts, which communicate the rotational motion from indexing knob (170) to a needle indexing drive gear (159) of holster assembly (20), as shown in FIGS. 13 and 20. Needle indexing drive gear (159) may communicate directly with a needle indexing gear (162) of probe, as shown in FIG. 58. Needle indexing gear (162) may rotate unitarily with needle assembly (29), as described herein. Indexing knob (170) may thus be manually rotated to rotate needle assembly (29).

Of course, knob (170) may also be similarly coupled with a drive shaft (154) that has a hexagonal needle rotation drive socket, such as in probe assembly (14) of FIGS. 1-6 or probe assembly (19) of FIGS. 7-11. For instance, needle indexing drive gear (159) may communicate indirectly with a drive shaft (154) through an intermediate drive gear (178) of the probe assembly (14), as shown in FIGS. 3-6. Furthermore, knob (170) may be coupled with drive gear (156) of the example shown in FIG. 34, in a manner similar to that by which knob (170) is coupled with drive gear (150) of the example shown in FIGS. 12-21.

It should be appreciated that the needle indexing mechanisms disclosed herein may be interchangeable among various biopsy devices (10, 12). For instance, those of ordinary skill in the art will understand that a biopsy device (10, 12) having a hexagonal interface indexing mechanism may be adapted to include a gear interface indexing mechanism, and vice versa. Similarly, those of ordinary skill in the art will understand that a biopsy device (10, 12) having a probe assembly (14, 18, 19) with a drive shaft (154) for use with a needle assembly (28) having a hexagon-shaped indexing portion (49), may be modified to substitute a needle indexing drive gear (156, 157, 159) for the drive shaft (154) for use with a needle assembly (29, 30) having a needle indexing gear (162). Additionally, the various biopsy devices (10, 12) may be adapted for use with any of the various indexing drive mechanisms disclosed.

It will further be appreciated that needle indexing may be accomplished without the use of a probe assembly (14, 18, 19) and/or holster assembly (16, 20, 21) containing a needle indexing mechanism. For instance, needle assembly (30) of FIGS. 28-32 may be configured for manual indexing by rotating needle assembly (30) when the needle assembly (30) is either detached from a probe assembly (14, 18, 19) or attached to a probe assembly (14, 18, 19) (e.g., by the operator manually grasping needle assembly (30) directly by thumbwheel (38), etc.). In addition, any suitable structures other than hexagonal or gear teeth interfaces may be used to communicate rotation to needle assembly (28, 29, 30, 134, 160, 161). Furthermore, some versions may lack needle indexing altogether.

III. Exemplary Probe Assemblies

Another aspect to consider in a biopsy device having a detachable needle may be probe assembly design. When considering such probe assemblies, some aspects to address might include the following: (A) probe assembly engagement with a detachable needle; (B) cutter exposure (i.e., sharp control) before the cutter is inserted into the detachable needle, cutter rotation, and cutter translation; and/or (C) vacuum supply and tissue sample management, among other things.

A. Exemplary Probe Assembly Mounting

1. Exemplary Rocking Probe Locking Cover

FIGS. 39-43 show an exemplary probe locking cover (182) used to engage a probe assembly (14) with a needle assembly (28). Probe assembly (14) of this example includes a casing (180) and locking cover (182). Locking cover (182) is connected to probe assembly (14) by a pivot pin (184) on casing (180). Pivot pin (184) is positioned through corresponding openings (186) in locking cover (182). The attachment of locking cover (182) to probe casing (180) in this way permits some rotation of locking cover (182) about pivot pin (184). This rotation of locking cover (182) may be used for controlling the engagement and disengagement of probe assembly (14) to needle assembly (28) as discussed in detail below. Of course, pivot pin (184) need not be a single pin passing entirely through probe assembly (14), and may simply comprise a pair of protrusions that are molded as part of casing (180) and that protrude from each side of casing. Furthermore, other suitable structures and relationships between a locking cover (182) and a probe assembly (14) will be apparent to those of ordinary skill in the art in view of the teachings herein.

Locking cover (182) of the present examples includes an engaging member (188) on its distal end. Engaging member (188) may take the form of a tab, protrusion, or any other suitable structure. Engaging member (188) uses a snap connection to attach to an annular recess or groove (190) located on a thumbwheel (36) of needle assembly (28). Springs (192) are included on each side of probe casing (180) to provide a rotational bias to locking cover (182) (e.g., urging locking cover (182) to rotate about pivot pins (184)). The bias introduced by springs (192) causes engaging member (188) to engage annular groove (190) in a secure connection, as shown in FIG. 42.

Figure 42:
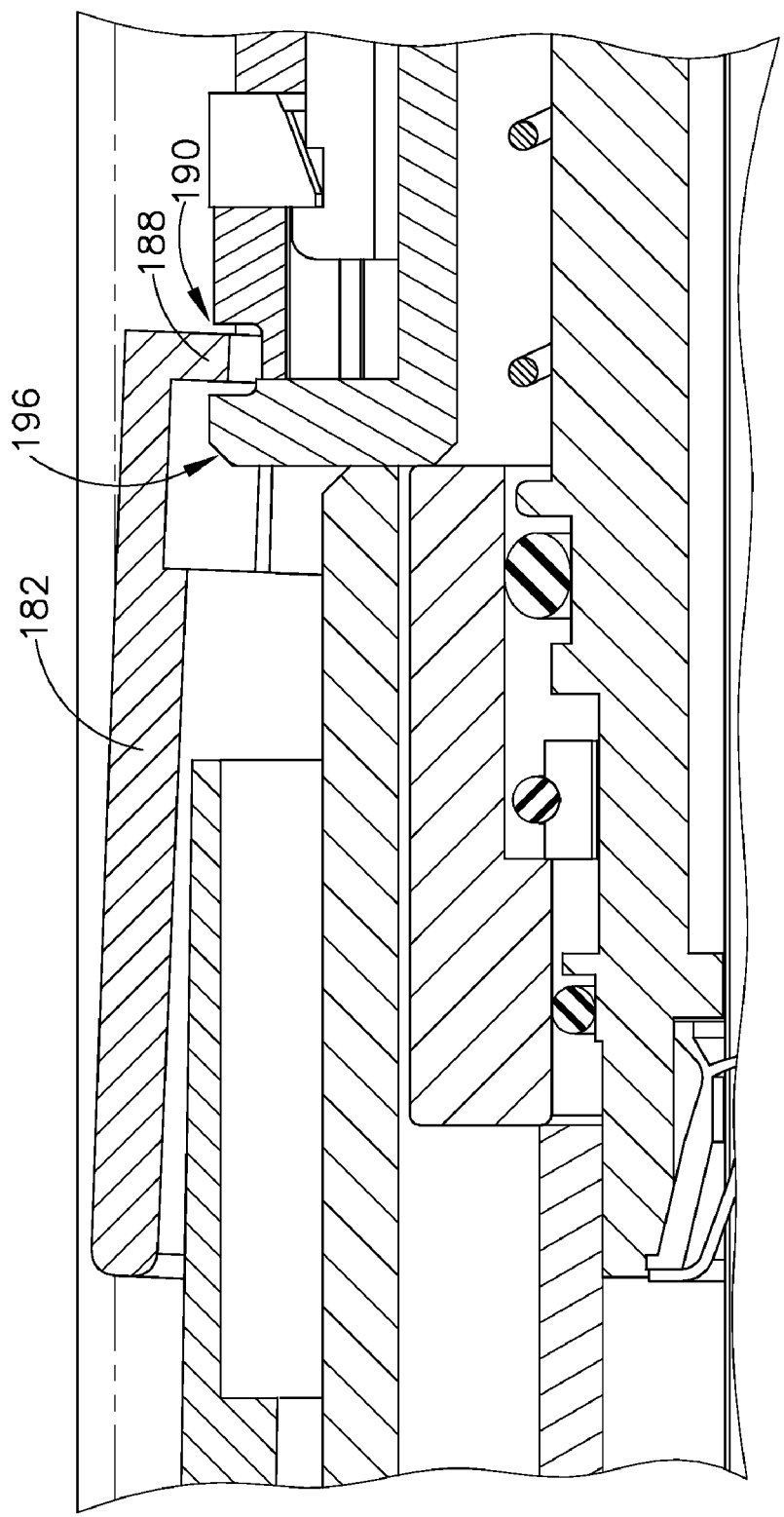
FIG. 42 depicts a cross-sectional view of the device of FIG. 39, showing engagement between the annular groove on the thumbwheel and an engaging member on the probe locking cover.
Figure 43:
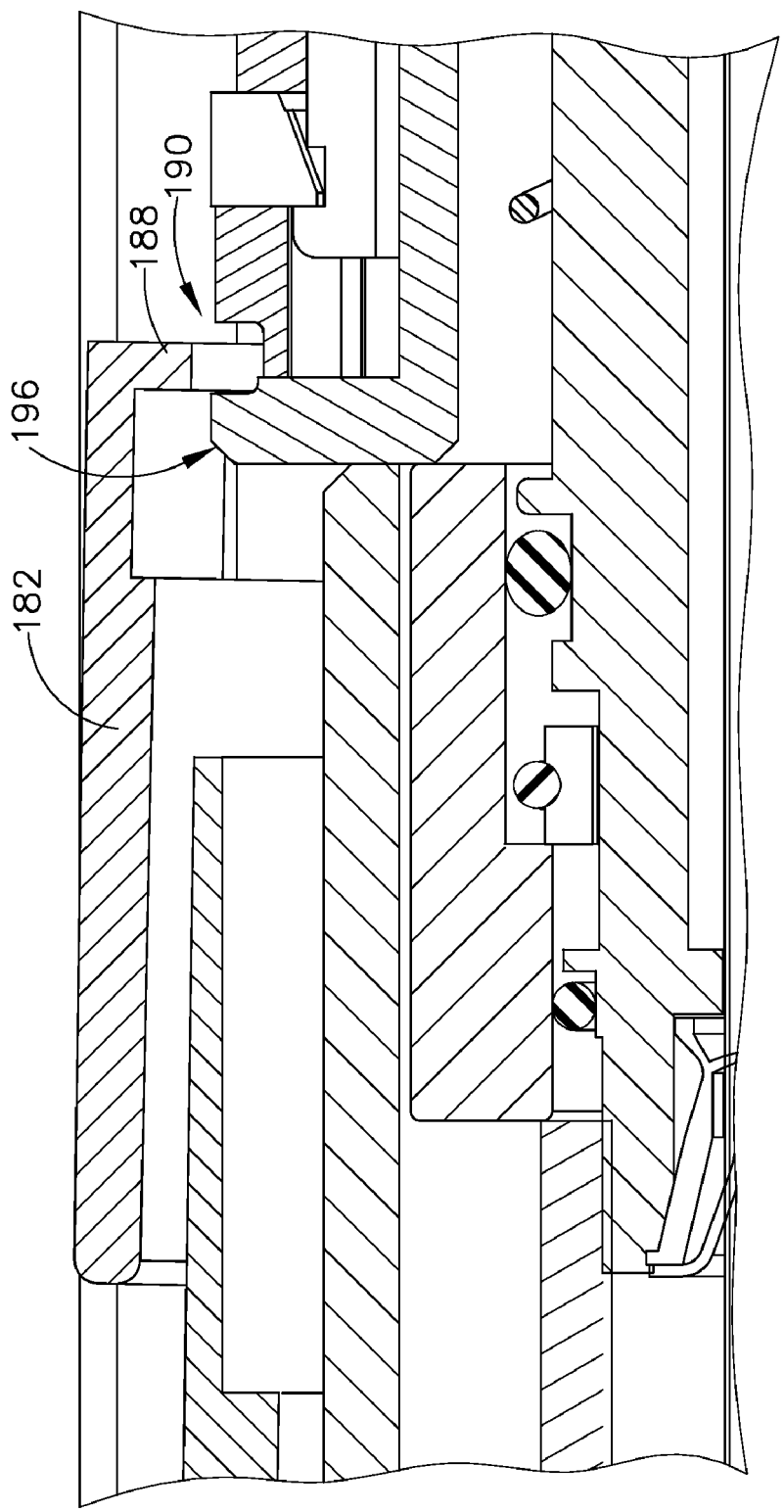
FIG. 43 depicts a cross-sectional view of the device of FIG. 39, showing position of the engaging member on the probe locking cover with respect to the annular groove on the thumbwheel when the probe assembly and needle assembly are detached.
Figure 44:
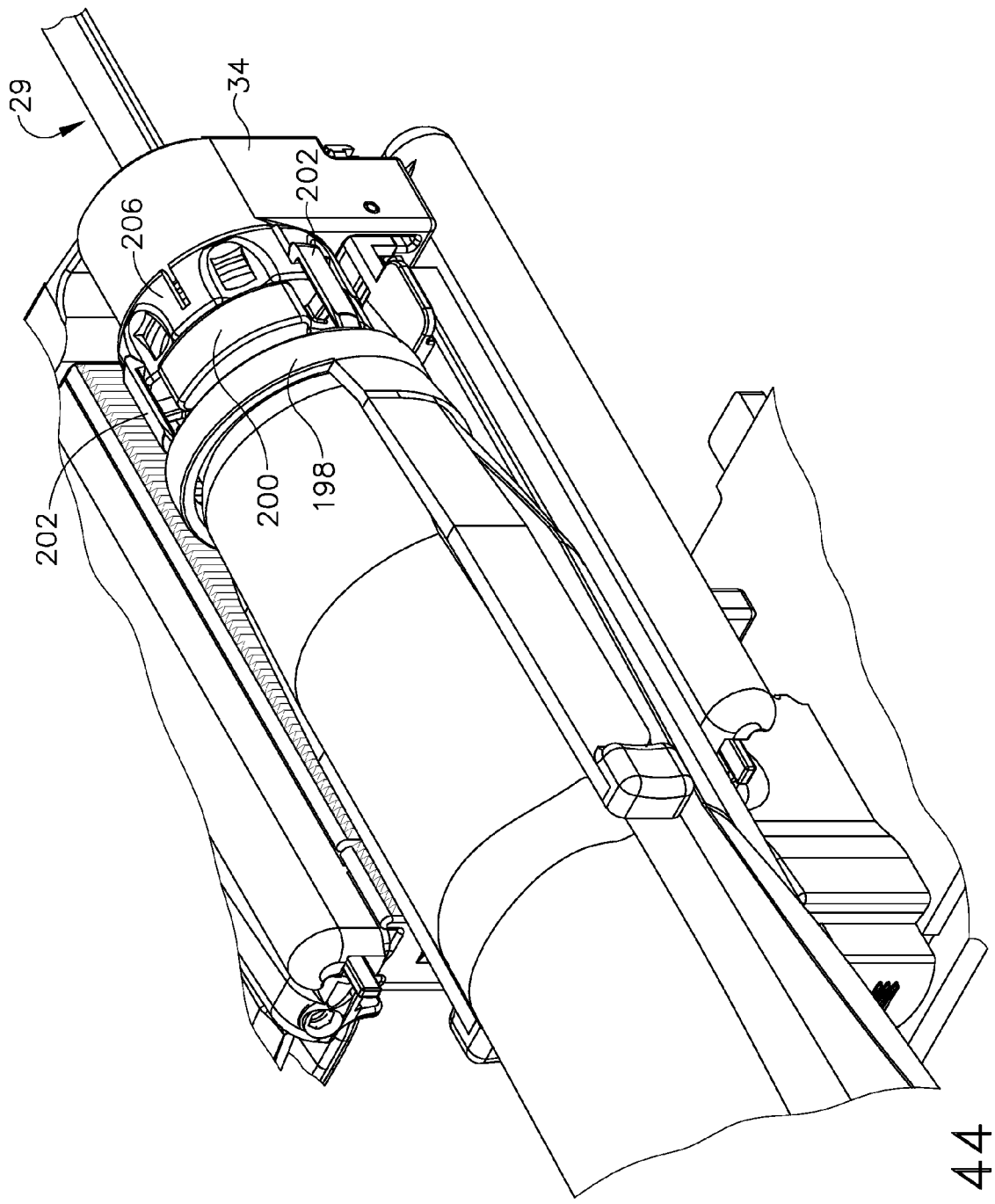
FIG. 44 depicts a partial perspective view of the MRI biopsy device of FIG. 12, showing the annular ring and locking ring for attachment of the probe assembly to the needle assembly.
Figure 45:
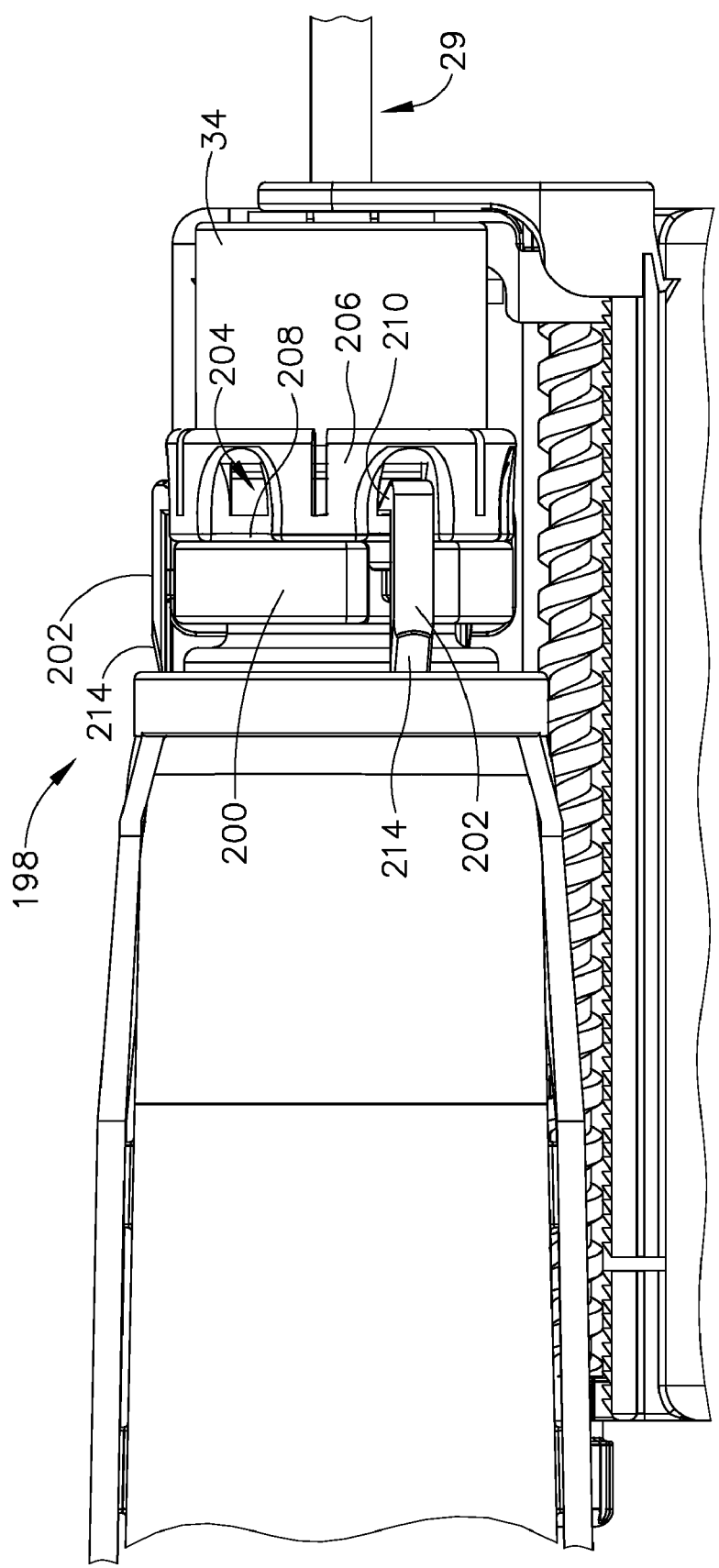
FIG. 45 depicts a partial top view of the device of FIG. 44, showing engagement between the locking ring of the probe assembly and thumbwheel of the needle assembly.
Figure 46:
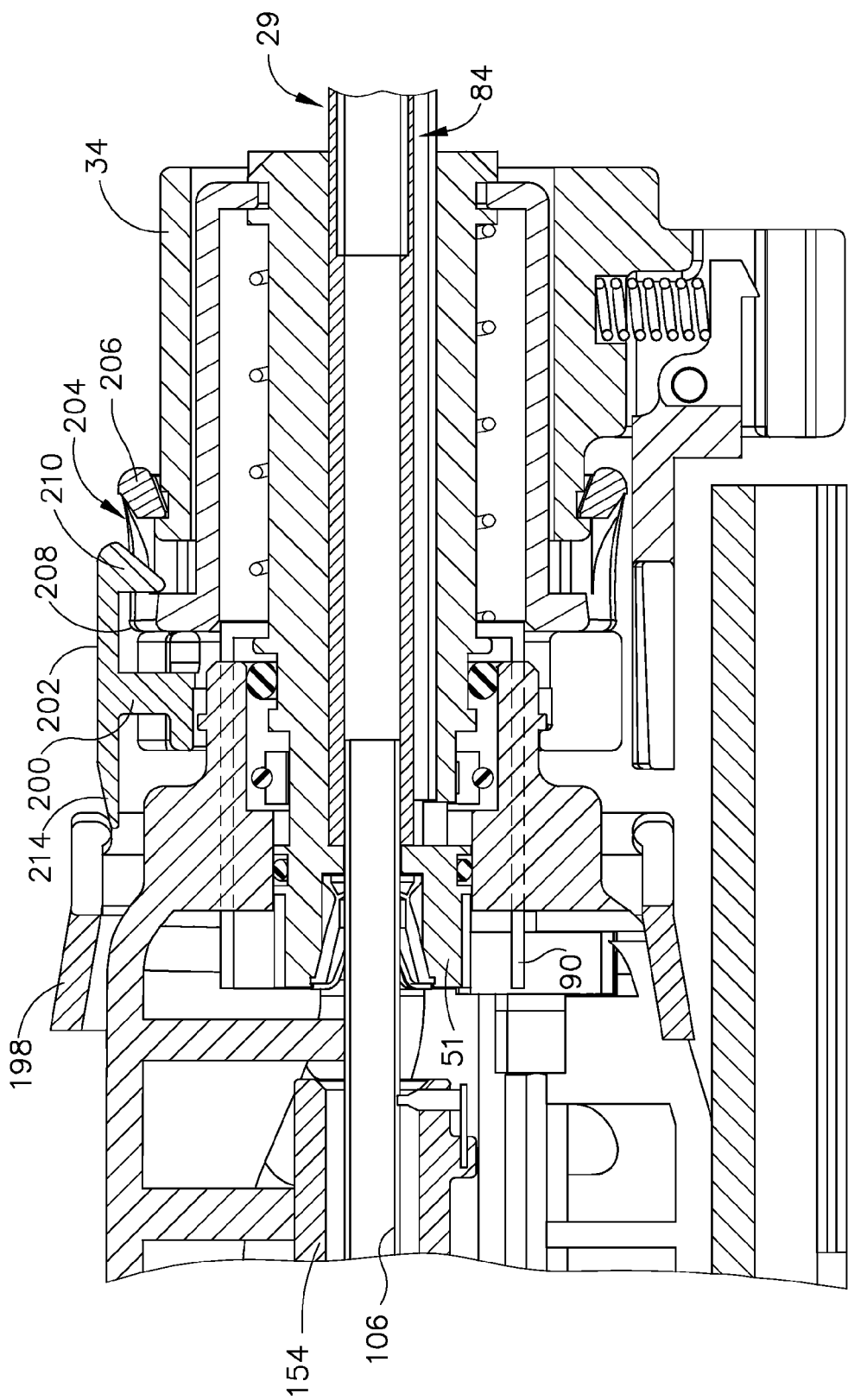
FIG. 46 depicts a partial cross-section view of the device of FIG. 44, showing the engaged position of the locking members of the locking ring with respect to the probe annular ring and the needle assembly thumbwheel.

Furthermore, thumbwheel (36) may be provided with a chamfer (196), as shown in FIGS. 42 and 43, to assist in creating the snap connection. When probe assembly (14) is pushed against needle assembly (28), chamfer (196) on thumbwheel (36) pushes engaging member (188) upward, against the force of the spring-bias from springs (192), until engaging member (188) reaches annular groove (190). When engaging member (188) reaches annular groove (190), spring-bias from springs (192) forces engaging member (188) downward into annular groove (190).

It should further be recognized that the annular groove (190) design permits the snap connection to be secure during needle indexing. For instance, annular groove (190) allows needle assembly (28) to be rotated for indexing without rotating probe assembly (14). In this example, engaging member (188) slides around within annular groove (190) during the indexing of needle assembly (28). Those of ordinary skill in the art will recognize that there are a variety of ways in which friction may be reduced during rotation, as well as structures and techniques for providing engagement without affecting rotation.

The locking cover (182) includes spring covers (194) on its proximal portion. To disengage engaging member (188) from annular groove (190), a user pushes downward on spring covers (194), which overcomes the spring-bias on locking cover (182). Such downward pushing on spring covers (194) may cause locking cover (182) to rotate about pivot pins (184). Engaging member (188) of locking cover (182) is then disengaged from annular groove (190) of thumbwheel (36), as shown in FIG. 43, and needle assembly (28) may be removed from the probe assembly (14) (e.g., by pulling probe assembly (14) longitudinally away from needle assembly (28)).

2. Exemplary Probe Locking Ring

FIGS. 44-47 show an exemplary probe annular ring (198) that may be used to mount a probe assembly (18, 19) to a needle assembly (29). Probe assembly (18, 19) includes annular ring (198) as well as a locking ring (200). Locking ring (200) of this example comprises locking members (202). To attach probe assembly (18, 19) to needle assembly (29), the user pushes probe assembly (18, 19) longitudinally against needle assembly (29). Locking members (202) of locking ring (200) engage corresponding cavities (204) in thumbwheel (206) of needle assembly (29). Locking members (202) include a chamfer (210), which allows for the proximal edge (208) of thumbwheel (206) to deflect locking members (202) until cavities (204) are reached, at which point locking members (202) will make a snap connection engaging cavities (204). Locking members (202) of this example are resiliently biased to engage cavities (204), while being flexible enough to deflect away from cavities (204) as probe assembly (18, 19) is coupled and decoupled from needle assembly (29).

To disengage probe assembly (18, 19) from needle assembly (29) in this example, the user pushes annular ring (198) distally toward needle tip (212). Annular ring (198) is configured to be slidingly engaged with probe assembly (18, 19). Such sliding engagement may be achieved by incorporating a tapered design of probe's (18, 19) distal end and sizing the diameter of annular ring (198) to achieve a sliding engagement. With such a sliding engagement, annular ring (198) may be supported on probe assembly (18, 19) by support members or rails, etc. (not shown) on the sides of probe assembly (18, 19). When annular ring (198) is pushed distally, annular ring (198) contacts a wedge portion (214) on the proximal end of locking members (202). This contact causes the distal portion of the locking members (202) to deflect away from cavities (204) and thereby disengage the thumbwheel (206).

It should further be appreciated that thumbwheel (206) may be configured with a single annular cavity or groove (not shown) instead of separate cavities (204). Such an annular cavity or groove may be similar to annular groove (190) of needle assembly (28), described above. The single annular cavity or groove (not shown) may be engaged by locking members (202) to connect the probe assembly (18, 19) to the needle assembly (29). In such a configuration, the single annular cavity or groove (not shown) may allow needle assembly (29) to be rotated for indexing without rotating probe assembly (18, 19). In this example, locking members (202) may thus slide around the single annular cavity or groove (not shown) during the indexing of needle assembly (29).

3. Exemplary Probe Locking Ring with Levers

Figure 50:
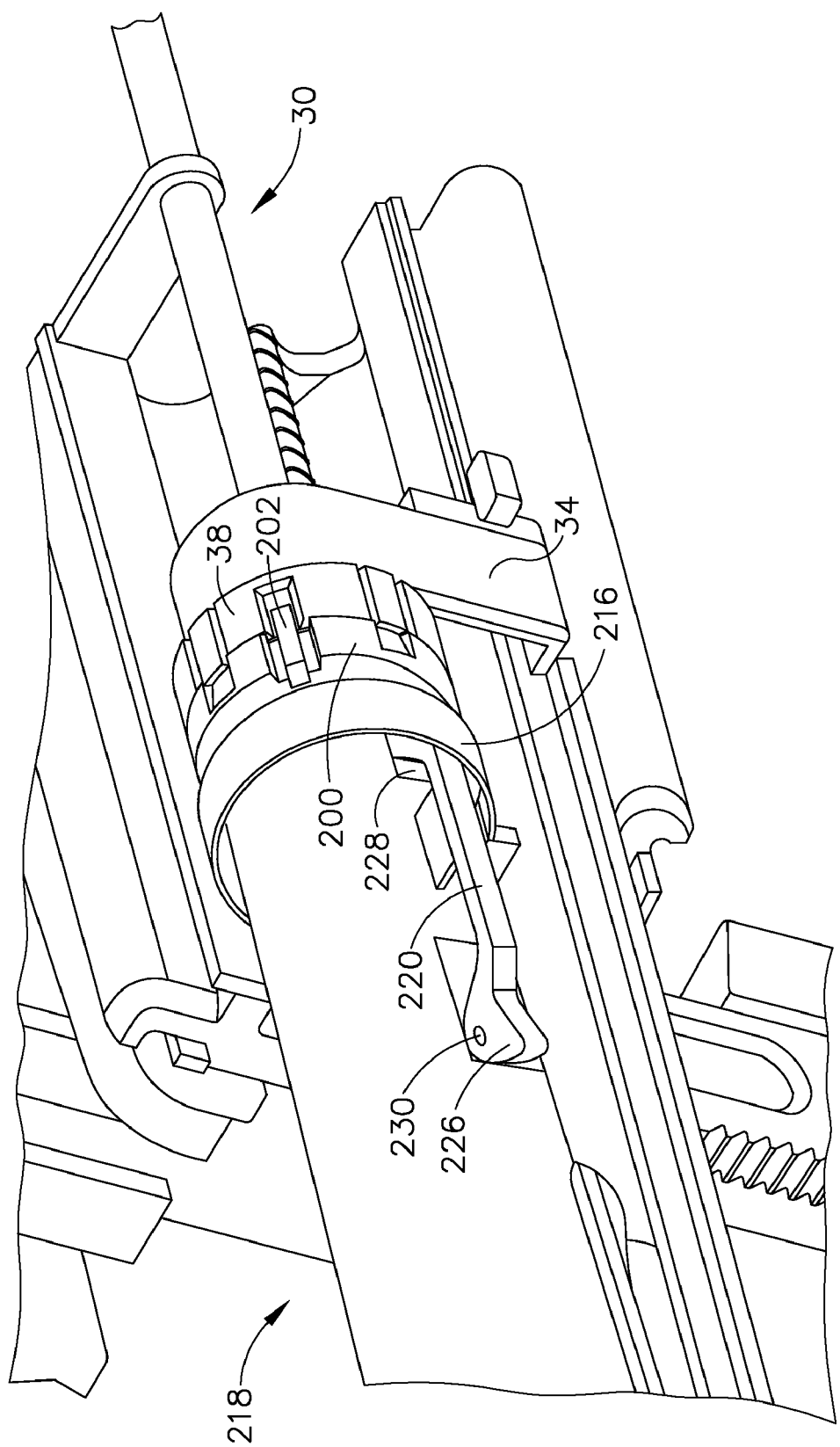
FIG. 50 is a perspective view of another exemplary interface mechanism between a probe assembly and a needle assembly.
Figure 51:
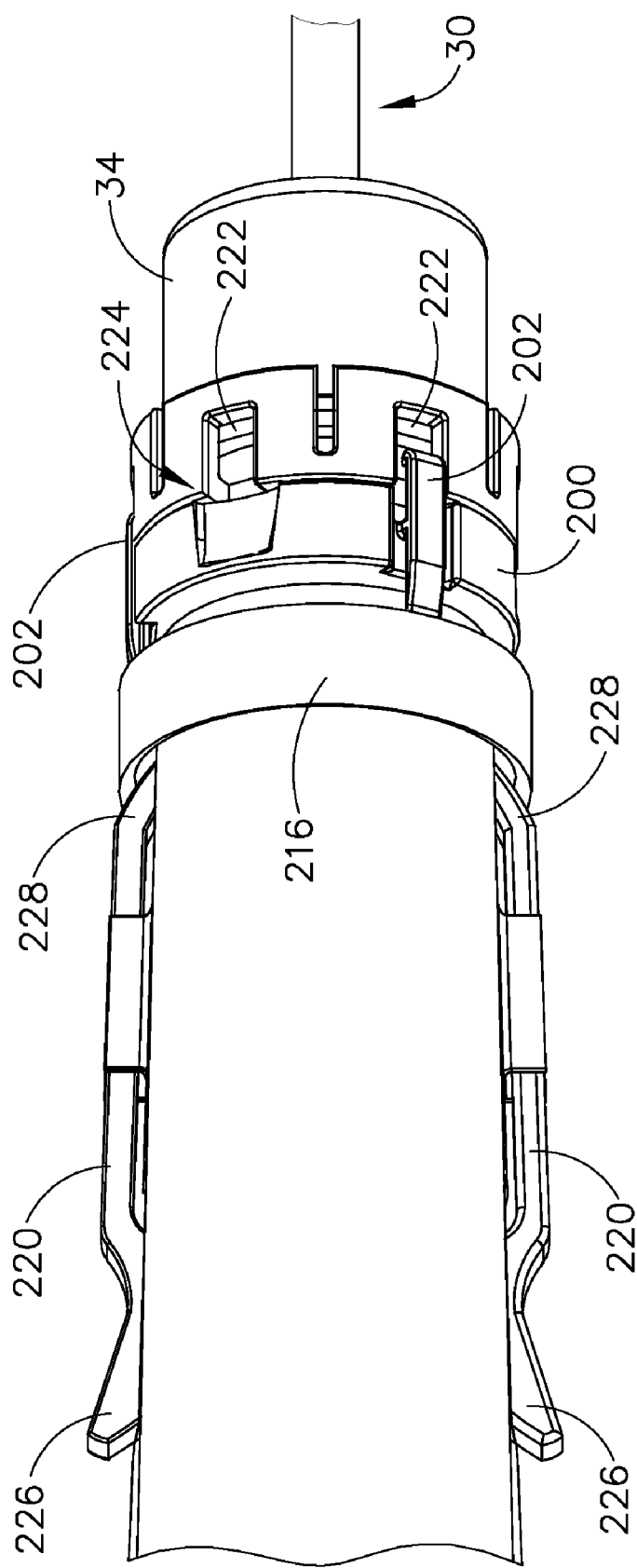
FIG. 51 depicts a top perspective view of the interface mechanism of FIG. 50, showing engagement between the probe assembly and needle assembly.

FIG. 50 and FIG. 51 show an exemplary probe annular ring (216) used to mount a probe assembly (218) to a needle assembly (30). Probe assembly (218) of this example includes an annular ring (216), a locking ring (200), and detachment levers (220). Locking ring (200) includes locking members (202) having a chamfer (not shown) on their distal end and a wedge portion (214) on their proximal end.

To attach probe assembly (218) to needle assembly (30) in this example, the user pushes probe assembly (218) longitudinally against needle assembly (30). Locking members (202) of locking ring (200) engage corresponding cavities (222) in thumbwheel (38) of needle assembly (30). Chamfer (210) of locking members (202) allows proximal edge (224) of thumbwheel (38) to deflect locking members (202) until cavities (222) are reached, at which point locking members (202) will make a snap connection with cavities (222). Locking members (202) of this example are resiliently biased to engage cavities (222), while being flexible enough to deflect away from cavities (222) as probe assembly (218) is coupled and decoupled from needle assembly (30).

To disengage probe assembly (218) from needle assembly (30), the user pushes inwardly against pivot members (226) of levers (220). Levers (220) have a chamfer (228) on their distal end. When pivot members (226) are pushed inwardly, the opposite ends of levers (220) rotate away from the body of probe assembly (218) about pivot pins (230). This rotation causes chamfer (228) of levers (220) to drive annular ring (216) distally against wedge portion (214) of locking members (202) on locking ring (200). The contact between annular ring (216) and wedge portion (214) causes the distal portion of locking members (202) to deflect away from cavities (222) and thereby disengage thumbwheel (38). Again, cavities (222) may be substituted with an annular groove or other feature or structure.

Figure 52:
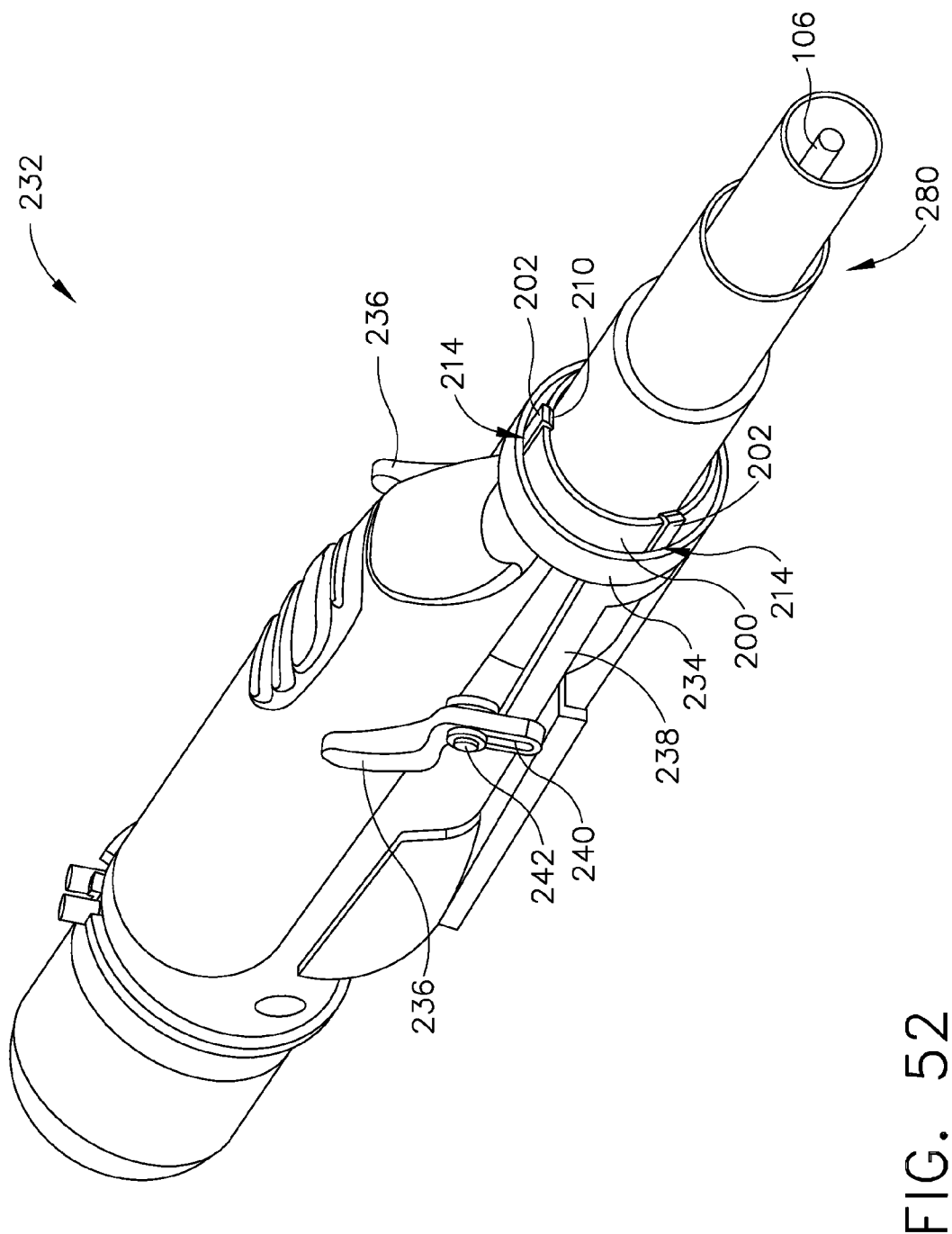
FIG. 52 depicts another exemplary probe assembly, showing an interface mechanism for attachment to a needle assembly as well as multiple telescopic cutter covers.
Figure 53:
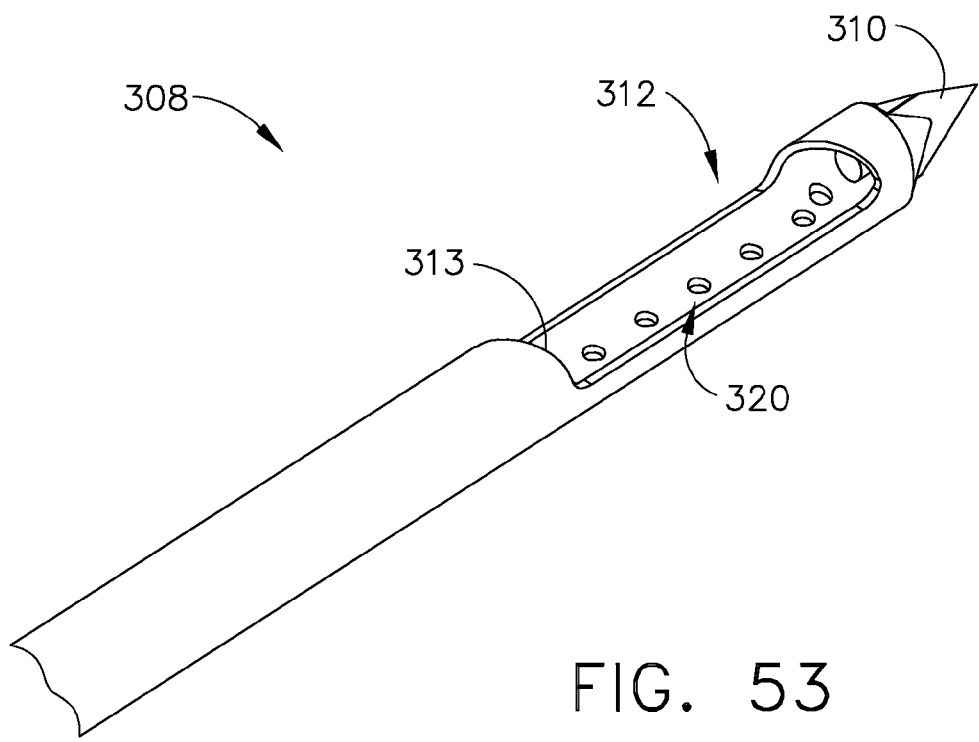
FIG. 53 depicts a perspective view of an exemplary cannula with an integral blade.

FIG. 52 shows another exemplary probe assembly (232) having an annular ring (234), locking ring (200), and detachment levers (236) for mounting probe assembly (232) to a needle assembly. Annular ring (234) comprises proximally extending extension members (238), which pivotally connect to detachment levers (236). Detachment levers (236) further each include an opening (240) that receives a pivot pin (242) of probe assembly (232) for pivotal attachment of detachment levers (236) to probe assembly (232). Locking ring (200) includes locking members (202) having a chamfer (210) on their distal end and a wedge portion (214) on their proximal end.

Attachment of probe assembly (232) to a needle assembly is achieved as described in the previous paragraphs with respect to FIGS. 44-47 and 50-51. To detach probe assembly (232) from a needle assembly, a user pulls detachment levers (236) proximally. This causes detachment levers (236) to rotate about pivot pin (242), thereby driving receiving slots (240) and connected extension members (238) distally. The distal movement of extension members (238) drives annular ring (234) distally, which then pushes against wedge portion (214) of locking members (202). The contact between annular ring (234) and wedge portion (214) causes the distal portion of locking members (202) to deflect away from a longitudinal axis of the probe assembly (232), thereby disengaging a thumbwheel of a needle assembly.

Those of ordinary skill in the art will appreciate that there are various other ways in which a probe assembly may selectively couple with a needle assembly. For example, those of ordinary skill in the art will appreciate that the thumbwheel of the needle assembly may be repositioned as a component of the probe assembly, or that the thumbwheel pre-mounted on the probe assembly. In such versions, the attachment of the probe assembly to the needle assembly may be accomplished as described above in the section discussing needle to the thumbwheel attachment. Other suitable components, features, structures, configurations, and techniques for selectively coupling a probe assembly with a needle assembly will be apparent to those of ordinary skill in the art in view of the teachings herein.

It will also be understood by those of ordinary skill in the art that the specific probe assemblies and needle assemblies identified above are merely exemplary and that no single probe assembly as indicated is meant to require a specific needle assembly. Instead, the probe assemblies and needle assemblies may be adapted such that they may be used interchangeably. For instance, needle assembly (28) may be adapted with a thumbwheel design that operates with an annular ring (198) probe mounting design instead of a locking cover (182) probe mounting design. Similarly, the probe assembly (18, 19) may be fitted with a locking cover (182) instead of an annular ring (198) for use with a needle assembly having a thumbwheel (36) with an annular groove (190). Other suitable variations in probe assembly and needle assembly combinations will be apparent to those of ordinary skill in the art in view of the teachings herein.

B. Exemplary Cutter Exposure Protection and Cutter Rotation and Cutter Translation Mechanisms Another aspect to consider with a biopsy probe having a detachable needle design may be cutter exposure and cutter rotation and translation. As discussed previously, a detachable needle design may include a needle assembly that is separate from a probe assembly and holster assembly. The cutter portion of a biopsy device may remain as a component of the probe assembly. For instance, the cutter portion may be an elongated hollow tube having a sharp distal end that serves to sever the tissue sample. Because of the sharp nature of the cutter, and with the cutter extending distally and unexposed relative to a probe assembly body, it may be important to protect the user from exposure to the cutter when the probe assembly is detached from a needle assembly. The following paragraphs will discuss several merely exemplary modes of cutter exposure protection and related cutter rotation and translation mechanisms where appropriate.

1. Exemplary Sliding Cutter Cover

Figure 2:
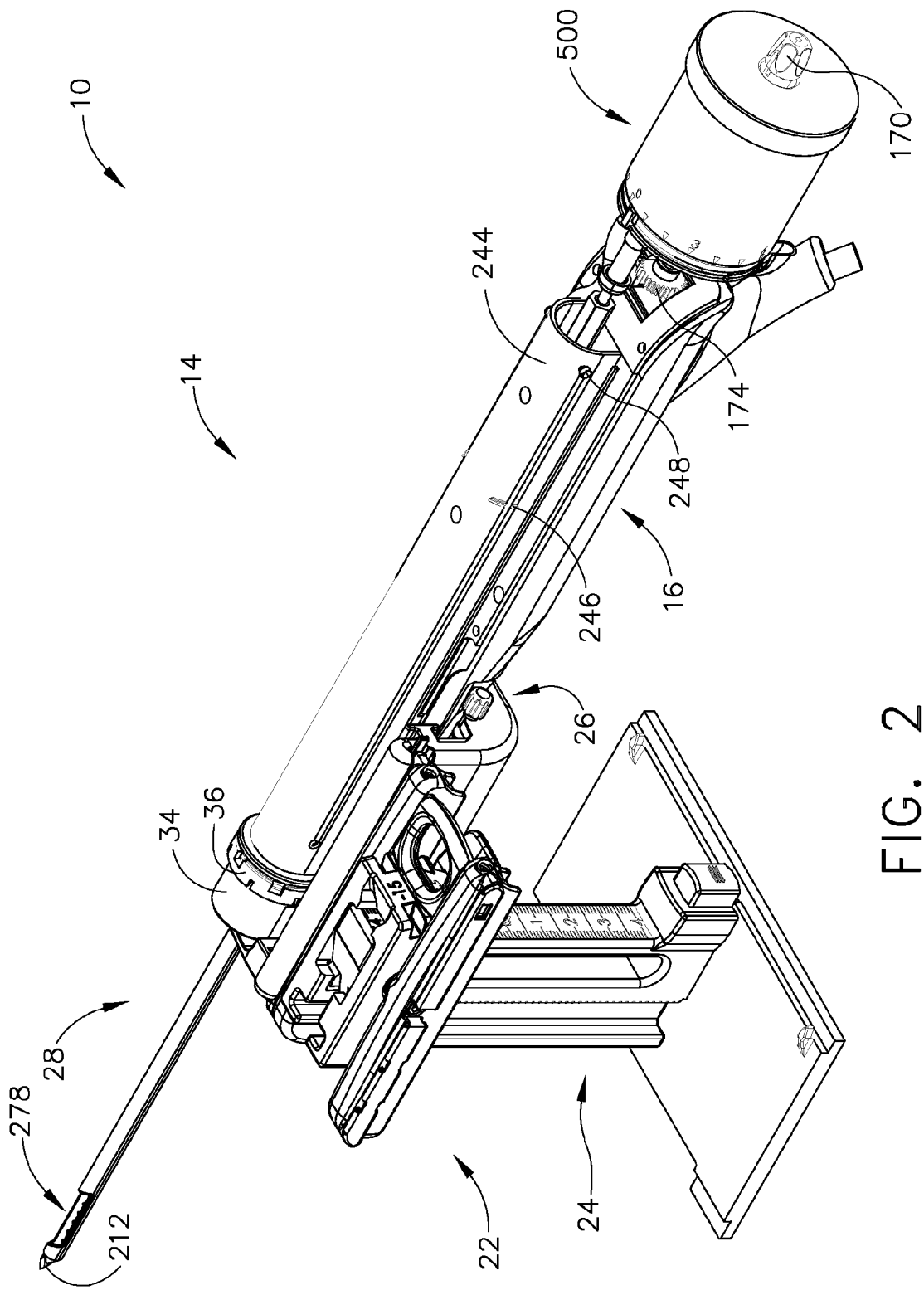
FIG. 2 depicts a perspective view of the MRI biopsy device of FIG. 1, with the probe casing and locking cover removed to show a retracted sliding cutter cover.
Figure 3:
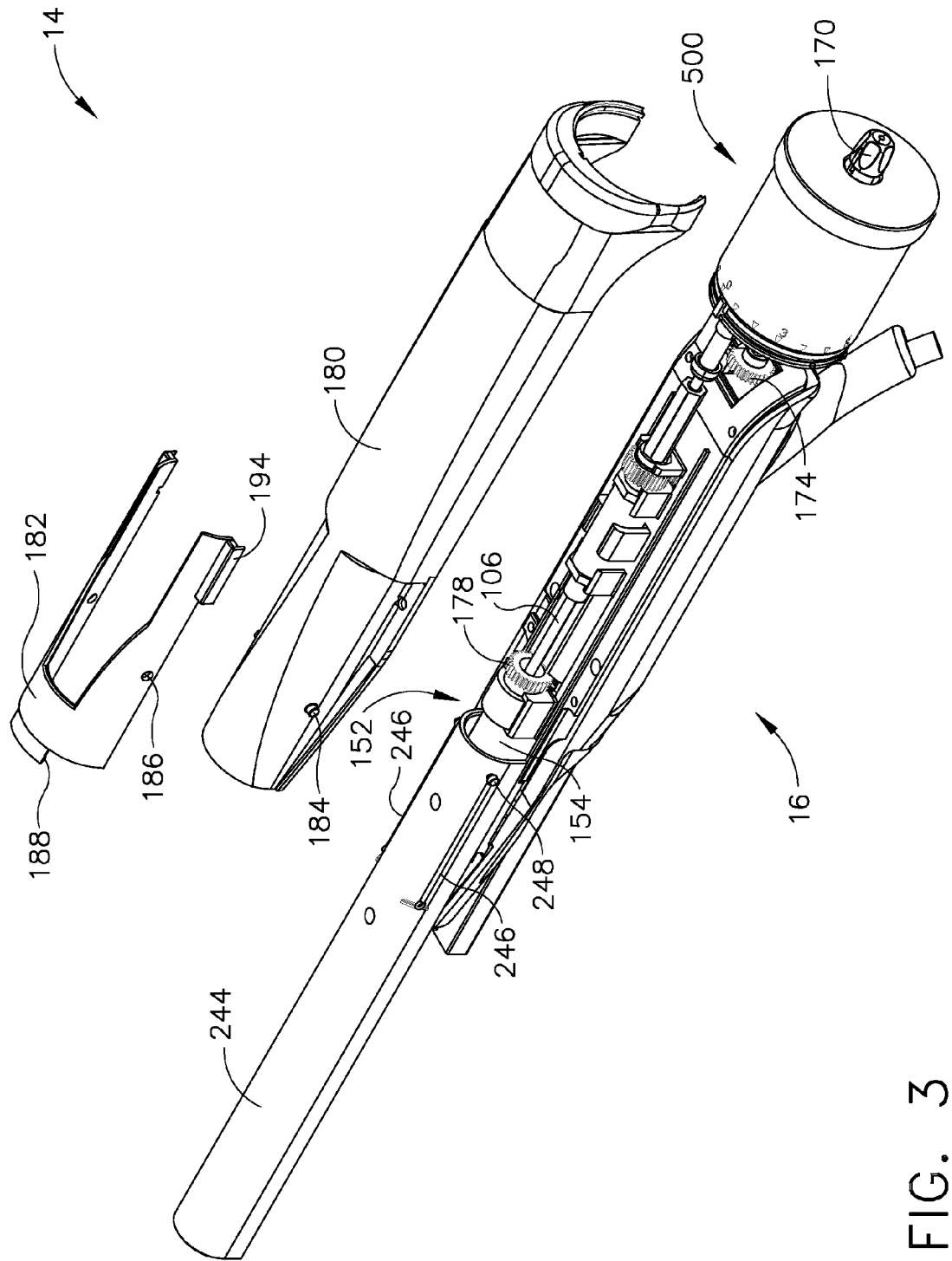
FIG. 3 depicts a partially exploded perspective view of the probe assembly and holster assembly of the MRI biopsy device of FIG. 1, showing the sliding cutter cover extended.

FIGS. 1-6 show an exemplary cutter exposure protection mode involving a sliding cutter cover (244). Probe assembly (14) of this example includes a sharp cutter (106) that extends distally from the body of probe assembly (14). This cutter (106) is configured to be inserted into a needle assembly (28) when probe assembly (14) is coupled with needle assembly (28), as described above. The sharp distal edge of cutter (106) and its distal extension from the body of probe assembly (14) may present a hazard to a user of probe assembly (14), which may warrant covering cutter (106) to some degree when probe assembly (14) is not coupled with a needle assembly (28) (e.g., when cutter (106) would otherwise be exposed). As shown in FIGS. 1-2, sliding cutter cover (244) is configured to retract inside probe assembly (14) when probe assembly (14) is coupled with a needle assembly (28). As shown in FIGS. 3-6, sliding cutter cover (244) is configured to extend distally from probe assembly (14) when probe assembly (14) is not coupled with a needle assembly (28). The extension of sliding cutter cover (244) may protect a user from exposure to the sharp cutter (106). By way of example only, cutter cover (244) may extend from the body of probe assembly (14) to a greater length than the length to which cutter (106) extends from the body of probe assembly (14).

In operation, elastic strings (246) may be used to control the movement of sliding cutter cover (244). For instance, elastic strings (246) may connect to external hooks (248) on a proximal portion of sliding cutter cover (244). Similarly, the opposing ends of elastic strings (246) may connect to internal hooks (not shown) on a distal portion of probe casing (180). This arrangement may allow for elastic strings (246) to bias sliding cutter cover (244) to an extended position when probe assembly (14) is not coupled with a needle assembly (28). When probe assembly (14) is coupled with a needle assembly (28), sliding cutter cover (244) is retracted in probe assembly (14) against tension in the elastic strings (246). For instance, the distal edge of an extended sliding cutter cover (244) may contact the proximal face of thumbwheel (36) when an operator starts to couple probe assembly (14) with needle assembly (28). Needle assembly (28) may be fixed in place by stand assembly (24). Accordingly, as probe assembly (14) is moved distally to couple with needle assembly (28), engagement between the distal edge of sliding cutter cover (244) and the proximal face of thumbwheel (36) may urge sliding cutter cover (244) proximally to a retracted position within probe assembly (14).

When needle assembly (28) is detached from probe assembly (14), the tension in elastic strings (246) is released and sliding cutter cover (244) automatically extends back to the extended position to protect the sharp cutter (106). Of course, any other suitable component, structure, feature, or configuration may be used in addition to or in lieu of elastic strings (246) to bias sliding cutter cover (244) to an extended position. By way of example only, one or more springs may be used in addition to, or in place of, elastic strings (246). Still other suitable components, structures, features, or configurations will be apparent to those of ordinary skill in the art in view of the teachings herein.

Sliding cutter cover (244) may be designed to have any suitable shape that may effectively reduce a user's exposure to the sharp cutter (106). For example, as shown in FIGS. 2-6, sliding cutter cover (244) may have an inverted U-shape profile. In other versions, sliding cover (244) may have a circular or cylindrical shape, a C-shape, a V-shape, or any other suitable shape. Other suitable shapes for sliding cutter cover (244) will be apparent to those of ordinary skill in the art in view of the teachings herein.

In terms of cutter rotation and translation associated with a biopsy probe device having a sliding cutter cover (244) as described above, a conventional cutter rotation and translation mechanism may be used. Suitable cutter rotation and translation mechanisms are described in further detail in U.S. Pub, No. 2008/0195066, entitled "Revolving Tissue Sample Holder For Biopsy Device," published Aug. 14, 2008, the disclosure of which is incorporated by reference herein; and U.S. Non-Provisional patent application Ser. No. 12/337,942, entitled "TISSUE BIOPSY DEVICE WITH CENTRAL THUMB WHEEL," filed on even date herewith, now published as U.S. Pat. Pub. No. 2010/0160819, the disclosure of which is incorporated by reference herein. Alternatively, any other suitable mechanism may be used to rotate and/or translate cutter (106).

It should be understood that, the length of cutter (106) may be such that, when probe assembly (14) is coupled with needle assembly (28), the distal end of cutter (106) may be positioned just proximal to (e.g., very near to yet still proximal to) the proximal edge of aperture (278). When a cutting sequence is initiated, cutter (106) will thus not need to travel far in order to sever tissue protruding through aperture (278). In other words, cutter (106) will not necessarily have to travel the full longitudinal length of needle assembly (28) in order to reach aperture (278) to sever a tissue sample when a cutting sequence is initiated. Cutter (106) may thus be effectively "staged" for cutting immediately upon coupling of probe assembly (14) with needle assembly (28).

2. Exemplary Telescoping Cutter Cover

FIGS. 7-11 show an exemplary cutter exposure protection mode involving partial retraction of cutter (106), along with a telescopic cutter cover (250). When probe assembly (19) is coupled with a needle assembly (29) in this example, telescopic cutter cover (250) retracts inside probe assembly (19) against a compression spring (252). For instance, the distal edge of an extended telescopic cutter cover (250) may contact the proximal face of thumbwheel (206) when an operator starts to couple probe assembly (19) with needle assembly (29). Needle assembly (29) may be fixed in place by stand assembly (24). Accordingly, as probe assembly (14) is moved distally to couple with needle assembly (29), engagement between the distal edge of telescopic cutter cover (250) and the proximal face of thumbwheel (206) may urge telescopic cutter cover (250) proximally to a collapsed or retracted position probe assembly (19). With probe assembly (19) being coupled with needle assembly (29), cutter (106) may partially extend within needle assembly (29) without exposing the user to sharp cutter (106).

When probe assembly (19) is detached from needle assembly (29), telescopic cutter cover (250) extends from probe assembly (19) under the distal urging of compression spring (252). Also, cutter (106) is partially retracted inside the probe assembly (19) by a cutter translation and rotation mechanism as discussed further below. The combination of partially retracted cutter (106) and extended telescopic cutter cover (250) may protect a user from exposure to the sharp cutter (106) to some degree.

Figure 8:
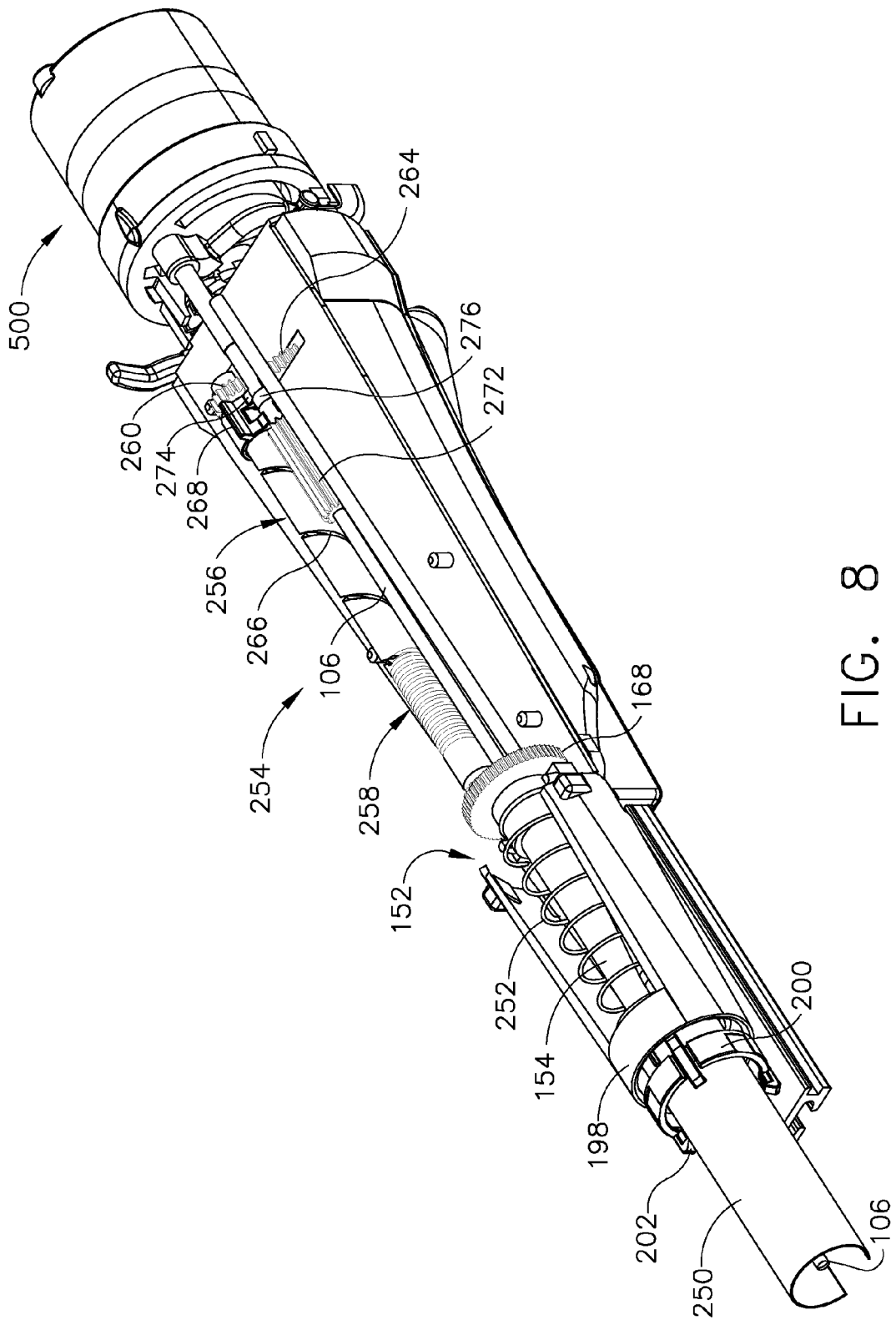
FIG. 8 depicts a perspective view of the MRI biopsy device of FIG. 7, with the probe casing and keypad removed to show internal components of the probe assembly.
Figure 9:
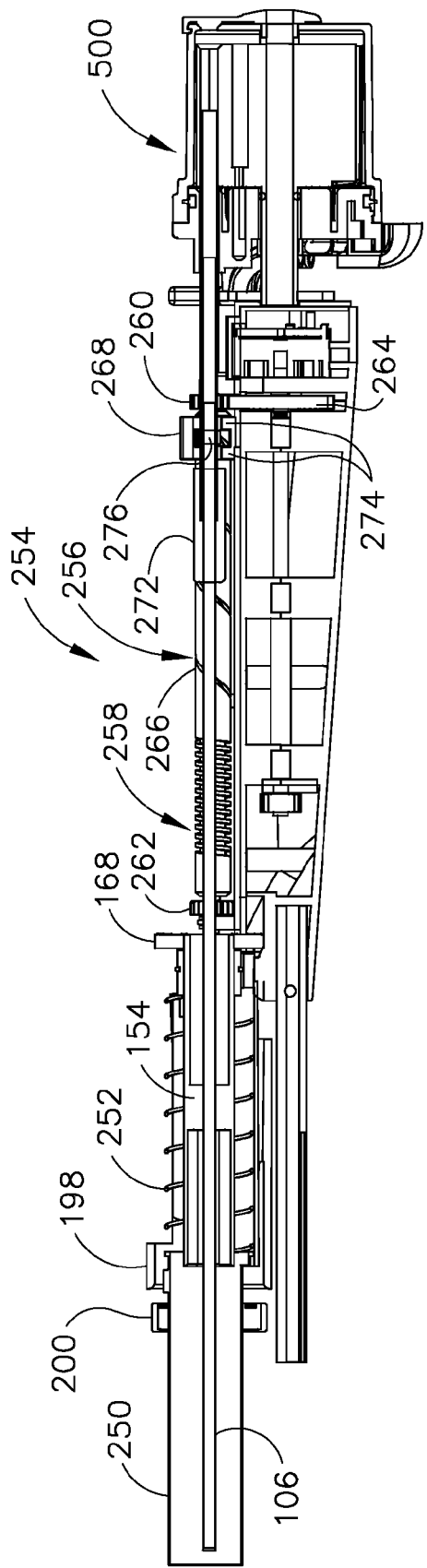
FIG. 9 depicts a cross-section view of the MRI biopsy device of FIG. 7.
Figure 10:
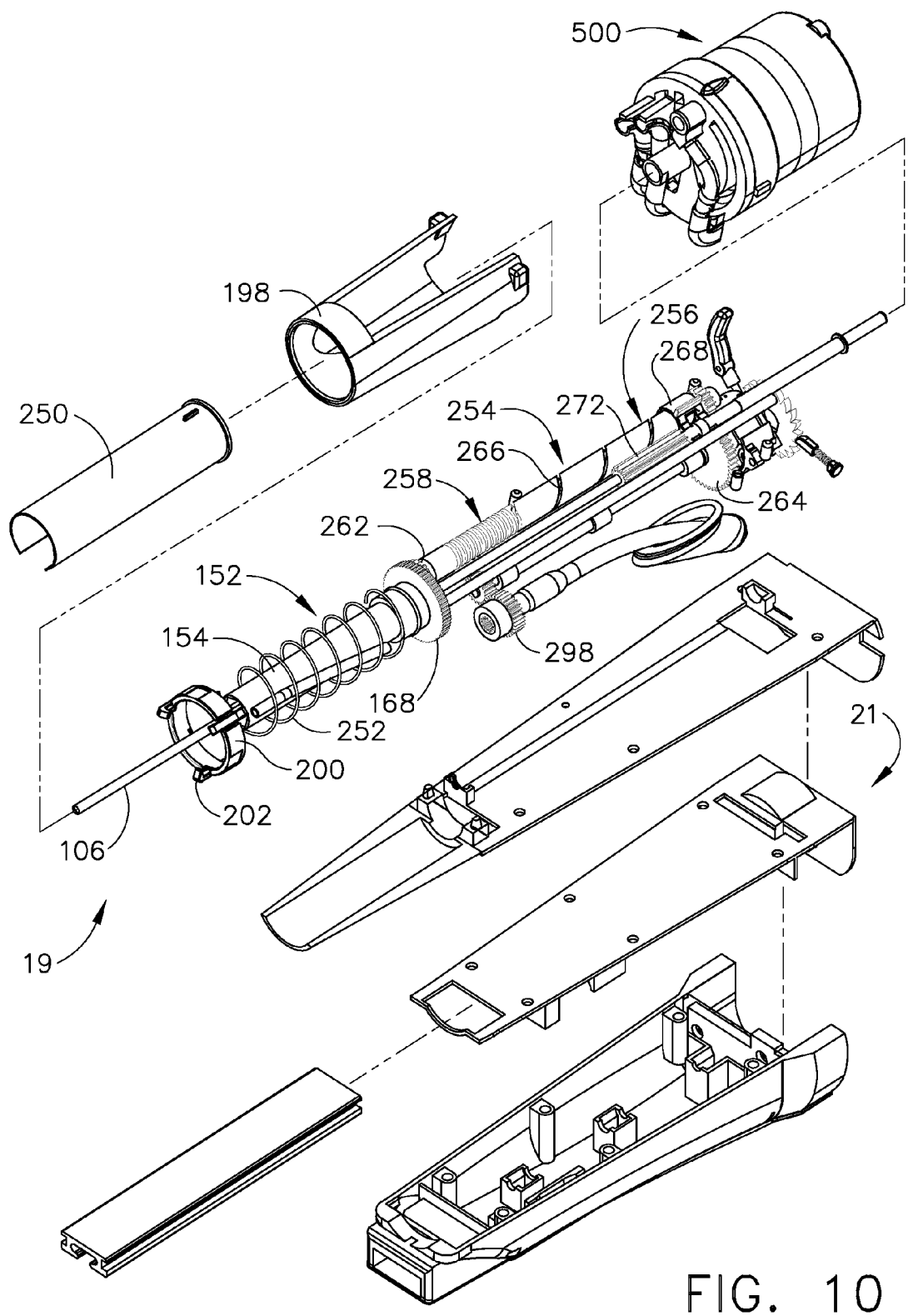
FIG. 10 depicts a partially exploded perspective view of the MRI biopsy device of FIG. 7.
Figure 11:
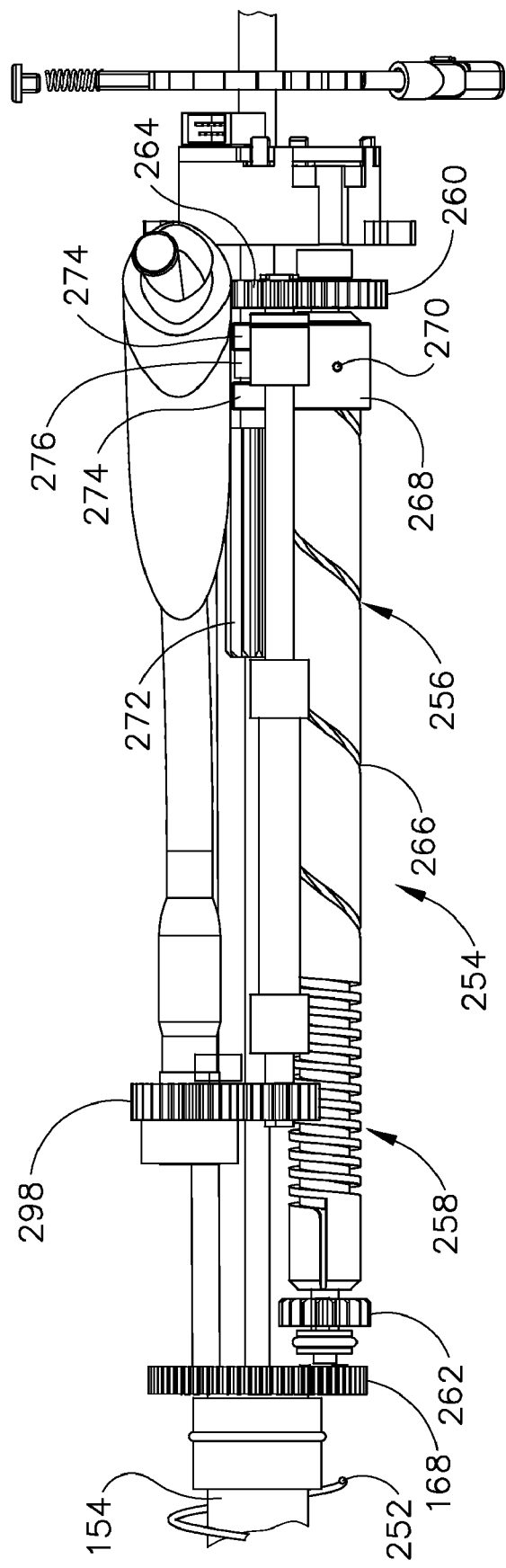
FIG. 11 depicts a partial bottom view of the MRI biopsy device of FIG. 7, showing internal components of the probe assembly and holster assembly.

As shown in FIGS. 8-10, compression spring (252) is located in the distal portion of probe assembly (19). At its distal end, the compression spring (252) is engaged with the proximal end of telescopic cutter cover (250). The proximal end of compression spring (252) is engaged with probe assembly (19). The configuration of compression spring (252) provides a spring-bias that extends telescopic cutter cover (250) distally when probe assembly (19) is not coupled with a needle assembly (29). Compression spring (252) nevertheless permits telescopic cutter cover (250) to retract proximally within probe assembly (19) when probe assembly (19) is coupled with a needle assembly (29). It will be appreciated that other components may be used to achieve the extension and retraction of telescopic cutter cover (250). By way of example only, an elastic string configuration may be used as discussed above with respect to sliding cutter cover (244). Still other suitable components, structures, features, configurations, or techniques for achieving extension and retraction of telescopic cutter cover (250) will be apparent to those of ordinary skill in the art in view of the teachings herein.

Also as shown in FIGS. 8-11, an external helix (254) provides the ability to translate cutter (106) longitudinally within probe assembly (19); while a cutting gear (262) provides the ability to rotate cutter (106) to sever a tissue sample. External helix (254) includes a translation gear (260) at its proximal end and cutting gear (262) at its distal end. Gears (260, 262) are fixedly coupled with external helix (254) in this example, such that gears (260, 262) and external helix (254) rotate unitarily. External helix (254) further includes a track (266) having a fast thread portion (256) and a fine thread portion (258). Fast thread portion (256) has a high pitch to provide for smooth and rapid translation of cutter (106) from its partially retracted state to its extended state. Fine thread portion (258) has a low pitch to provide for fine controlled translation of cutter (106) during cutting action. A bracket (268) included on external helix (254) is provided with a pin (270) that fits within track (266). Bracket (268) further attaches to cutter (106), and serves as a carriage to translate cutter (106) longitudinally while permitting cutter (106) to rotate relative to bracket (268).

Translation gear (260) is in communication with a drive gear (264), which is exposed by holster assembly (21). As will be described in greater detail below, holster assembly (21) is operable to rotate drive gear (264). Furthermore, translation gear (260) and drive gear (264) are positioned and configured such that gears (260, 264) mesh when probe assembly (19) is coupled with holster assembly (21). Rotation of drive gear (264) thus causes corresponding rotation of the translation gear (260), which in turn causes external helix (254) to rotate. As external helix (254) rotates, the bracket (268) translates longitudinally due to engagement of pin (270) with track (266). Cutter (106), being attached to bracket (268), translates longitudinally with bracket (268). The translating movement is greater when bracket (268) travels through fast thread portion (256) of track (266) compared to fine thread portion (258).

Rotation of drive gear (264) also imparts rotation to the cutting gear (262) through cutting gear's (262) connection with external helix (254). An elongated gear (272) is unitarily secured to cutter (106) (e.g., via overmolding, etc.) in this example. Elongated gear (272) is configured to engage cutting gear (262) once cutter (106) has translated from its partially retracted position. In particular, thread portions (256, 258) and elongated gear (272) are sized and configured such that, about when pin (270) reaches a transition between fast thread portion (256) and fine thread portion (258), cutter (106) has translated distally to a longitudinal position whereby elongated gear (272) engages cutting gear (262). The engagement of cutter gear (262) with elongated gear (272) is such that rotating cutter gear (262) rotates elongated gear (272), thereby rotating cutter (106), which may aid in severing a tissue sample. Furthermore, the elongated design of elongated gear (272) may allow for continued rotation as cutter (106) translates through a longitudinal range of motion.

It will therefore be appreciated that, in the present example, bracket (268) is attached to cutter (106) in a way that allows cutter (106) to rotate freely while translating longitudinally. For instance, as shown in FIG. 8, bracket (268) may include open clamp members (274) that are positioned on each side of a blocking member (276) associated with cutter (106). Also, in this configuration, it will be appreciated that the placement of the components is such that the fine translating movement and rotation of cutter (106) may coincide with the point at which cutter (106) reaches the aperture (278) of an attached needle assembly (29). Of course, any other suitable structures, features, components, configurations, and/or techniques may be used to rotate and/or translate cutter (106) to sever a tissue sample.

It will also be appreciated that telescopic cutter cover (250) may be designed to have any suitable shape that may effectively reduce a user's exposure to the sharp cutter (106). For instance, as shown in FIGS. 7-10, telescopic cutter cover (250) may have an inverted C-shape. In other exemplary versions, telescopic cutter cover (250) may have a hollow cylinder shape, a U-shape, a V-shape, or any other suitable cross-sectional shape. Other suitable shapes for telescopic cutter cover (250) will be apparent to those of ordinary skill in the art in view of the teachings herein.

In the present example, approximately 60% of the length of cutter (106) is retracted within probe assembly (16) when cutter (106) is in a retracted position; while telescoping cutter cover (250) extends to shield the other 40% of the length of cutter (106), which extends distally from probe assembly (19). Of course, any other amount of the length of cutter (106)

may be retracted within probe assembly (16) when cutter (106) is in a retracted position. Similarly, telescoping cutter cover (250) may shield any other suitable length of cutter (106) extending distally from probe assembly (19) when cutter (106) is in a retracted position.

In some variations, telescopic cutter cover (250) is substituted with a design having multiple telescopic cutter covers (280), as seen in FIG. 52. In such an exemplary version, the multiple telescopic cutter covers (280) may comprise concentric hollow cylinders. Such covers (280) may be sping-biased distally like telescoping cutter cover (250) described above. Still other suitable variations of telescoping cutter cover (250) and covers (280) will be apparent to those of ordinary skill in the art in view of the teachings herein.

3. Exemplary Retractable Cutter

FIGS. 12-19 show an exemplary cutter exposure protection mode involving a fully retractable cutter (107). To achieve full translation of the cutter (107) and adequate rotation for cutting, probe assembly (18) of this example includes an internal helix mechanism (282) that surrounds cutter (107). Internal helix mechanism (282) includes a hollow tube (284), a fine thread lead screw (286), a gear (288), a lead screw nut (290), and a cutter driver (292). Hollow tube (284) is rotatable within probe assembly (18), and is formed with an interior track (294). Interior track (294) has a helical region (295) and a longitudinal region (297), which is distal to helical region (295). Cutter driver (292) is fixedly secured to the proximal end of cutter (107) (e.g., by overmolding, etc.), and includes an integral pin (296) that is configured to engage interior track (294). Lead screw nut (290) is also fixedly secured near the proximal end of cutter (107) (e.g., by overmolding, etc.). Cutter driver (292) and lead screw nut (290) thus rotate and translate unitarily with cutter (107) in this example.

A rotating drive gear (298) is exposed by holster assembly (20) in this example. As will be described in greater detail below, holster assembly (21) is operable to rotate drive gear (264). Drive gear (298) and gear (288) of internal helix mechanism (282) are positioned and configured such that gears (288, 298) mesh when probe assembly (18) is coupled with holster assembly (20). Rotation of drive gear (298) thus causes corresponding rotation of gear (288). Gear (288) is fixedly coupled with hollow tube (284) in this example, such that rotation of drive gear (298) also causes rotation of hollow tube (284) when probe assembly (18) is coupled with holster assembly (20). As tube (284) is rotated, cutter (107) translates longitudinally in this example. In particular, pin (296) of cutter driver (292) travels in interior track (294) of tube (284) as tube (284) is rotated. This longitudinal translation of cutter driver (292) causes corresponding translation of cutter (107), as cutter driver (292) is fixedly secured to cutter (107) in this example. Retraction or extension of the cutter (107) relative to the remainder of probe assembly (18) may thus be determined by the direction of rotation. It will be appreciated by those of ordinary skill in the art that the pitch of track (294) may be adjusted to provide greater or lesser translational movement per unit of rotation. Furthermore, it will be appreciated that the pitch of track (294) may be variable through the length of hollow tube (284) (e.g., a fast pitch region and a fine pitch region, etc.).

As shown, fine thread lead screw (286) is positioned longitudinally adjacent to and distal to hollow tube (284). Fine thread lead screw (286) is fixed within probe assembly (18), and includes a leaf spring (300), which biases a pin (302) toward cutter (107). Cutter (107) has a longitudinal slot (304) along a portion of its length. In particular, longitudinal slot begins near the distal end of cutter (107) and terminates at a selected proximal point on cutter (107). By way of example only, cutter (107) may have a stepped configuration such that a portion having slot (304) is of a greater outer diameter than the portion without slot (304). Thus, slot (304) terminates at or near a longitudinal position where cutter (107) outer diameter transitions.

Longitudinal slot (304) is configured to receive pin (302). Engagement of pin (302) in slot (304) prevents cutter (107) from rotating as pin (296) of cutter driver (292) travels in interior track (294) of tube (284). For instance, in the first stages of extending cutter (107) (or the later stages of retracting cutter (107)), as hollow tube (284) rotates and cutter (107) translates longitudinally, pivot pin (302) travels in slot (304), and prevents cutter (107) from rotating while permitting translational movement of cutter (107). Of course, any other suitable structures, components, features, configurations, or techniques may be used to restrict rotation of cutter (107) during stages of extending cutter (107) from probe assembly (18) and/or retracting cutter (107) into probe assembly (18).

As cutter (107) reaches an extended position (e.g., when the distal end of cutter (107) nears aperture (278) of attached needle assembly (29)), longitudinal slot (304) of the cutter (107) terminates and pivot pin (302) no longer restricts rotational movement of cutter (107). Furthermore, lead screw nut (290) engages fine thread lead screw (286) when cutter (107) reaches a sufficiently distally extended position. At this point, pin (296) of the cutter driver (292) reaches the transition from helical region (295) of interior track (294) to longitudinal region (297) of interior track (294). With pivot pin (302) no longer restricting rotational movement of cutter (107), and with pin (296) of cutter driver (292) at longitudinal region (297) of interior track (294), further rotational motion communicated to hollow tube (284) by gear (288) cause cutter (107) to rotate in this example. Furthermore, with cutter (107) at such an extended longitudinal position, lead screw nut (290) internally engages fine thread lead screw (286). Lead screw nut (290) and fine thread lead screw (286) have complementary threads, such that rotation of cutter (107) (and, hence, rotation of lead screw nut (290)) causes longitudinal translation of cutter (107). Longitudinal region (297) of interior track (294) permits pin (296) (and, hence, cutter (107)) to translate relative to hollow tube (284) during such engagement between threads of lead screw nut (290) and fine thread lead screw (286). Cutter (107) may thus rotate and translate simultaneously as hollow tube (284) is rotated throughout this longitudinal positioning of cutter (107), to sever a tissue sample from tissue protruding through aperture (278). After severing the tissue sample, retraction of cutter (107) may occur in reverse order and begins by imparting rotation to hollow tube (284) in the reverse direction.

An encoder gear (299) is also secured to hollow tube (284), such that encoder gear (299) rotates unitarily with hollow tube (284). Encoder gear (299) is configured to mesh with a complementary encoder gear (301) exposed by holster (20), when probe assembly (18) is coupled with holster assembly (20). Encoder gear (301) is coupled with an encoder (303) located within holster (20). Encoder (303) may thus be used to track the longitudinal position and/or rotation speed, etc., of cutter (107). Suitable encoders and ways in which encoder (303) may be used are disclosed in U.S. Non-Provisional patent application Ser. No. 12/337,942, entitled "TISSUE BIOPSY DEVICE WITH CENTRAL THUMBWHEEL," filed on even date herewith, now published as U.S. Pat. Pub. No. 2010/0160819, the disclosure of which is incorporated by reference herein. Of course, encoder (303) and associated components may be omitted, if desired.

C. Exemplary Hybrid Detachable Needle

In some settings, it may be desirable to have a first portion of a biopsy device needle provided as an integral component of the biopsy device, with a second portion of the needle being provided as a separate targeting cannula. For instance, FIGS. 53-56 show an exemplary partial needle (306) that may be used with a targeting cannula (308) and cutter (not shown), where it might be desirable to eliminate certain fluid sealing and detachable features of an MRI biopsy device such as those described above. In this example, cannula (308) may has an integral tissue piercing tip (310) as shown, which may be constructed of ceramic or any other suitable material. Cannula (308) also has a transverse aperture (312) near its distal end. In some versions, tip (310) may form the upper half of cannula (308) that is distal of aperture (312). This may be advantageous where tip (310) is formed of a ceramic material that is harder than the cutter (not shown) so skiving of the cannula material does not occur. Of course, tip (310) may be formed of any other desired material.

Figure 54:
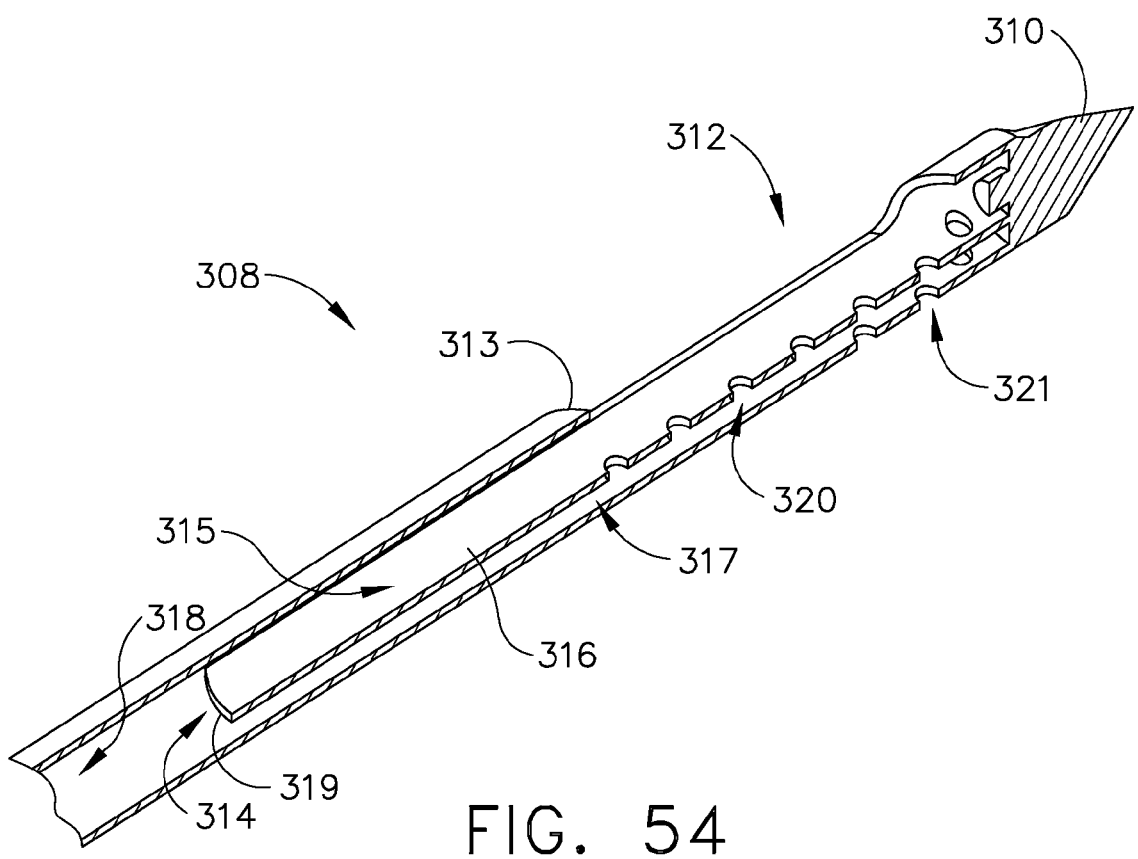
FIG. 54 depicts a cross-sectional view of the cannula of FIG. 53.
Figure 55:
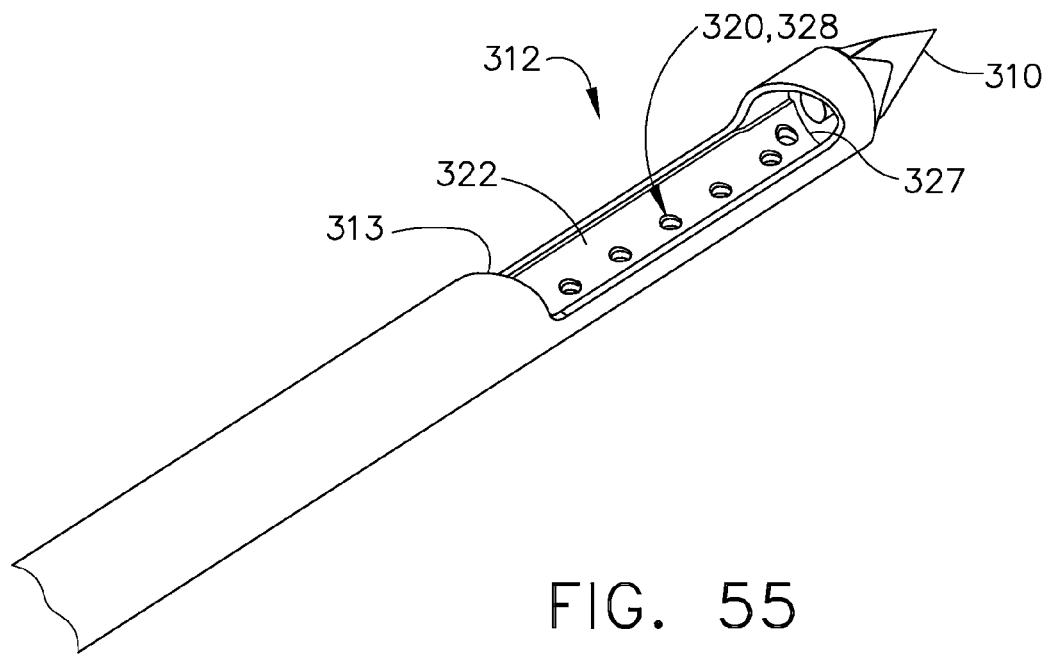
FIG. 55 depicts a perspective view of the cannula of FIG. 53 coupled with a modified biopsy probe needle.
Figure 56:
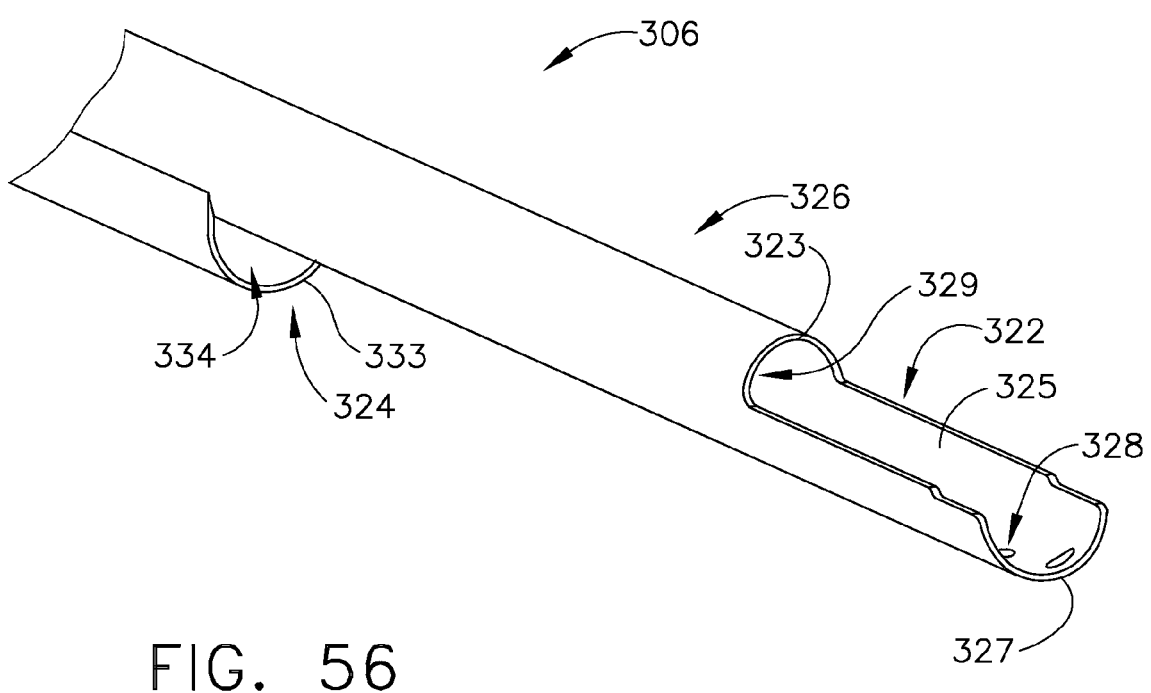
FIG. 56 depicts a perspective view of the modified needle of FIG. 55.
Figure 57:
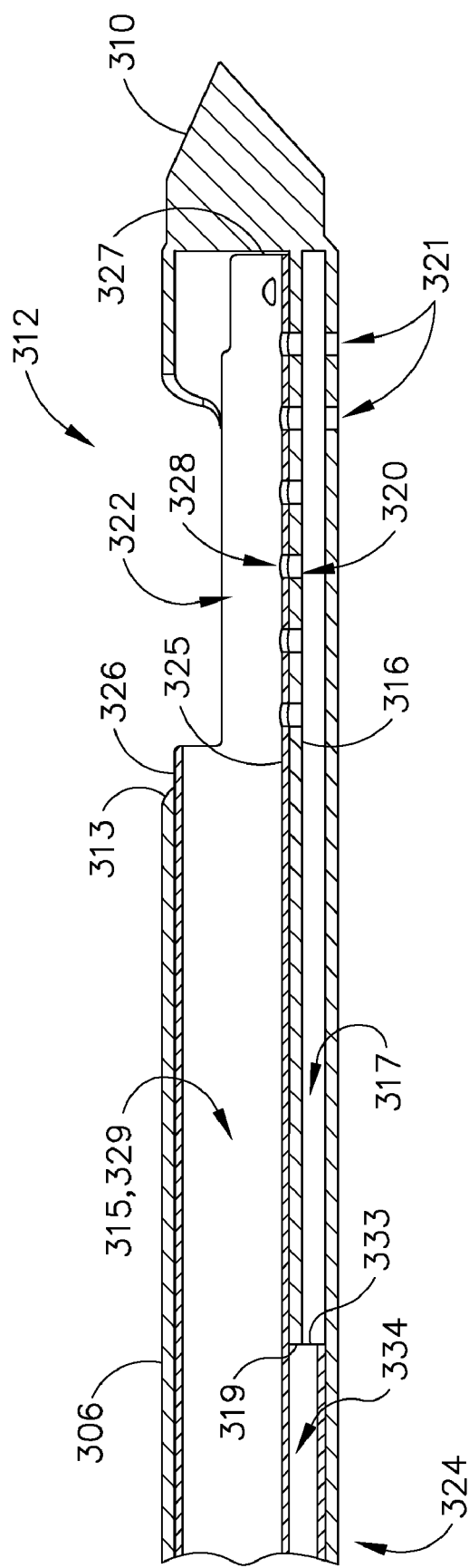
FIG. 57 depicts a cross-sectional view of the cannula of FIG. 53 coupled with the modified needle of FIG. 55.

Cannula (308) also includes a dual lumen portion (314) in its distal region. Dual lumen portion (314) may be achieved by including a dividing member (316) within cannula (308) in the distal region. Dividing member (316) partially extends longitudinally within cannula (308), proximally terminating at a proximal edge (319). Dividing member (316) thus creates an upper lumen (315) and a lower lumen (317). The portion of cannula (308) without dividing member (316) defines a single lumen portion (318). Dividing member (316) includes openings (320) that provide fluid communication between upper lumen (315) and lower lumen (317). Also, as shown in FIGS. 54 and 57, the outer portion of cannula (308), also includes a plurality of external openings (321). By way of example only, external openings (321) may be configured and used in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, external openings (321) are merely optional.

In the present example, a partial needle (306) extends distally from a probe (not shown). By way of example only, the probe may otherwise be configured in accordance with any of the teachings herein; any of the teachings of U.S. Pub. No. 2008/0195066, entitled "Revolving Tissue Sample Holder For Biopsy Device," published Aug. 14, 2008, the disclosure of which is incorporated by reference herein; or any of the teachings of U.S. Non-Provisional patent application Ser. No. 12/337,942, entitled "TISSUE BIOPSY DEVICE WITH CENTRAL THUMB WHEEL," filed on even date herewith, now published as U.S. Pat. Pub. No. 2010/0160819, the disclosure of which is incorporated by reference herein. Alternatively, the probe may have any other suitable configuration.

Partial needle (306) of the present example has a shovel end (322). Shovel end (322) has an upper distal edge (323), a tongue (325), and a lower distal edge (327) at the distal end of tongue (325). Tongue (325) has a plurality of openings (328) formed therethrough. Partial needle (306) also defines an upper lumen (329) and a lower lumen (334), which terminates at a lower lumen distal edge (333). Upper lumen (229) and lower lumen (334) together define a dual lumen region (324) of partial needle (306); while upper lumen (229) extends distally past lower lumen distal edge (333) to form a single lumen region (326) of partial needle (306).

As shown in FIG. 57, partial needle (306) of this example is configured to fit within cannula (308). In particular, lower distal edge (327) of shovel end (322) abuts the rear face of tip (310); while lower lumen distal edge (333) abuts proximal edge (319) of dividing member (316). Upper lumen (315) of cannula (308) thus unifies with upper lumen (329) of partial needle (306). Similarly, lower lumen (317) of cannula (308) thus unifies with lower lumen (334) of partial needle (306). In addition, openings (328) of tongue (328) align with openings (320) of dividing member (316), providing fluid communication between upper lumens (315, 329) and lower lumens (317, 334). Upper distal edge (323) also aligns with proximal edge (313) of aperture (312). Partial needle (306) and cannula (308) thus together form an assembly similar to needles (42, 44, 64) described herein. For instance, a vacuum may be drawn through lower lumens (317, 334) to pull tissue through aperture (312). A cutter (not shown) may then be advanced and rotated through upper lumens (315, 329) to sever a sample from such tissue; and the severed tissue sample may be communicated proximally through the lumen of the cutter while a vacuum is drawn through the cutter lumen and while lower lumens (317, 334) are vented.

In operation, cannula (308) may be positioned using any suitable guidance technique (e.g., MRI imaging). Cannula (308) may have an blunt obturator inserted therein (e.g., to "close off" aperture (312), etc.), and cannula (308) with obturator may be inserted into a patient's breast. After positioned, the obturator may be removed. At this stage, some tissue may naturally prolapse or otherwise protrude into aperture (312), even without a vacuum applied. A probe (not shown)—equipped with partial needle (306) and cutter (not shown)—may then be inserted into the positioned cannula (308) (e.g., until lower distal edge (327) of shovel end (322) abuts the rear face of tip (310)). The configuration of shovel end (322) may reduce any likelihood that partial needle (306) will move or otherwise interfere with any tissue that is naturally prolapsing or otherwise protruding into aperture (312) as partial needle (306) is inserted into cannula (308). Vacuum may then be induced in lower lumens (317, 334) to draw tissue into aperture (312). The cutter (not shown) may then be translated and rotated through upper lumens (315, 329) to sever the tissue sample. The severed tissue sample may then be transported through the lumen of the cutter to a tissue sample container (not shown), such as by inducing a vacuum in the cutter lumen while venting lower lumens (317, 334).

The foregoing is just one example of how a partial needle (306) may be configured relative to a targeting cannula (308). It should be understood that partial needle (306) and targeting cannula (308) may each be configured in a variety of other ways, and that partial needle (306) and targeting cannula (308) may have a variety of other relationships with each other. Suitable variations of partial needle (306) and targeting cannula (308) and their relationships will be apparent to those of ordinary skill in the art in view of the teachings herein.

D. Exemplary Vacuum Delivery and Tissue Sample Holding

Each probe assembly (14, 18, 19) discussed herein includes vacuum delivery and tissue sample holding. As noted above, biopsy devices (10, 12) described herein function to capture tissue samples, sever the tissue samples from the targeted tissue, and transport the tissue samples to a tissue sample holder.

In terms of vacuum delivery, vacuum may be delivered to a lateral lumen (84) in needle assembly (28, 29, 30, 134, 160, 161) as well as to an axial lumen defined by cutter (106, 107). The vacuum induced in lateral lumen (84) may aid in capturing the tissue sample for biopsy, such as by drawing tissue into aperture (278). The vacuum provided to the axial lumen in cutter (106, 107) may aid in transporting the severed tissue sample from the interior of the cutter to a tissue sample container (500). Various ways in which vacuum delivery and other fluid communication may be provided to and within any biopsy device (10, 12) described herein are disclosed in U.S. Pub. No. 2008/0195066, entitled "Revolving Tissue Sample Holder For Biopsy Device," published Aug. 14, 2008, the disclosure of which is incorporated by reference herein.

In terms of tissue sample containers (500), examples of such containers (500) are shown in FIGS. 1-10, 12-15, and 52. By way of example only, such containers (500) may include a rotatable manifold (not shown) and a plurality of tissue sample compartments (not shown) that may be successively indexed to the lumen of cutter (106, 107). For instance, the manifold may provide fluid communication to the lumen of cutter (106, 107) via a tissue sample compartment, and such fluid communication may be used to communicate a vacuum to draw a severed tissue sample through the lumen of cutter (106, 107) and into whichever tissue sample compartment is indexed with the lumen of cutter (106, 107). By way of example only, tissue sample container (500) may be configured and used in accordance with any of the teachings of U.S. Pub. No. 2008/0195066, entitled "Revolving Tissue Sample Holder For Biopsy Device," published Aug. 14, 2008, the disclosure of which is incorporated by reference herein. Alternatively, tissue sample container (500) may be configured in accordance with any of the teachings of U.S. Non-Provisional Patent Application Serial No. 12/337,911, entitled "BIOPSY DEVICE WITH DISCRETE TISSUE CHAMBERS," filed on even date herewith, now published as U.S. Pat. Pub. No. 2010/0160824, the disclosure of which is incorporated by reference herein. Of course, any other suitable structures or configurations for tissue sample container (500) may be used.

To the extent that tissue sample container (500) includes a rotatable portion to successively index discrete tissue sample compartments with the lumen of cutter (106, 107), there are a variety of mechanisms and features that may be used to rotate and otherwise operate such a rotatable portion. By way of example only, tissue sample container (500) may be rotatable in accordance with any of the teachings of U.S. Pub. No. 2008/0195066, entitled "Revolving Tissue Sample Holder For Biopsy Device," published Aug. 14, 2008, the disclosure of which is incorporated by reference herein. Alternatively, tissue sample container (500) may be rotatable in accordance with any of the teachings of U.S. Non-Provisional patent application Ser. No. 12/337,874, entitled "MECHANICAL TISSUE SAMPLE HOLDER INDEXING DEVICE," filed on even date herewith, now published as U.S. Pat.Pub. No. 2010/0160816, the disclosure of which is incorporated by reference herein. Alternatively, tissue sample container (500) may be rotatable in accordance with any of the teachings of U.S. Non-provisional patent application Ser. No. 12/337,942, entitled "TISSUE BIOPSY DEVICE WITH CENTRAL THUMB WHEEL," filed on even date herewith, now published as U.S. Pat. Pub. No. 2010/0160819, the disclosure of which is incorporated by reference herein. Of course, tissue sample container (500) may be rotatable in any other suitable fashion.

Furthermore, those of ordinary skill in the art will appreciate that a tissue sample container (500) may be omitted altogether if desired. A tissue sample container (500) may also be mounted on another assembly of a biopsy device (10, 12) instead of probe assembly (14, 18, 19) (e.g., to holster assembly (16, 20, 21)). Alternatively, tissue sample container (500) may be located separate from biopsy device (10, 12), such as by being remotely connected by a vacuum line that transports the tissue sample. Still other ways in which a tissue sample container may be incorporated into a biopsy device (10, 12) will be apparent to those of ordinary skill in the art in view of the teachings herein.

IV. Exemplary Holster Assemblies

As described briefly above and shown in FIGS. 1-14, 20-21, and 52 various holster assemblies (16, 20, 21) may be used with probe assemblies (14, 18, 19). For instance, holster assembly (16) coupled with probe assembly (14) in FIGS. 1-6 provides a cutter drive mechanism and a needle indexing mechanism. Similarly, holster assembly (20) coupled with probe assembly (18) in FIGS. 12-14, 20, and 21 also provides a cutter drive mechanism and a needle indexing mechanism. In another exemplary holster assembly (21), shown in FIGS. 7-11, a cutter drive mechanism may be provided, but a needle indexing mechanism may be provided separate from holster assembly (21). In these exemplary holster assemblies (16, 20, 21), the cutter drive and needle indexing mechanisms may be provided through a series of shafts and gears which may be driven by a motor (e.g., electric or pneumatic) or driven manually.

By way of example only, holster assemblies (16, 20, 21) may be configured in accordance with the teachings of U.S. Pub. No. 2008/0195066, entitled "Revolving Tissue Sample Holder For Biopsy Device," published Aug. 14, 2008, the disclosure of which is incorporated by reference herein. Alternatively, holster assemblies (16, 20, 21) may be configured in accordance with the teachings of U.S. Non-Provisional patent application Ser. No. 12/337,942, entitled "TISSUE BIOPSY DEVICE WITH CENTRAL THUMBWHEEL," filed on even date herewith, now published as U.S. Pat. Pub. No. 2010/0160819, the disclosure of which is incorporated by reference herein. Alternatively, holster assemblies (16, 20, 21) may have any other suitable structures, components, features, configurations, functionalities, and methods of operation. Suitable structures, components, features, configurations, functionalities, and methods of operation will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device, wherein the biopsy device comprises:
   (a) a detachable needle, wherein the detachable needle comprises a connecting member configured to selectively engage a biopsy probe; and
   (b) a biopsy probe, wherein the biopsy probe comprises:
      (i) a body having a distal end, a proximal end, and an exterior surface, wherein the body comprises a pivot pin proximal to the distal end of the body,
      (ii) a cutter comprising a hollow tube having a sharp distal end operable to sever tissue, wherein the cutter is operable to translate longitudinally relative to the body, and
      (iii) a locking member disposed on the exterior surface of the body, wherein the locking member comprises a port, wherein the port is located along a lateral portion of the locking member, wherein the port is configured to receive the pivot pin of the body such that the locking member is pivotable about an axis defined by the pivot pin, wherein the locking member is configured to engage the connecting member of the detachable needle.

2. The biopsy device of claim 1, wherein the connecting member comprises an annular groove.

3. The biopsy device of claim 2, wherein the locking member further comprises an engaging tab, wherein the engaging tab is located at a distal end of the locking member, wherein the engaging tab is configured to engage with the annular groove of the connecting member.

4. The biopsy device of claim 3, wherein the detachable needle is rotatable about a longitudinal axis upon engagement of the annular groove of the connecting member with the engaging tab of the locking member.

5. The biopsy device of claim 3, wherein the body further comprises a resilient member, wherein the resilient member is configured to bias the locking member about the pivot pin of the body.

6. The biopsy device of claim 5, wherein the resilient member comprises a spring, wherein the spring is located proximal from the pivot pin of the body, wherein the spring is aligned with a proximal portion of the locking member.

7. The biopsy device of claim 5, wherein the connecting member further comprises a chamfer along a proximal edge of the connecting member, wherein the chamfer is configured to deflect the engaging tab upon coupling of the biopsy probe with the detachable needle, wherein deflection of the engaging tab causes corresponding compression of the resilient member.

8. The biopsy device of claim 1, wherein the connecting member comprises a thumbwheel.

9. The biopsy device of claim 1, wherein the pivot pin extends transversely from the exterior wall of the body.

10. The biopsy device of claim 1, wherein the pivot pin is formed unitarily by the body.

11. A biopsy device, wherein the biopsy device comprises:
    (a) a detachable needle operable to penetrate tissue, wherein the detachable needle comprises a connecting member, wherein the connecting member defines a recess; and
    (b) a biopsy probe, wherein the biopsy probe comprises:
       (i) a body comprising a distal end and a proximal end,
       (ii) a cutter comprising a hollow tube having a sharp distal end operable to sever tissue, wherein the cutter is operable to translate longitudinally relative to the body,
       (iii) a locking ring at the distal end of the body, wherein the locking ring is configured to selectively engage the recess of the connecting member of the detachable needle, wherein the locking ring comprises an inwardly protruding and distally projecting locking member, wherein the inwardly protruding and distally projecting locking member is configured to enter at least a portion of the recess of the connecting member, and
       (iv) a locking ring engagement member, wherein the locking ring engagement member is movable relative to the locking ring to selectively disengage the inwardly protruding and distally projecting locking member from the recess of the connecting member.

12. The biopsy device of claim 11, wherein the inwardly protruding and distally projecting locking member is resiliently biased to enter at least a portion of the recess of the connecting member.

13. The biopsy device of claim 12, wherein the inwardly protruding and distally projecting locking member includes a chamfer located at a distal end of the inwardly protruding and distally projecting locking member, wherein the chamfer guides the inwardly protruding and distally projecting locking member outwardly upon attachment of the biopsy probe to the detachable needle.

14. The biopsy device of claim 12, wherein the locking ring engagement member is operable to deflect the inwardly protruding and distally projecting locking member outwardly to disengage the inwardly protruding and distally projecting locking member from the recess of the connecting member.

15. The biopsy device of claim 14, further comprising a lever, wherein the lever is operable to move the locking ring engagement member longitudinally to deflect the inwardly protruding and distally projecting locking member outwardly.

16. The biopsy device of claim 15, further comprising:
    (a) a pivot pin secured relative to the body, wherein the lever is operable to rotate about the pivot pin; and
    (b) an arm extending longitudinally from an end of the lever to the locking ring engagement member.

17. The biopsy device of claim 14, further comprising a pair of arms extending proximally from the locking ring engagement member, wherein the arms are operable to move the locking ring engagement member longitudinally to deflect the inwardly protruding and distally projecting locking member outwardly.

18. A biopsy device, wherein the biopsy device comprises:
(a) a detachable needle, wherein the detachable needle comprises a connecting member configured to selectively engage a biopsy probe, wherein the connecting member defines a recess; and
(b) a biopsy probe, wherein the biopsy probe comprises:
 (i) a body having a distal end, a proximal end, and an exterior surface, wherein the body comprises a pivot pin proximal to the distal end of the body,
 (ii) a cutter comprising a hollow tube having a sharp distal end operable to sever tissue, wherein the cutter is operable to translate longitudinally relative to the body, and
 (iii) a locking member disposed on the exterior surface of the body, wherein the locking member comprises a protrusion configured to selectively engage the recess to secure the biopsy probe relative to the detachable needle, wherein the locking member is selectively movable toward or away from the recess, wherein the protrusion is biased toward the recess.

19. The biopsy device of claim 18, wherein the locking member is selected from the group consisting of a resilient arm and a pivoting member.

* * * * *